(12) United States Patent
Holley et al.

(10) Patent No.: US 10,792,450 B2
(45) Date of Patent: Oct. 6, 2020

(54) DEVICE FOR RETAINING HUMIDITY IN A PATIENT INTERFACE

(71) Applicant: ResMed Pty Ltd, Bella Vista, New South Wales (AU)

(72) Inventors: Liam Holley, Sydney (AU); Emma Anne Connell, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 840 days.

(21) Appl. No.: 15/305,466

(22) PCT Filed: Apr. 23, 2015

(86) PCT No.: PCT/AU2015/050191
§ 371 (c)(1),
(2) Date: Oct. 20, 2016

(87) PCT Pub. No.: WO2015/161345
PCT Pub. Date: Oct. 29, 2015

(65) Prior Publication Data
US 2017/0035978 A1 Feb. 9, 2017

(30) Foreign Application Priority Data
Apr. 23, 2014 (AU) ................................ 2014901476

(51) Int. Cl.
*A61M 16/06* (2006.01)
*A61M 16/22* (2006.01)
(Continued)

(52) U.S. Cl.
CPC ........ *A61M 16/0605* (2014.02); *A61M 16/06* (2013.01); *A61M 16/22* (2013.01);
(Continued)

(58) Field of Classification Search
CPC combination set(s) only.
See application file for complete search history.

(56) References Cited

U.S. PATENT DOCUMENTS 4,782,832 A 11/1988 Trimble et al.
4,944,310 A 7/1990 Sullivan
(Continued)

FOREIGN PATENT DOCUMENTS

CN 102256653 A 11/2011
JP 2005-112693 4/2005
(Continued)

OTHER PUBLICATIONS

International Preliminary Report on Patentability issued in related PCT Application No. PCT/AU2015/050191 dated Oct. 25, 2016, 8 pages.
(Continued)

*Primary Examiner* — Samchuan C Yao
*Assistant Examiner* — Margaret M Luarca
(74) *Attorney, Agent, or Firm* — Nixon & Vanderhye P.C.

(57) ABSTRACT

A patient interface for sealed delivery of a flow of air to ameliorate sleep disordered breathing may include: a seal-forming structure to form a pneumatic seal with the entrance to the patient's airways; a positioning and stabilising structure to maintain the seal-forming structure in sealing contact with an area surrounding the entrance to the patient's airways; a plenum chamber pressurised at a pressure above ambient pressure in use; a connection port for the delivery of the flow of breathable gas into the patient interface; and a device positioned within a breathing chamber defined, at least in part, by the seal-forming structure and the plenum chamber, wherein the device divides the breathing chamber into a posterior chamber and an anterior chamber, and wherein the device comprises a plurality of apertures such that turbulence of the air in the posterior chamber is less than turbulence in the air in the anterior chamber.

22 Claims, 33 Drawing Sheets

(51) Int. Cl.
*A61M 16/00* (2006.01)
*A61M 16/10* (2006.01)
*A61M 16/08* (2006.01)
*A61M 16/16* (2006.01)

(52) U.S. Cl.
CPC ..... *A61M 16/0063* (2014.02); *A61M 16/0066* (2013.01); *A61M 16/0075* (2013.01); *A61M 16/0633* (2014.02); *A61M 16/0683* (2013.01); *A61M 16/0866* (2014.02); *A61M 16/107* (2014.02); *A61M 16/109* (2014.02); *A61M 16/1045* (2013.01); *A61M 16/16* (2013.01); *A61M 2016/0027* (2013.01); *A61M 2016/0039* (2013.01); *A61M 2205/02* (2013.01); *A61M 2205/3365* (2013.01); *A61M 2205/3368* (2013.01); *A61M 2205/3389* (2013.01); *A61M 2205/42* (2013.01); *A61M 2206/11* (2013.01)

(56) References Cited

U.S. PATENT DOCUMENTS

| | | | |
|---|---|---|---|
| 5,035,240 A * | 7/1991 | Braun | A62B 23/025 128/205.27 |
| 5,570,684 A * | 11/1996 | Behr | A61M 16/06 128/201.13 |
| 5,863,312 A * | 1/1999 | Wolfe | A41D 13/11 55/495 |
| 6,532,959 B1 | 3/2003 | Berthon-Jones | |
| 6,581,594 B1 | 6/2003 | Drew et al. | |
| 7,302,950 B2 | 12/2007 | Berthon-Jones et al. | |
| 7,866,944 B2 | 1/2011 | Kenyon et al. | |
| 8,336,547 B1 | 12/2012 | Ritchie et al. | |
| 8,636,479 B2 | 1/2014 | Kenyon et al. | |
| 8,638,014 B2 | 1/2014 | Sears et al. | |
| 8,733,349 B2 | 5/2014 | Bath et al. | |
| 2008/0142013 A1 | 6/2008 | Hallett et al. | |
| 2009/0044808 A1 | 2/2009 | Guney et al. | |
| 2009/0050156 A1 * | 2/2009 | Ng | A61M 16/1065 128/205.24 |
| 2009/0320851 A1 | 12/2009 | Selvarajan et al. | |
| 2010/0000534 A1 | 1/2010 | Kooij et al. | |
| 2010/0170514 A1 * | 7/2010 | Omer-Cooper | A61M 16/06 128/205.12 |
| 2010/0252037 A1 | 10/2010 | Wondka et al. | |
| 2010/0319700 A1 * | 12/2010 | Ng | A61M 16/06 128/206.28 |
| 2011/0232646 A1 | 9/2011 | Ho et al. | |
| 2011/0297152 A1 * | 12/2011 | Duveen | A61M 16/06 128/203.29 |
| 2012/0199130 A1 | 8/2012 | Euvrard et al. | |
| 2013/0190643 A1 | 7/2013 | Brambilla | |

FOREIGN PATENT DOCUMENTS

| | | |
|---|---|---|
| JP | 2006-122268 | 5/2006 |
| JP | 2008-264566 | 11/2008 |
| WO | WO 98/04310 A1 | 2/1998 |
| WO | WO 98/34665 A1 | 8/1998 |
| WO | WO 00/78381 A1 | 12/2000 |
| WO | WO 2004/073778 A1 | 9/2004 |
| WO | WO 2005/063328 A1 | 7/2005 |
| WO | WO 2006/074513 A1 | 7/2006 |
| WO | WO 2006/130903 A1 | 12/2006 |
| WO | WO 2009/052560 A1 | 4/2009 |
| WO | WO 2010/135785 A1 | 12/2010 |
| WO | WO 2012/171072 A1 | 12/2012 |
| WO | WO 2013/020167 A1 | 2/2013 |

OTHER PUBLICATIONS

First Office Action issued in related Chinese Application No. 201580033915.5 with English translation, dated May 4, 2018, 13 pages.
First Office Action issued in related Japanese Application No. 2016-564013 dated Jan. 11, 2019, with English translation, (13 pages).
Supplementary Search Report issued in related European Application No. 15 78 3428.4 dated Dec. 1, 2017, (8 pages).
Examination Report issued in related European Application No. 15 78 3428.4 dated Nov. 26, 2018, (5 pages).
International Search Report for PCT/AU2015/050191, dated Aug. 27, 2015, 8 pages.
Written Opinion of the ISA for PCT/AU2015/050191, dated Aug. 27, 2015, 7 pages.
West, John B., "Respiratory Physiology", Lippincott Williams & Wilkins, 9th edition published 2012, 8 pages.

* cited by examiner

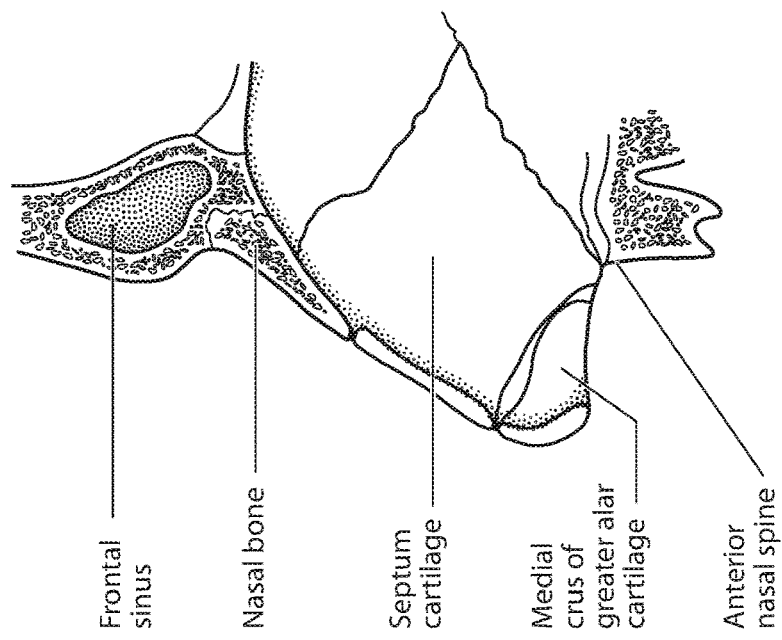
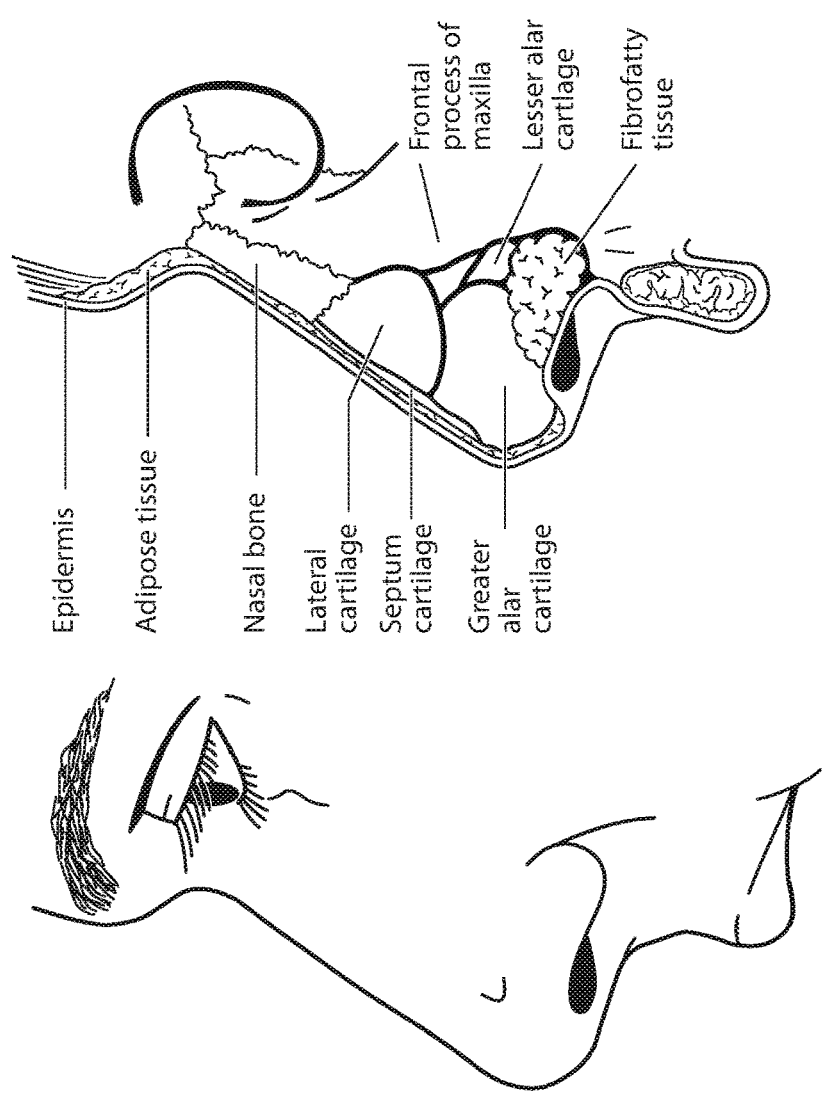
FIG. 2G  FIG. 2H  FIG. 2I

DEVICE FOR RETAINING HUMIDITY IN A PATIENT INTERFACE

1 CROSS-REFERENCE TO RELATED APPLICATIONS

This application is the U.S. national phase of International Application No. PCT/AU2015/050191 filed Apr. 23, 2015 which designated the U.S. and claims priority to Australian Provisional Application No. AU 2014901476, filed Apr. 23, 2014, the entire contents of each of which are hereby incorporated herein by reference.

2 BACKGROUND OF THE TECHNOLOGY

2.1 Field of the Technology

The present technology relates to one or more of the detection, diagnosis, treatment, prevention and amelioration of respiratory-related disorders. The present technology also relates to medical devices or apparatus, and their use.

2.2 Description of the Related Art

2.2.1 Human Respiratory System and its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2011.

A range of respiratory disorders exist. Certain disorders may be characterised by particular events, e.g. apneas, hypopneas, and hyperpneas.

Obstructive Sleep Apnea (OSA), a form of Sleep Disordered Breathing (SDB), is characterized by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

2.2.2 Therapy

Continuous Positive Airway Pressure (CPAP) therapy has been used to treat Obstructive Sleep Apnea (OSA). The hypothesis is that continuous positive airway pressure acts as a pneumatic splint and may prevent upper airway occlusion by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient in taking a full breath and/or maintain adequate oxygen levels in the body by doing some or all of the work of breathing. The ventilatory support is provided via a patient interface. NIV has been used to treat CSR, OHS, COPD, MD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

2.2.3 Diagnosis and Treatment Systems

These therapies may be provided by a treatment system or device. Systems and devices may also be used to diagnose a condition without treating it.

A treatment system may comprise a Respiratory Pressure Therapy Device (RPT device), an air circuit, a humidifier, a patient interface, and data management.

Another form of treatment system is a mandibular repositioning device.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cmH$_2$O relative to ambient pressure. For other forms of therapy, such as the delivery of oxygen, the patient interface may not include a seal sufficient to facilitate delivery to the airways of a supply of gas at a positive pressure of about 10 cmH$_2$O.

The design of a patient interface presents a number of challenges. The face has a complex three-dimensional shape. The size and shape of noses varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. For example, masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.1.1 Seal-Forming Portion

Patient interfaces may include a seal-forming portion. Since it is in direct contact with the patient's face, the shape and configuration of the seal-forming portion can have a direct impact the effectiveness and comfort of the patient interface.

A patient interface may be partly characterised according to the design intent of where the seal-forming portion is to engage with the face in use. In one form of patient interface, a seal-forming portion may comprise two sub-portions to engage with respective left and right nares. In one form of patient interface, a seal-forming portion may comprise a single element that surrounds both nares in use. Such single element may be designed to for example overlay an upper lip region and a nasal bridge region of a face. In one form of patient interface a seal-forming portion may comprise an element that surrounds a mouth region in use, e.g. by forming a seal on a lower lip region of a face. In one form of patient interface, a seal-forming portion may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming portion that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming portions may be designed for mass manufacture such that one design fit and be comfortable and effective for a wide range of different face shapes and sizes. To the extent to which there is a mismatch between the shape of the patient's face, and the seal-forming portion of the mass-manufactured patient interface, one or both must adapt in order for a seal to form.

One type of seal-forming portion extends around the periphery of the patient interface, and is intended to seal against the patient's face when force is applied to the patient interface with the seal-forming portion in confronting engagement with the patient's face. The seal-forming portion may include an air or fluid filled cushion, or a moulded or formed surface of a resilient seal element made of an elastomer such as a rubber. With this type of seal-forming portion, if the fit is not adequate, there will be gaps between the seal-forming portion and the face, and additional force will be required to force the patient interface against the face in order to achieve a seal.

Another type of seal-forming portion incorporates a flap seal of thin material positioned about the periphery of the mask so as to provide a self-sealing action against the face of the patient when positive pressure is applied within the mask. Like the previous style of seal forming portion, if the match between the face and the mask is not good, additional force may be required to achieve a seal, or the mask may leak. Furthermore, if the shape of the seal-forming portion does not match that of the patient, it may crease or buckle in use, giving rise to leaks.

Another type of seal-forming portion may comprise a friction-fit element, e.g. for insertion into a naris, however some patients find these uncomfortable.

Another form of seal-forming portion may use adhesive to achieve a seal. Some patients may find it inconvenient to constantly apply and remove an adhesive to their face.

A range of patient interface seal-forming portion technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO2004/073,778 (describing amongst other things aspects of the ResMed Limited SWIFT™ nasal pillows), US Patent Application 2009/0044808 (describing amongst other things aspects of the ResMed Limited SWIFT™ LT nasal pillows); International Patent Applications WO 2005/063, 328 and WO 2006/130,903 (describing amongst other things aspects of the ResMed Limited MIRAGE LIBERTY™ full-face mask); International Patent Application WO 2009/052,560 (describing amongst other things aspects of the ResMed Limited SWIFT™ FX nasal pillows).

2.2.3.1.2 Positioning and Stabilising

A seal-forming portion of a patient interface used for positive air pressure therapy is subject to the corresponding force of the air pressure to disrupt a seal. Thus a variety of techniques have been used to position the seal-forming portion, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

2.2.3.1.3 Vent Technologies

Some forms of patient interface systems may include a vent to allow the washout of exhaled carbon dioxide. The vent may allow a flow of gas from an interior space of the patient interface, e.g., the plenum chamber, to an exterior of the patient interface, e.g., to ambient. The vent may comprise an orifice and gas may flow through the orifice in use of the mask. Many such vents are noisy. Others may become blocked in use and thus provide insufficient washout. Some vents may be disruptive of the sleep of a bed-partner 1100 of the patient 1000, e.g. through noise or focussed airflow.

ResMed Limited has developed a number of improved mask vent technologies. See International Patent Application Publication No. WO 1998/034,665; International Patent Application Publication No. WO 2000/078,381; U.S. Pat. No. 6,581,594; US Patent Application Publication No. US 2009/0050156; US Patent Application Publication No. 2009/0044808.

Table of noise of prior masks
(ISO 17510-2: 2007, 10 cmH$_2$O pressure at 1 m)

| Mask name | Mask type | A-weighted sound power level dB(A) (uncertainty) | A-weighted sound pressure dB(A) (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |
| ResMed Mirage ™ (*) | nasal | 29.5 | 21.5 | 1998 |
| ResMed UltraMirage ™ | nasal | 36 (3) | 28 (3) | 2000 |
| ResMed Mirage Activa ™ | nasal | 32 (3) | 24 (3) | 2002 |
| ResMed Mirage Micro ™ | nasal | 30 (3) | 22 (3) | 2008 |
| ResMed Mirage ™ SoftGel | nasal | 29 (3) | 22 (3) | 2008 |
| ResMed Mirage ™ FX | nasal | 26 (3) | 18 (3) | 2010 |
| ResMed Mirage Swift ™ (*) | nasal pillows | 37 | 29 | 2004 |
| ResMed Mirage Swift ™ II | nasal pillows | 28 (3) | 20 (3) | 2005 |
| ResMed Mirage Swift ™ LT | nasal pillows | 25 (3) | 17 (3) | 2008 |
| ResMed AirFit P10 | nasal pillows | 21 (3) | 13 (3) | 2014 |

(* one specimen only, measured using test method specified in ISO3744 in CPAP mode at 10 cmH$_2$O) Sound pressure values of a variety of objects are listed below

| Object | A-weighted sound pressure dB(A) | Notes |
|---|---|---|
| Vacuum cleaner: Nilfisk Walter Broadly Litter Hog: B+ Grade | 68 | ISO3744 at 1 m distance |
| Conversational speech | 60 | 1 m distance |
| Average home | 50 | |
| Quiet library | 40 | |
| Quiet bedroom at night | 30 | |
| Background in TV studio | 20 | |

2.2.3.2 Respiratory Pressure Therapy (RPT) Device

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices
(one specimen only, measured using test method specified in
ISO3744 in CPAP mode at 10 cmH₂O).

| RPT Device name | A-weighted sound power level dB(A) | Year (approx.) |
|---|---|---|
| C-Series Tango ™ | 31.9 | 2007 |
| C-Series Tango ™ with Humidifier | 33.1 | 2007 |
| S8 Escape ™ II | 30.5 | 2005 |
| S8 Escape ™ II with H4i ™ Humidifier | 31.1 | 2005 |
| S9 AutoSet ™ | 26.5 | 2010 |
| S9 AutoSet ™ with H5i Humidifier | 28.6 | 2010 |

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

2.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air. A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small. A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore medical humidifiers may have more stringent safety constraints than industrial humidifiers While a number of medical humidifiers are known, they can suffer from one or more shortcomings. Some medical humidifiers may provide inadequate humidification, some are difficult or inconvenient to use by patients.

2.2.3.4 Heat and Moisture Exchangers (HMEs)

HME's may be utilized in RPT therapy as a passive form of humidification. HMEs work by partially recovering heat and moisture present in exhaled gas from patients. This heat and moisture can be retained and recycled to the patient in a passive manner as a flow of breathable gas passes through the HME prior to inspiration. Thus, the use of HME's can provide the needed moisture and humidity (generally recognized as >10 mg/l) to most patients during RPT therapy to minimize any detrimental effects associated with RPT therapy and non-humidified ambient air while avoiding the need for a heated humidifier system. The use of a HME rather than a heated humidifier may also lower the possibility of occlusion caused by condensation in air delivery tubes. Heat and moisture exchangers are generally made up of foam, paper, or a substance capable of acting as a condensation and absorption surface. Generally, the material carries hygroscopic salts to improve the water-retaining capacity. Suitable salts include calcium chloride.

When selecting a suitable HME, careful consideration of material, swept length (thickness), flow area and internal surface area of the HME as well as integrated mask airflow or vent design is required to deliver an effective passive humidification system. These factors are important for ensuring that the right level of humidification may be reached while trying to minimise impact on the PAP therapy delivered to a patient.

There is a need to provide passive humidification to a patient on PAP therapy while minimising the negative effect on patient therapy, inadequate CO2 washout, and reducing overall bulk and weight of the patient interface.

2.2.3.5 Mandibular Repositioning

A mandibular repositioning device (MRD) or mandibular advancement device (MAD) is one of the treatment options for sleep apnea and snoring. It is an adjustable oral appliance available from a dentist or other supplier that holds the lower jaw (mandible) in a forward position during sleep. The MRD is a removable device that a patient inserts into their mouth prior to going to sleep and removes following sleep. Thus, the MRD is not designed to be worn all of the time. The MRD may be custom made or produced in a standard form and includes a bite impression portion designed to allow fitting to a patient's teeth. This mechanical protrusion of the lower jaw expands the space behind the tongue, puts tension on the pharyngeal walls to reduce collapse of the airway and diminishes palate vibration.

In certain examples a mandibular advancement device may comprise an upper splint that is intended to engage with or fit over teeth on the upper jaw or maxilla and a lower splint that is intended to engage with or fit over teeth on the upper jaw or mandible. The upper and lower splints are connected together laterally via a pair of connecting rods. The pair of connecting rods are fixed symmetrically on the upper splint and on the lower splint.

In such a design the length of the connecting rods is selected such that when the MRD is placed in a patient's mouth the mandible is held in an advanced position. The length of the connecting rods may be adjusted to change the level of protrusion of the mandible. A dentist may determine a level of protrusion for the mandible that will determine the length of the connecting rods.

Some MRDs are structured to push the mandible forward relative to the maxilla while other MADs, such as the ResMed Narval CC™ MRD are designed to retain the mandible in a forward position. This device also reduces or minimises dental and temporo-mandibular joint (TMJ) side effects. Thus, it is configured to minimises or prevent any movement of one or more of the teeth.

2.2.4 Monitoring Systems

Polysomnography (PSG) is a conventional system for diagnosis and prognosis of cardio-pulmonary disorders.

PSG typically involves the placement of 15 to 20 contact sensors on a person in order to record various bodily signals such as electroencephalography (EEG), electrocardiography (ECG), electrooculograpy (EOG), etc. However, while they may be suitable for their usual application in a clinical setting, such systems are complicated and potentially expensive, and/or may be uncomfortable or impractical for a patient at home trying to sleep.

The designer of a device may be presented with an infinite number of choices to make to design a product or system. Design criteria often conflict, meaning that certain design choices are far from routine or inevitable. Furthermore, the comfort and efficacy of certain aspects may be highly sensitive to small, subtle changes in one or more parameters.

3 BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to apparatus used in the diagnosis, amelioration, treatment or prevention of a respiratory disorder.

Another aspect of the present technology relates to methods used in the diagnosis, amelioration, treatment or prevention of a respiratory disorder.

An aspect of certain forms of the present technology is to provide methods and/or apparatus that improve the compliance of patients with respiratory therapy.

Another aspect of the present technology is directed to a patient interface for providing a flow of pressurized, breathable gas to a patient's airways for the treatment of a respiratory disorder. The patient interface may comprise a seal-forming structure to form pneumatic seal with the entrance to the patient's airways, a plenum chamber, a device or insert positioned within the plenum chamber to divide the plenum chamber into an anterior chamber and a posterior chamber, wherein the device or insert comprises a plurality of apertures to allow gas to flow between the anterior chamber and the posterior chamber, and wherein, in use, the gas in the posterior chamber is less turbulent than the gas in the anterior chamber.

One form of the present technology comprises a patient interface comprising a device comprising at least one aperture, the device having a predetermined surface area, the device comprising at least one aperture having a predetermined size; the device being positioned along a flow path of the flow of breathable gas; wherein the predetermined size of the at least one aperture and the predetermined surface area of the device are selected such that a predetermined amount of breathable gas flows through the at least one aperture; and wherein the device is heat non-absorbent or resistant to the absorption of heat and moisture non-absorbent or resistant to the absorption of moisture and the device changes the flow flowing towards a mucosal surface of a patient's airways such that a rate of heat and water loss from the mucosal surface is reduced.

In an example, the flow may be directed away from the mucosal surface. The flow may be directed away from the mucosal surface by changing the flow from a turbulent flow to a laminar flow. By directing the predetermined amount of breathable gas through the at least one aperture to change a turbulent flow to a laminar flow, a rate of heat and water loss from the mucosal surface may be reduced. During RPT treatment, a turbulent flow of the flow of breathable gas delivered to the mucosal surface of the patient's airways may result in evaporation of moisture on the surface and ultimately cause drying. Drying of the mucosal surface affects breathing comfort. It is the desire of the present technology to provide a patient interface comprising a device to prevent drying on the mucosal surface of a patient's airways during RPT treatment to promote breathing comfort. The device may alter the flow of breathable gas being delivered to the patient such that the flow converts from a turbulent flow to a more laminar flow, or a less turbulent flow, which results in reduced evaporation at the mucosal surface. The device may act by directing air through apertures that are sized to allow the appropriate amount of breathable gas to flow through to provide RPT treatment to induce the desired reduction in turbulence. The apertures may also be sized to change the flow of breathable gas from a turbulent flow to a laminar flow to a sufficient level such that the rate of heat and moisture loss from the mucosal surface is reduced. The device may also comprise a large enough surface area to direct enough of the breathable through the apertures. It is also desirable to prevent drying at the mucosal surface of a patient's airways to a sufficient level that breathing comfort is maintained without the need for a HME or any other added humidification, e.g., via a humidifier.

In another aspect of the present technology, the number and size of the apertures may be selected such that a flow of the breathable gas may be directed through the apertures within a predetermined pressure range set by the RPT device to ensure that occlusions of the patient's airways can be reduce or minimized in spite of the increased flow impedance that may be imparted by the presence of the device in the flow path. In a further aspect of the present technology, the number and size of the apertures may be selected such that a flow of the breathable gas may be directed through the apertures within a predetermined pressure range set by the RPT device to ensure that occlusions of the patient's airways can be reduce or minimized without significantly resisting expiration of $CO_2$ by the patient or $CO_2$ washout, which could cause $CO_2$ build-up in the plenum chamber and $CO_2$ rebreathing.

Another aspect of one form of the present technology is the patient interface further comprising an elbow in fluid communication with the connection port and wherein the device is positioned within the elbow. In a further aspect of one form of the present technology, the connection port may be in fluid connection to an air delivery conduit for delivery of the flow of breathable gas and wherein the device may be positioned within the air delivery conduit in the flow path of the flow of breathable gas. It is the desire of the present technology to provide a device that may be positioned anywhere in the flow path of the flow of breathable gas during RPT treatment to reduce a turbulence of the flow of breathable gas towards a mucosal surface of a patient's airways.

Another aspect of one form of the present technology a predetermined surface area of the device is selected to direct all the flow of breathable gas through the aperture. It is the desire of the present technology to physically interfere with and direct a laminar flow of the flow of breathable gas on the mucosal surface of a patient's airways to prevent evaporation at the surface and ultimately prevent drying.

Another aspect of one form of the present technology is the patient interface further comprises a vent for washout of exhaled air from the patient interface. The device may be positioned in a flow path of the flow of breathable gas between the vent and the entrance of a patient's airways, when in use. Preferably, the device may be positioned in close proximity to a patient's airways to maximise its effect on the physical interference of the flow of breathable gas.

Another aspect of one form of the present technology is the patient interface further comprises a plenum chamber separated by the device, into a first anterior chamber and a second posterior chamber configured to be in fluid communication with the entrance of the patient's airways. The device may be positioned within the plenum chamber such that it spans an entire cross sectional surface area of the plenum chamber. The device may be positioned within the plenum chamber to minimise its impedance of the flow of breathable gas as the plenum chamber may have a larger volume for housing the device in comparison to the connection port, conduit or elbow.

Another aspect of one form of the present technology is directed to the device, wherein the device physically interferes with a flow of expiratory gas to increase the humidity in the second posterior chamber to a predetermined absolute humidity. The predetermined absolute humidity may be greater than 10 mg/L. It is desirable to provide a device to physically interfere with the flow of expiratory gas to retain the moisture in the second posterior chamber of the patient interface such that the moisture is in close proximity to the entrance of a patient's airways for redelivery. It is also desirable to provide a level of moisture is equivalent to a predetermined absolute humidity that is sufficient to prevent drying of the mucosal surface in a patient's airways to prevent breathing discomfort.

It should be understood that the increase in absolute humidity, as compared to a patient interface without the device, may be the result of the device reducing humidity loss from the second, posterior chamber. The absolute humidity in the second, posterior chamber is increased by expiration by the patient expiring gas humidified by the mucosal surfaces of the patient's airways and the loss of this moisture may be caused by venting the humidified gas from the plenum chamber.

Another aspect of one form of the present technology is the device comprising at least one aperture having a predetermined size, and wherein the predetermined size of the at least one aperture is selected to such that the predetermined amount of the breathable gas flows through the aperture to deliver the flow of breathable gas at a predetermined level of pressure. The predetermined level of pressure may be between 2 cm of H2O to 40 cm of H2O. The predetermined size of the aperture may be selected to increase a permeability of the device to the flow of breathable gas. The permeability may be increased by increasing an anterior flow area of the aperture. The anterior flow area is the surface area of the device on an anterior side of the device facing away from the entrance to the patient's airways. The permeability of the device may also be increased by increasing the number of apertures. It is desirable to provide a device that does not significantly impede the flow of breathable gas to maintain a predetermined pressure level. Pressure levels in RPT treatment and particularly for PAP therapy in the treatment of OSA and other SDB conditions requires a set therapeutic level of pressure delivered to the entrance airways. Thus, it is also desirable to provide a device comprising apertures to prevent a significant pressure loss when a pressurised flow of breathable gas is delivered to the patient interface, such that a therapeutic level of pressure is maintained and delivered to the entrance of the patient's airways.

Another aspect of one form of the present technology is directed towards the device comprising apertures having the predetermined size selected to allow a flow of expiratory gas through the aperture for a predetermined level of CO2 washout through the vent. The apertures may comprise an inner surface profile configured to direct the flow of expiratory gas towards the vent for CO2 washout. The predetermined size of the aperture may be selected to increase a permeability of the device to the flow of expiratory gas for CO2 washout. The permeability may be increased by increasing a posterior flow area of the aperture. The posterior flow area of the apertures may be increased by increasing the size of the aperture on a posterior side of the device. The permeability of the device may also be increased by increasing the number of apertures. It is desirable to provide a device that does not impede the flow of expiratory gas for sufficient CO2 washout. Impeding the flow of expiratory gas to the vent for CO2 washout results in the increase of CO2 concentrations in the patient interface and will effectively result in CO2 rebreathing. Thus, it is also desirable to provide a device comprising apertures for expiratory gas flow through, wherein the device has an increased permeability to the flow of expiratory gas for sufficient CO2 washout.

Another aspect of one form of the present technology is the device, wherein the device a flexible membrane sheet. Alternatively, the device is a textile formed of woven fibres and wherein the fibres form a plurality of the apertures between adjacent fibres. The device may also be a mesh structure. The device may be a thin flexible structure that does not occupy a significant volume along the flow path of RPT treatment, such as within the plenum chamber of the patient interface. The thin structure allows for reduced flow impedance during RPT treatment and also allows easier positioning of the device in a fixed volume of space along the flow path. Moreover, the flexibility of the device allows for ease in manipulating the device to conform to the inner volume of a patient interface.

Another aspect of one form of the present technology is the device, wherein the device has a reduced thickness to reduce a flow impedance of the flow breathable gas. The thickness may be in the range of about 0.5 cm to 1 cm. The thickness may alternatively be in the range of 1 mm to 0.5 cm. The thickness may be less than 1 mm. A thinner device may occupy a smaller volume within the plenum chamber of the patient interface, reducing its impact on flow impedance and its impact on occupying the volume needed to accommodate a portion of the patient's face. Thus, it is desirable to provide a device that has a reduced thickness to reduce the impact on flow impedance on the flow of breathable gas and the flow of expiratory gas and effectively reduce the volume in which the device occupies within the plenum chamber. It is also desirable to provide a device that effectively reduces drying of the mucosal surface of a patient's airways, while having less flow impedance and occupying a smaller volume in a patient interface when compared to a HME. A HME is heat and moisture absorbent and therefore requires a volume of absorbent substrate to be able to capture the desired level of humidity. In contrast, it is also a desire of the present technology to prevent drying of the mucosal surface of the patient's airways and redeliver humidity from expiratory gas to the patient without the need to a heat and moisture absorbent material.

Another aspect of the present technology is directed to a patient interface for sealed delivery of a flow of air at a continuously positive pressure with respect to ambient air pressure to an entrance to the patient's airways including at least an entrance of a patient's nares, wherein the patient interface is configured to maintain a therapy pressure in a range of about 4 cmH2O to about 30 cmH2O above ambient air pressure in use, throughout the patient's respiratory cycle, while the patient is sleeping, to ameliorate sleep disordered breathing. The patient interface may comprise: a seal-forming structure to form a pneumatic seal with the entrance to the patient's airways; a positioning and stabilising structure to maintain the seal-forming structure in sealing contact with an area surrounding the entrance to the patient's airways while maintaining a therapeutic pressure at the entrance to the patient's airways; a plenum chamber pressurised at a pressure above ambient pressure in use; a connection port for the delivery of the flow of breathable gas into the patient interface; and a device having a predetermined surface area comprising at least one aperture having a predetermined size; the device positioned along a flow path of breathable gas to physically interfere with the flow; wherein the predetermined size of the at least one aperture and the predetermined surface area of the device are selected such that a predetermined amount of breathable gas flows through the at least one aperture; and wherein the device is heat non-absorbent and moisture non-absorbent and the device changes the flow of breathable gas flowing towards a mucosal surface of the patient's airways from a turbulent flow to a laminar flow by directing the predetermined amount of breathable gas through the at least one aperture such that a rate of heat and water loss from the mucosal surface is reduced.

In examples, (a) the patient interface may further comprise an elbow in fluid communication with the connection port and wherein the device is positioned within the elbow, (b) the patient interface may further comprise an air delivery conduit for delivering the flow of breathable gas to the patient interface, the air delivery conduit in fluid communication with the connection port and wherein the device is positioned within the conduit, (c) the patient interface may further comprise a gas washout vent configured to allow a flow of patient exhaled CO2 to an exterior of the patient interface to minimise rebreathing of exhaled CO2 by the patient, (d) the device may be positioned in a flow path of the flow of breathable gas between the vent and the entrance of the patient's airways, when in use, (e) the device may be positioned within the plenum chamber such that the plenum chamber is divided into a first anterior chamber and a second posterior chamber, the second posterior chamber being proximal to the entrance of the patient's airways relative to the first anterior chamber, (f) the device may physically interfere with a flow of expiratory gas to increase the humidity in the second posterior chamber to a predetermined absolute humidity, (g) the device may physically interfere with the flow of expiratory gas by decelerating the flow of expiratory gas to the first anterior chamber for redelivery to the entrance of the patient's airways, (h) the predetermined absolute humidity may be greater than 10 mg/L, (i) the predetermined size of each at least one aperture may be selected to substantially maintain a predetermined level of pressure when the flow of breathable gas flows through the aperture, (j) the predetermined level of pressure may be between 2 cm of H2O to 40 cm of H2O, (k) the predetermined size of the at least one aperture may be selected to maintain the predetermined pressure level by increasing a permeability of the device to the flow of breathable gas, (l) the permeability may be increased by increasing an anterior flow area of the aperture, (m) the anterior flow area of the aperture may be increased by increasing the size of the aperture on an anterior side of the device, (n) the at least one aperture may be a plurality of apertures and permeability of the device may be increased by increasing the number of apertures, (o) the predetermined size of the aperture may be selected to allow a flow of expiratory gas to flow through the apertures for a predetermined level of CO2 washout through the vent, (p) the aperture may comprise an inner surface profile configured to direct the flow of expiratory gas towards the vent for CO2 washout, (q) the predetermined size of the aperture may be selected to increase a permeability of the device to the flow of expiratory gas for CO2 washout, the permeability may be increased by increasing a posterior flow area of the aperture, (r) the posterior flow area of the apertures may be increased by increasing the size of the aperture on a posterior side of the device, (s) the at least one apertures may comprise a plurality of apertures and the permeability of the device may be increased by increasing the number of apertures, (t) the device may be a flexible membrane sheet, (u) the device may be a textile formed of woven fibres and the fibres may form a plurality of the apertures between adjacent fibres, (v) the device may be a mesh structure, (w) the device may comprise a material from any one of the group consisting of: synthetic materials, thermoplastic elastomers or hydrophobic polymers, (x) the device may have a predetermined thickness selected to reduce a flow impedance of the flow breathable gas, (y) the predetermined thickness of the device may be in the range of about 0.5 cm to 1 cm, (z) the predetermined thickness of the device may be in the range of about 1 mm to 0.5 cm, (aa) the predetermined thickness of the device may be less than 1 mm, and/or (bb) the predetermined size of the device may be selected to fit within the plenum chamber of the patient interface.

Another aspect of the present technology is directed to a patient interface for sealed delivery of a flow of air at a continuously positive pressure with respect to ambient air pressure to an entrance to the patient's airways including at least an entrance of a patient's nares, wherein the patient interface is configured to maintain a therapy pressure in a range of about 4 cmH2O to about 30 cmH2O above ambient air pressure in use, throughout the patient's respiratory cycle, while the patient is sleeping, to ameliorate sleep disordered breathing. The patient interface may comprising: a seal-forming structure to form a pneumatic seal with the entrance to the patient's airways; a positioning and stabilising structure to maintain the seal-forming structure in sealing contact with an area surrounding the entrance to the patient's airways while maintaining a therapeutic pressure at the entrance to the patient's airways; a plenum chamber pressurised at a pressure above ambient pressure in use; a connection port for the delivery of the flow of breathable gas into the patient interface; and a device positioned within a breathing chamber defined, at least in part, by the seal-forming structure and the plenum chamber when the seal-forming structure is in sealing contact with the area surrounding the entrance to the patient's airways, wherein the device divides the breathing chamber into a posterior chamber and an anterior chamber, and wherein the device comprises a plurality of apertures such that turbulence of the air in the posterior chamber is less than turbulence in the air in the anterior chamber.

In examples, (a) the device may be positioned, shaped, and dimensioned such that the air in the breathing chamber moving between the posterior chamber and the anterior chamber only passes through the plurality of apertures, (b) the device may be shaped and dimensioned such that at least a portion of an outer peripheral edge region of the device substantially conforms to an internal surface of at least one of the seal-forming structure and the plenum chamber, (c) the outer peripheral edge region may form a pneumatic seal against the internal surface of at least one of the seal-forming structure and the plenum chamber, (d) the entire outer peripheral edge region of the device may substantially conform to the internal surface of at least one of the seal-forming structure and the plenum chamber, (e) the patient interface may further comprise at least one gap between the outer peripheral edge region of the device and the internal surface of at least one of the seal-forming structure and the plenum chamber, (f) at least a portion of the outer peripheral edge region of the device may be fixedly attached to the internal surface of at least one of the seal-forming structure and the plenum chamber, (g) at least a portion of the outer peripheral edge region of the device may be removably attached to the internal surface of at least one of the seal-forming structure and the plenum chamber, (h) the plurality of apertures may be uniform in at least one of size, shape, and density across the entire device, (i) the plurality of apertures may not be uniform in at least one of size, shape, and density across the entire device, (j) each of the plurality of apertures may have a posterior area adjacent to the posterior chamber and an anterior area adjacent to the anterior chamber, (k) the posterior area of each of the plurality of apertures may be greater than, less than, or equal to the anterior area of each of the plurality of apertures, (l) a flow path through each of the plurality of apertures may be linear or non-linear, (m) the device may comprise a material that is resistant to absorption of moisture and/or heat, (n) the material may be any one of the group consisting of nylon, polycarbonate, silicone, polyurethane, thermoplastic elastomers, hydrophobic polymers, and other synthetic materials, (o) the device may comprise a single, continuous, and homogeneous piece of the material, (p) the device may have a mesh, foam, or woven structure, (q) the device may be positioned within the breathing chamber such that the volume of the posterior chamber is greater than, less than, or equal to the volume of the anterior chamber, (r) the patient interface may further comprise a vent to washout gas from the patient interface, (s) the vent may be positioned on the plenum chamber or an elbow of the patient interface such that gas from the anterior chamber is washed out via the vent, and/or (t) the vent and the connection port may be positioned opposite the entrance to patient's airways relative to the device.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Treatment Systems

FIG. 1A shows a system including a patient 1000 wearing a patient interface 3000, in the form of a nasal pillows, receiving a supply of air at positive pressure from an RPT device 4000. Air from the RPT device is humidified in a humidifier 5000, and passes along an air circuit 4170 to the patient 1000. A bed partner 1100 is also shown.

4.2 Respiratory System and Facial Anatomy

Figure 1A:
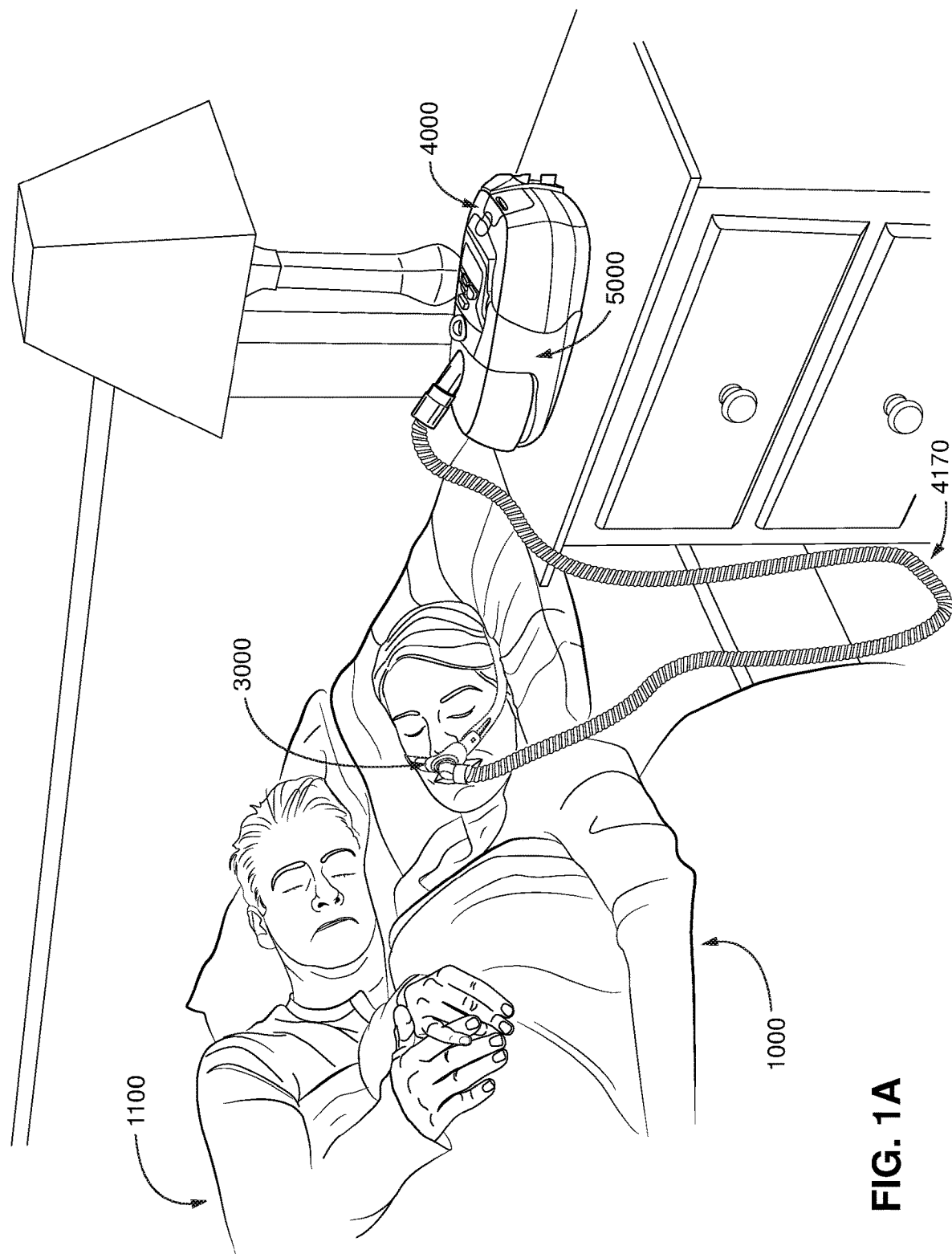
FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.
FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000.
Figure 1B:
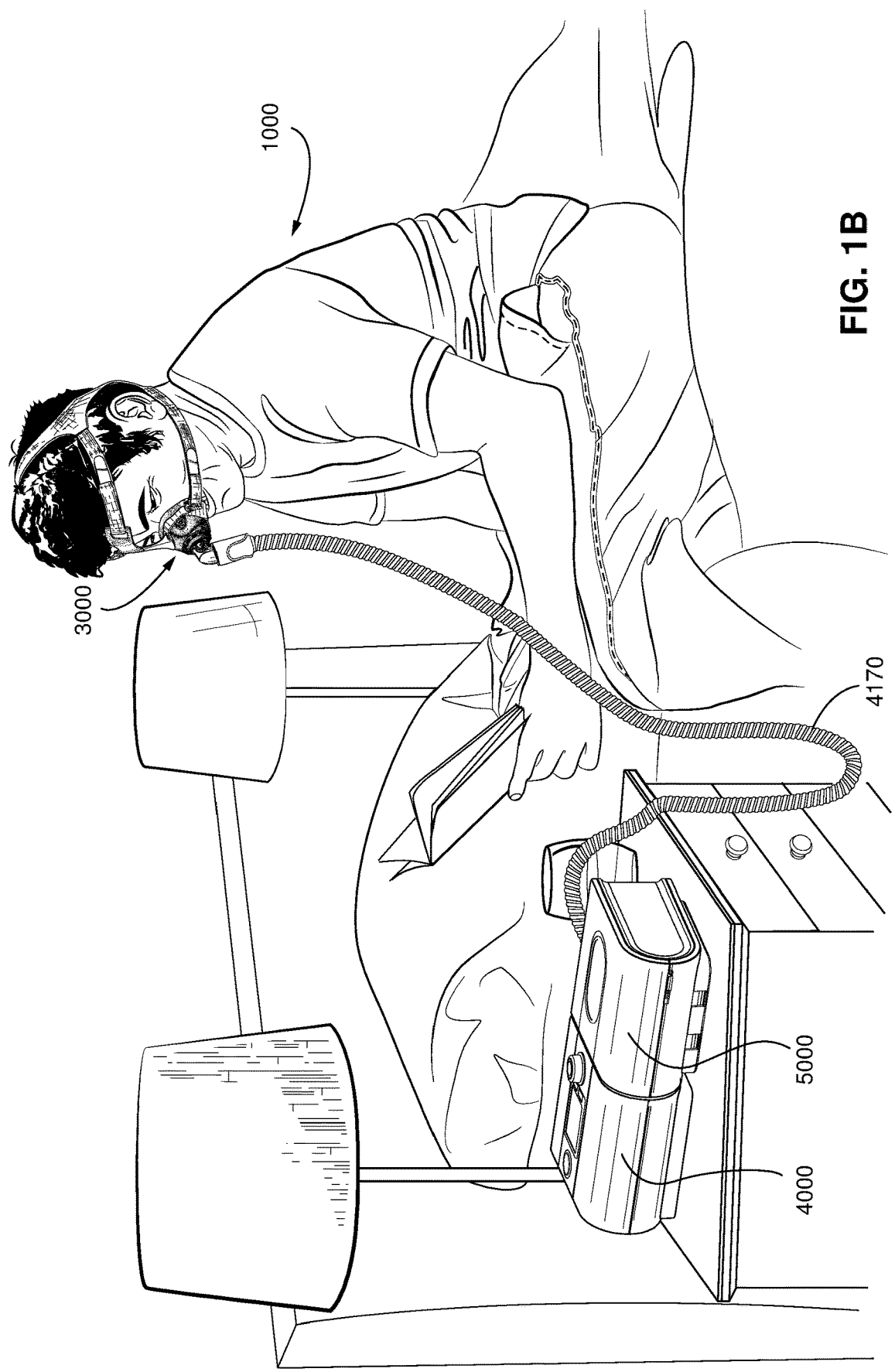
Figure 1C:
Figure 2A:
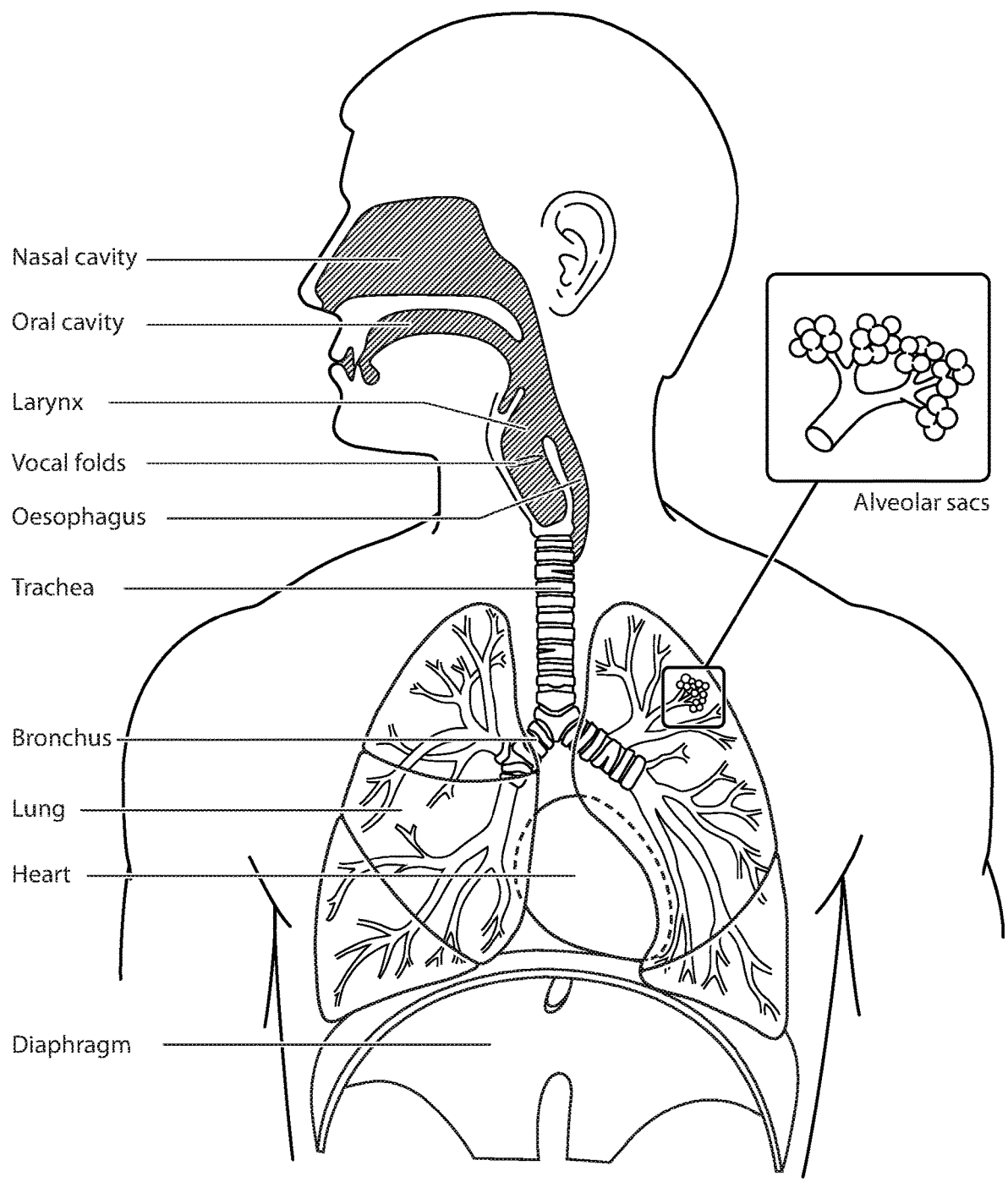

FIG. 2A shows an overview of a human respiratory system including the nasal and oral cavities, the larynx, vocal folds, oesophagus, trachea, bronchus, lung, alveolar sacs, heart and diaphragm.

Figure 2B:
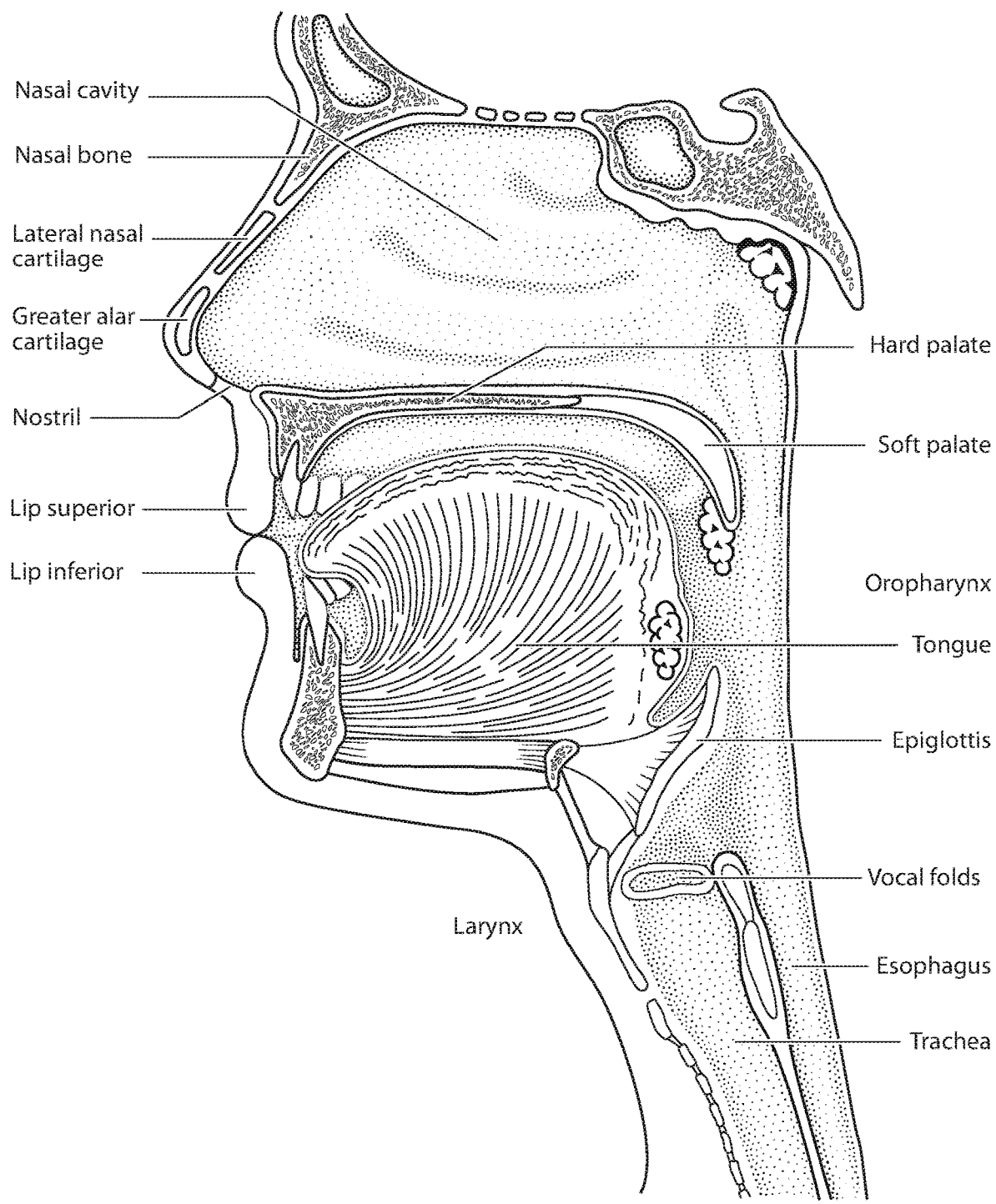

FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

Figure 2C:
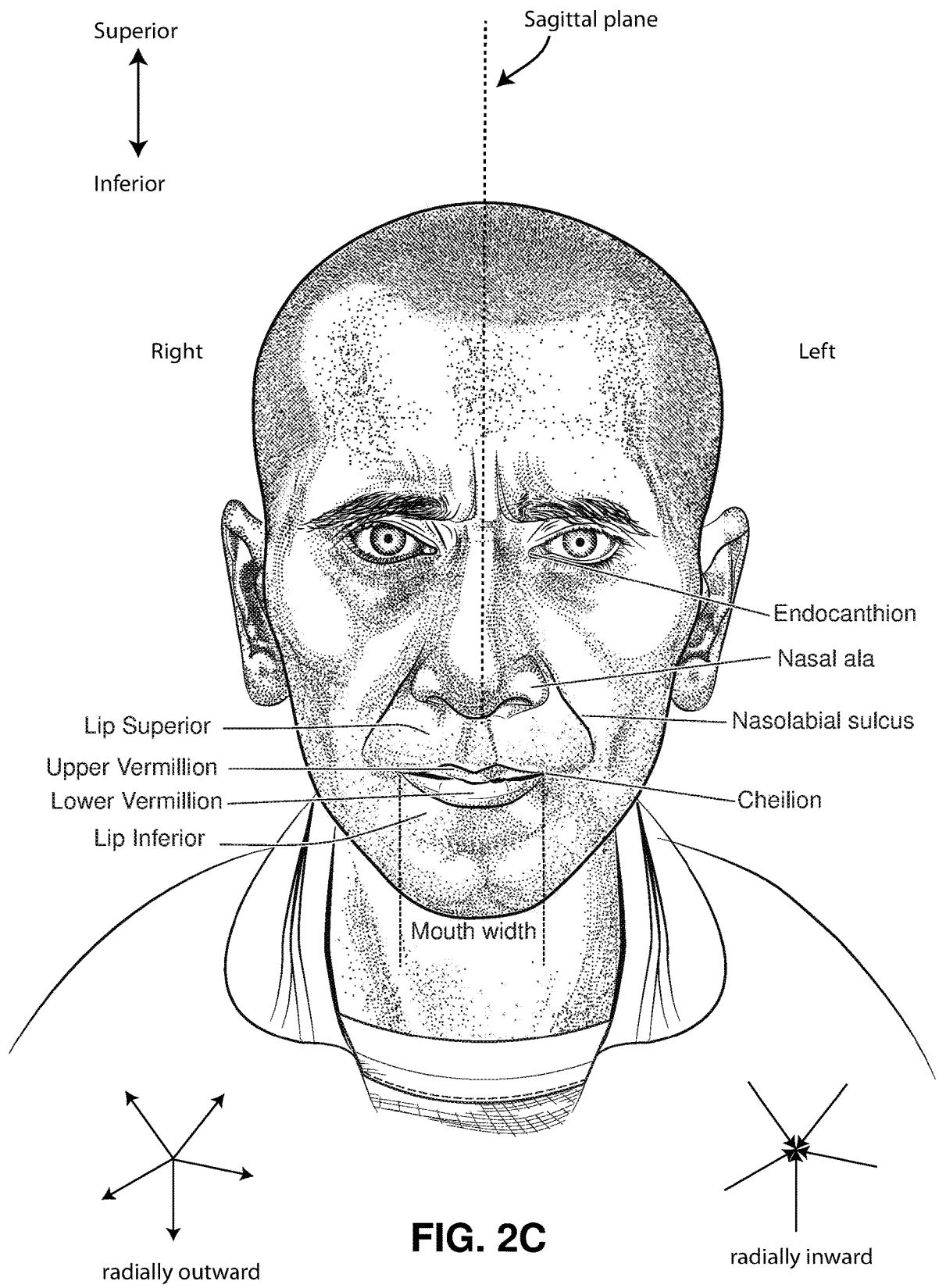

FIG. 2C is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.

Figure 2D:
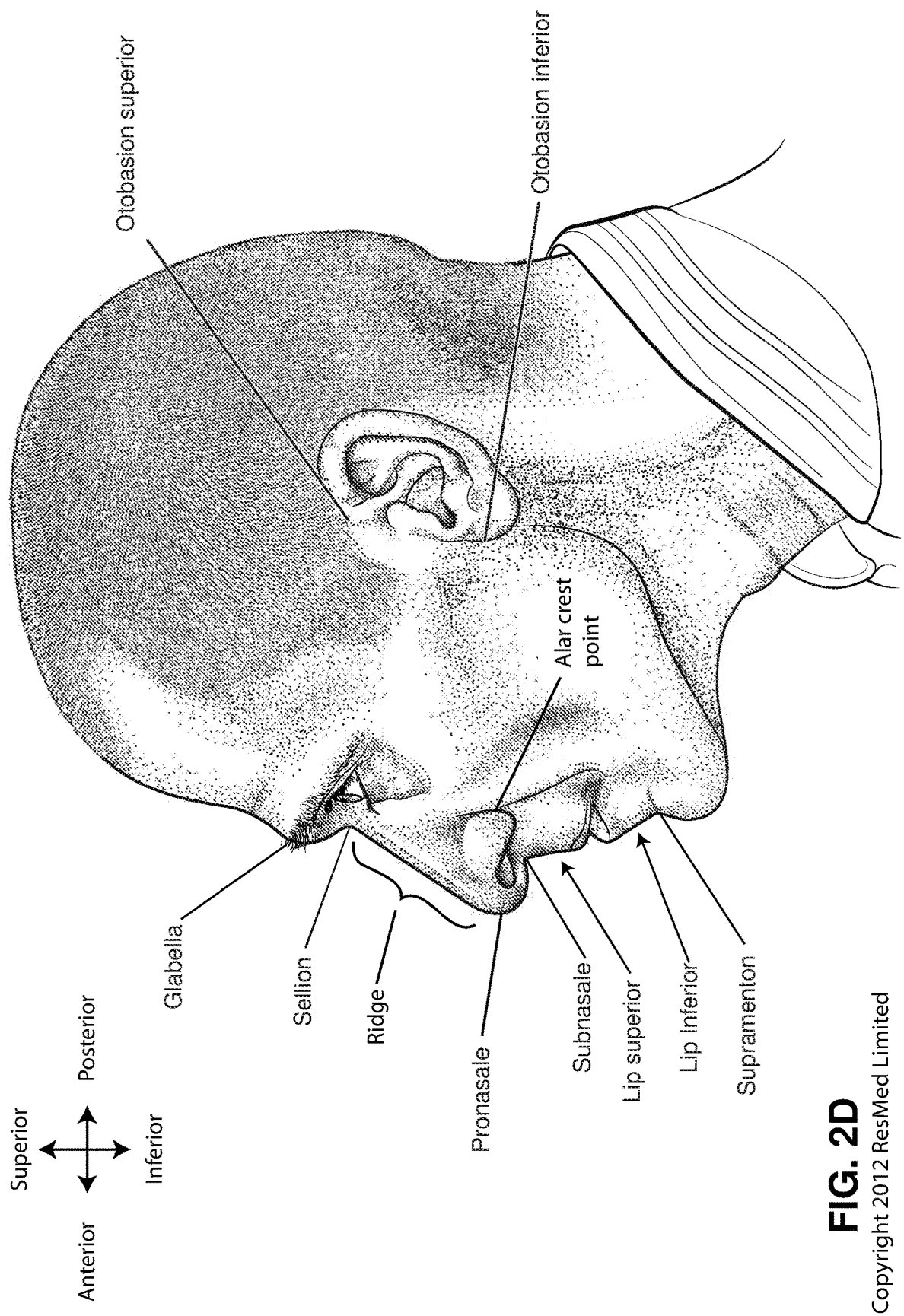

FIG. 2D is a side view of a head with several features of surface anatomy identified including glabella, sellion, pronasale, subnasale, lip superior, lip inferior, supramenton, nasal ridge, alar crest point, otobasion superior and otobasion inferior. Also indicated are the directions superior & inferior, and anterior & posterior.

Figure 2E:
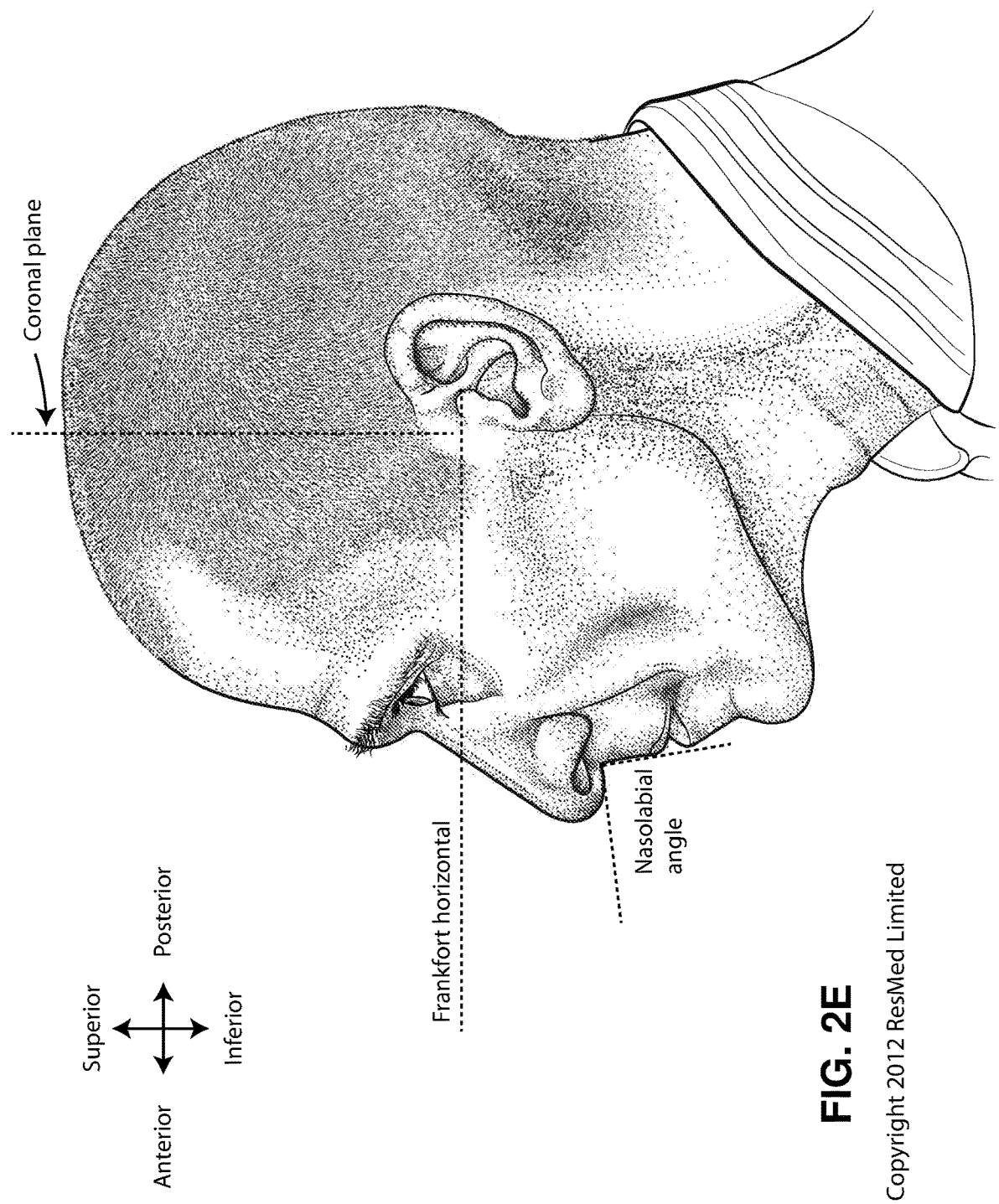

FIG. 2E is a further side view of a head. The approximate locations of the Frankfort horizontal and nasolabial angle are indicated. The coronal plane is also indicated.

Figure 2F:
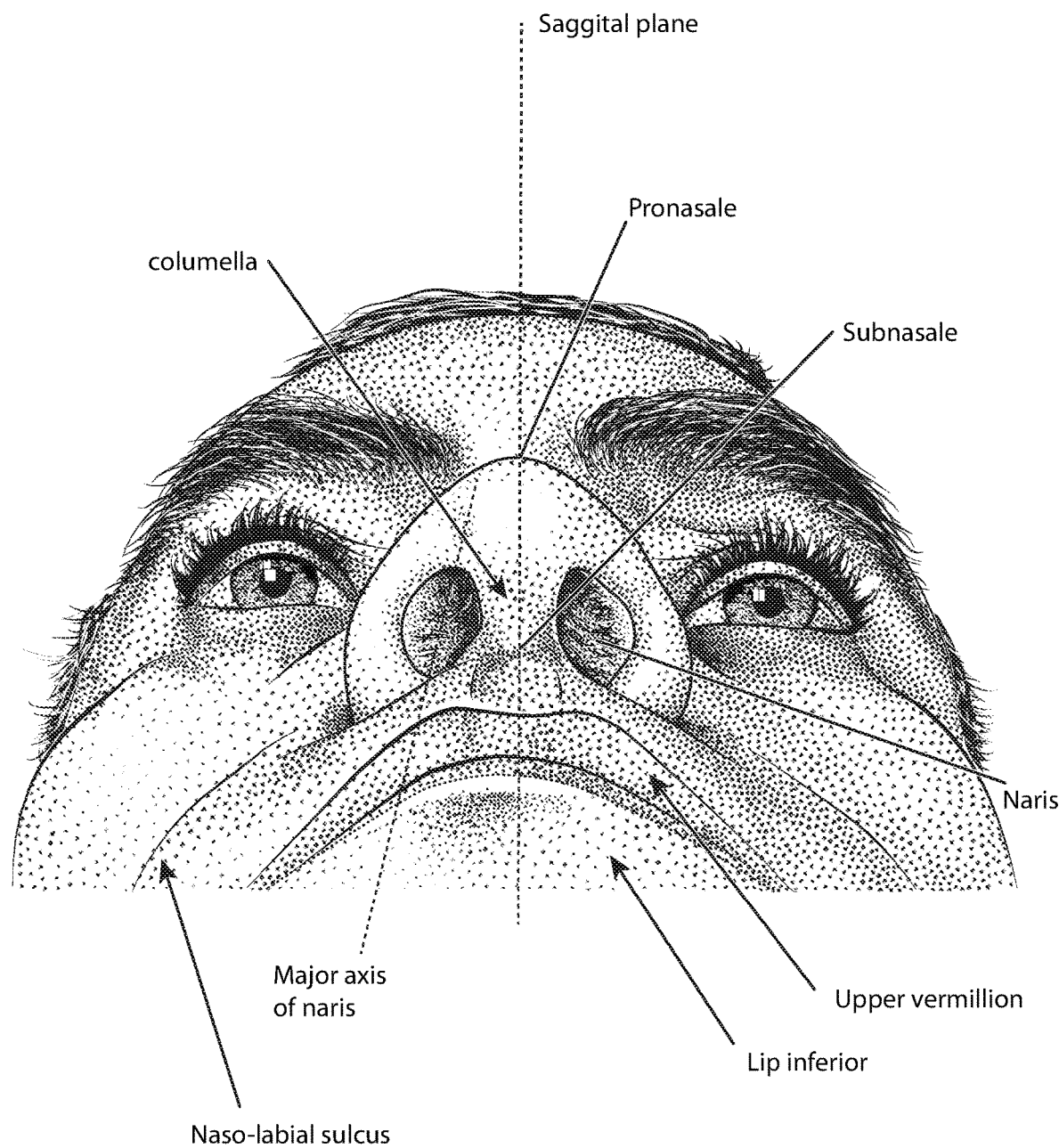

FIG. 2F shows a base view of a nose with several features identified including naso-labial sulcus, lip inferior, upper Vermilion, naris, subnasale, columella, pronasale, the major axis of a naris and the sagittal plane.

FIG. 2G shows a side view of the superficial features of a nose.

FIG. 2H shows subcutaneal structures of the nose, including lateral cartilage, septum cartilage, greater alar cartilage, lesser alar cartilage, sesamoid cartilage, nasal bone, epidermis, adipose tissue, frontal process of the maxilla and fibrofatty tissue.

FIG. 2I shows a medial dissection of a nose, approximately several millimeters from a sagittal plane, amongst other things showing the septum cartilage and medial crus of greater alar cartilage.

Figures 2J, 2K:
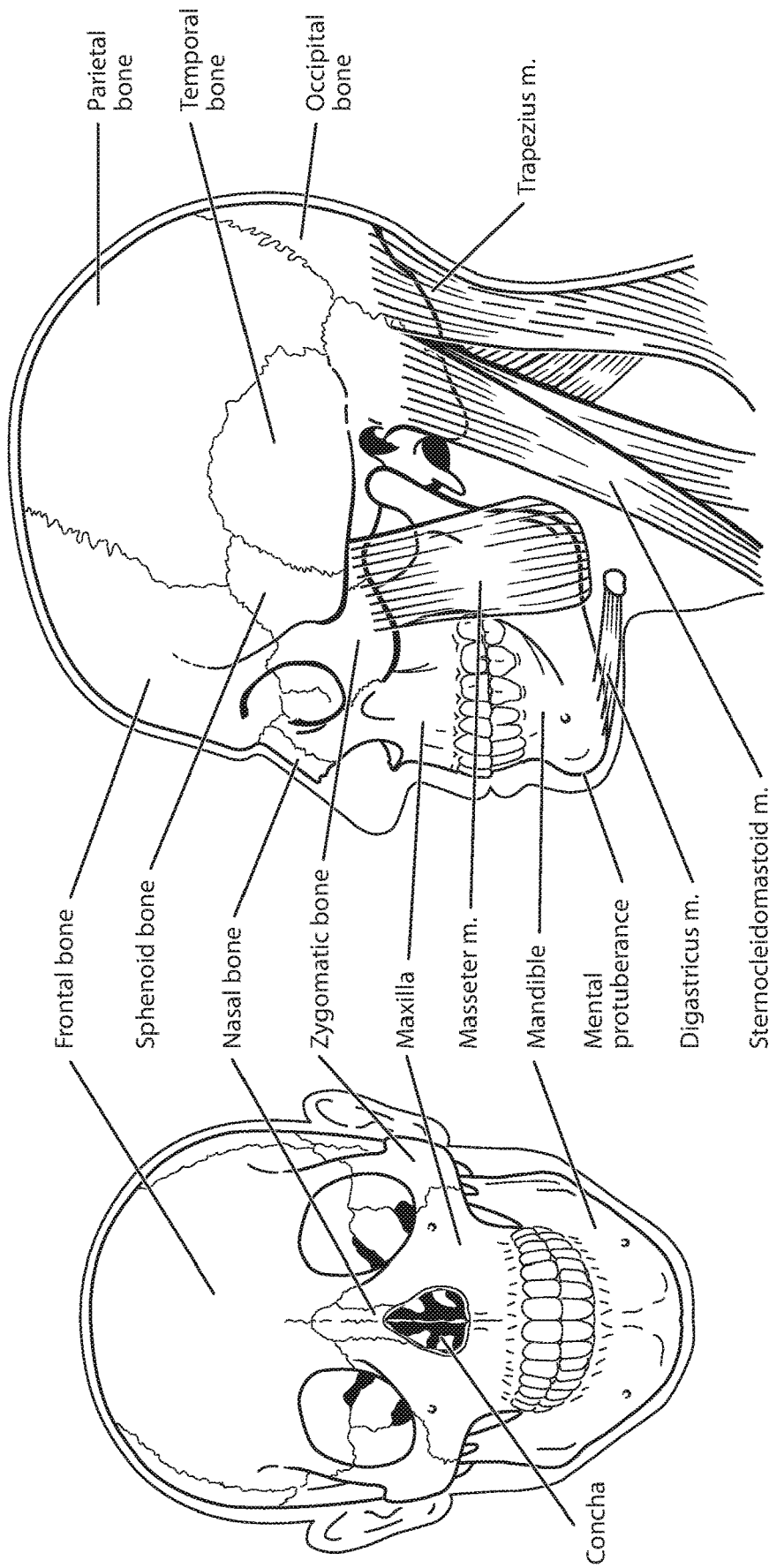

FIG. 2J shows a front view of the bones of a skull including the frontal, nasal and zygomatic bones. Nasal concha are indicated, as are the maxilla, and mandible.

FIG. 2K shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.

Figure 2L:
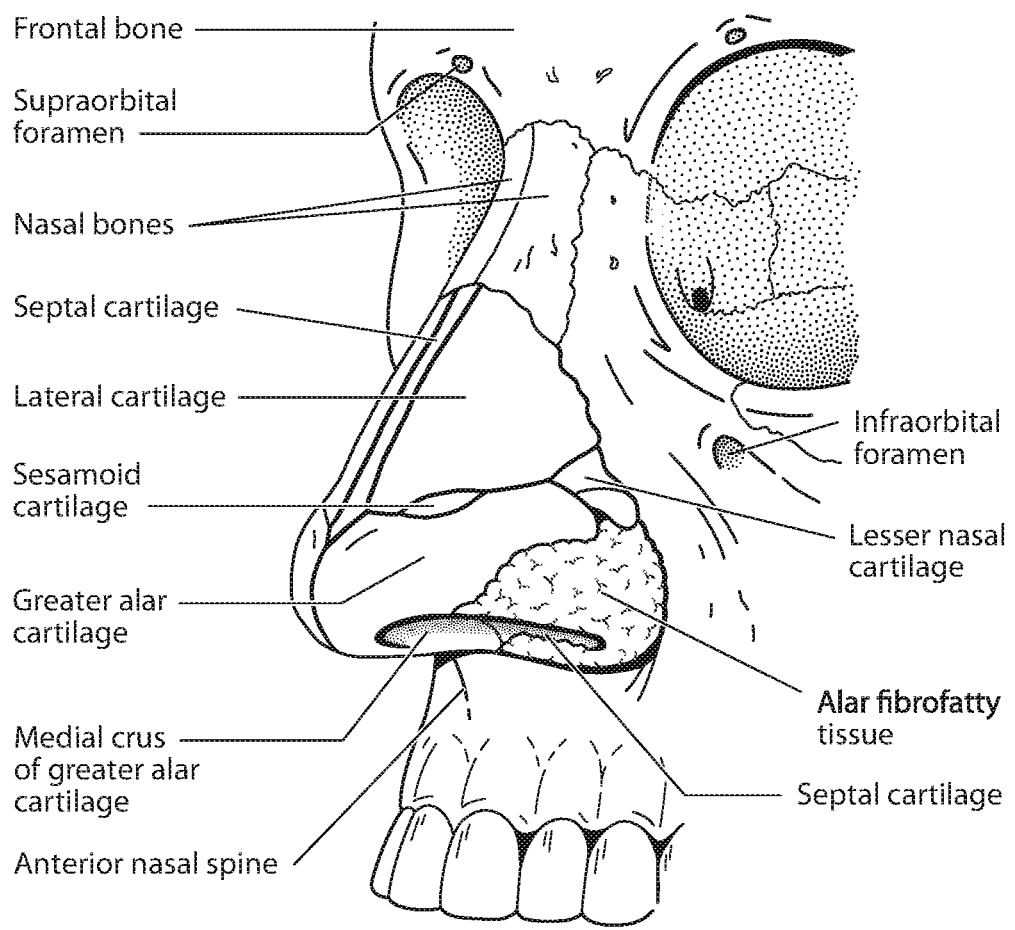

FIG. 2L shows an anterolateral view of a nose.

4.3 Patient Interface

Figure 3:
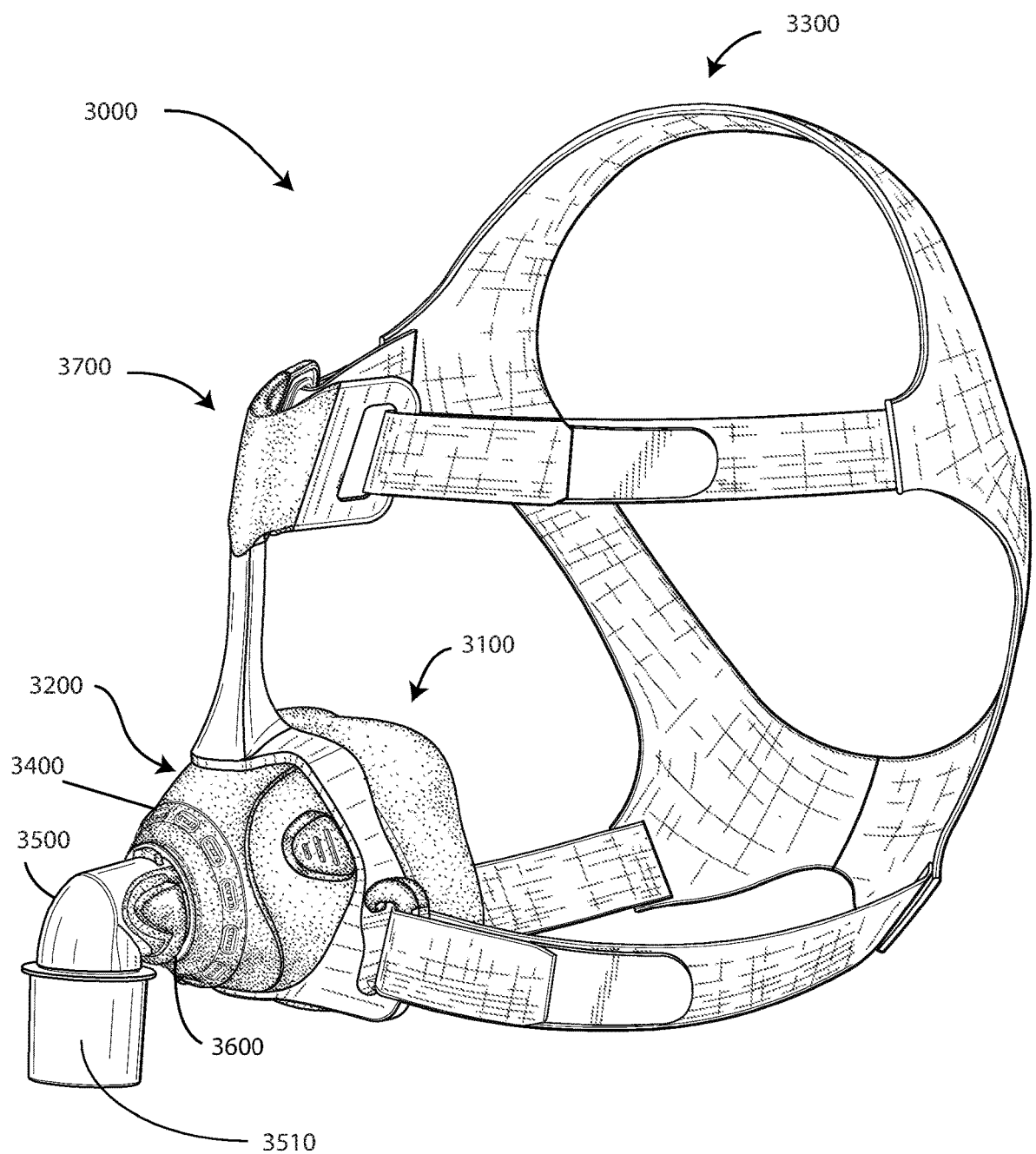

FIG. 3 shows a patient interface in accordance with one form of the present technology.

4.4 RPT Device

Figure 4A:
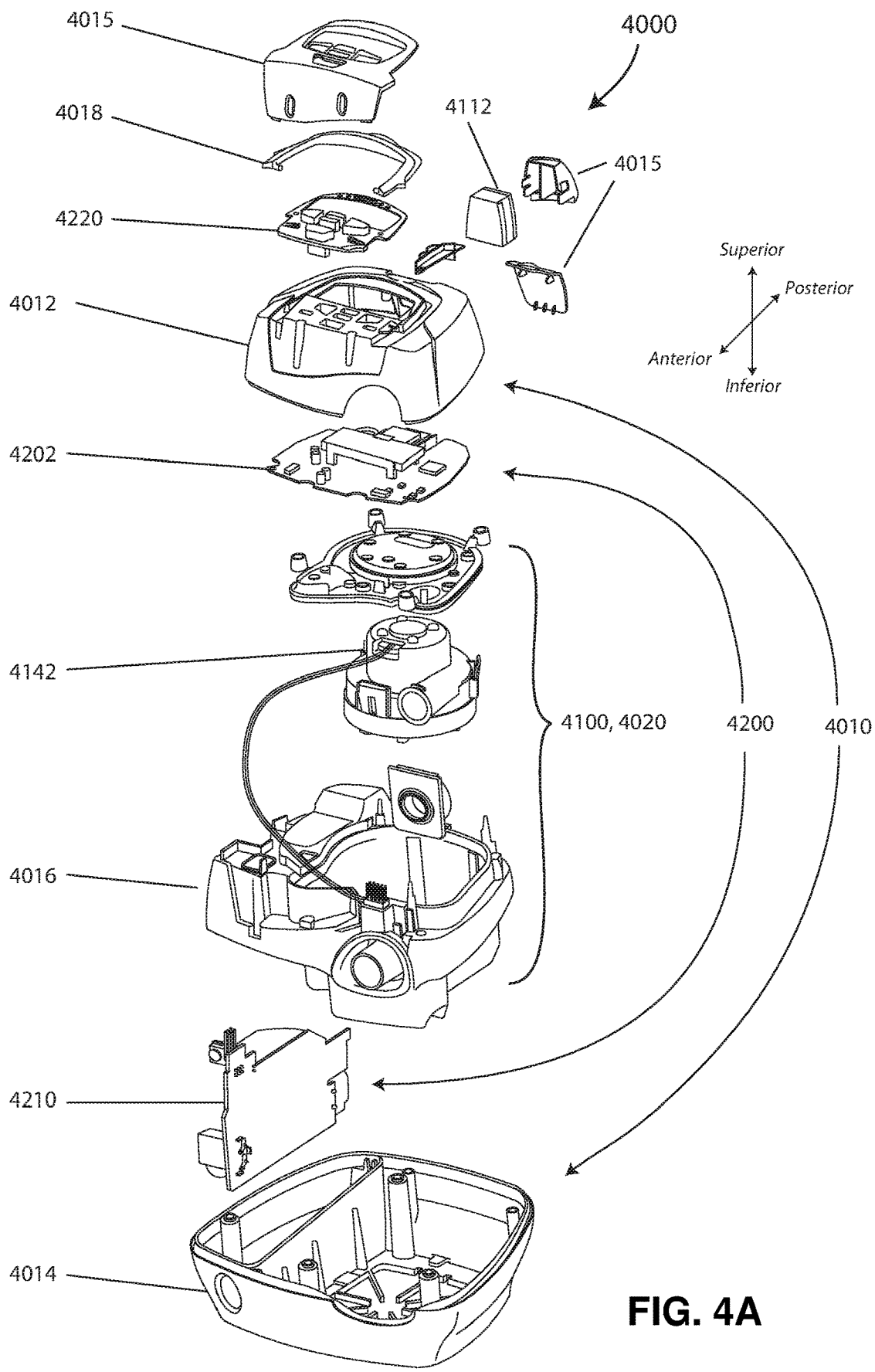

FIG. 4A shows an RPT device in accordance with one form of the present technology.

Figure 4B:
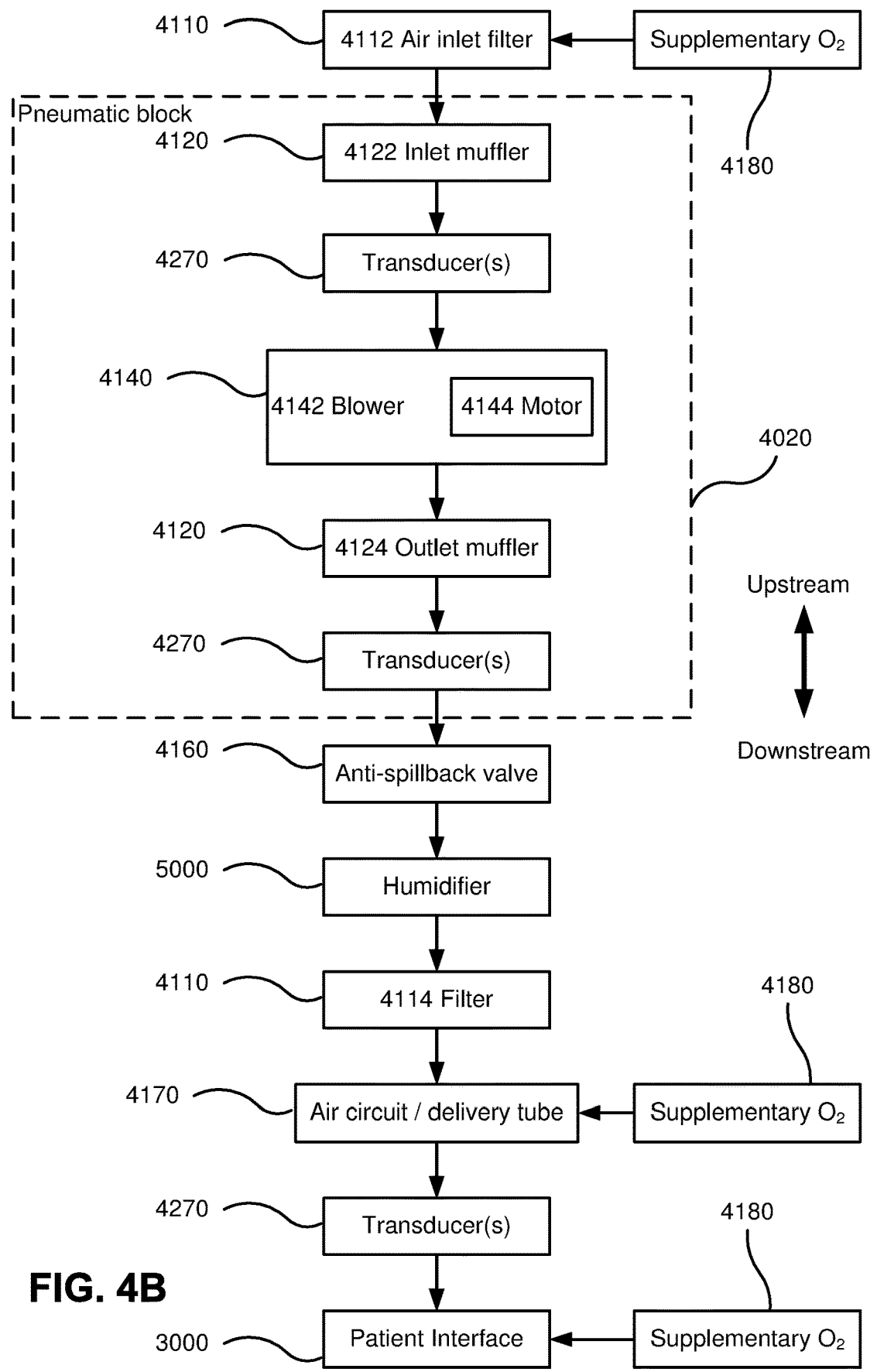

FIG. 4B is a schematic diagram of the pneumatic path of an RPT device in accordance with one form of the present technology. The directions of upstream and downstream are indicated.

Figure 4C:
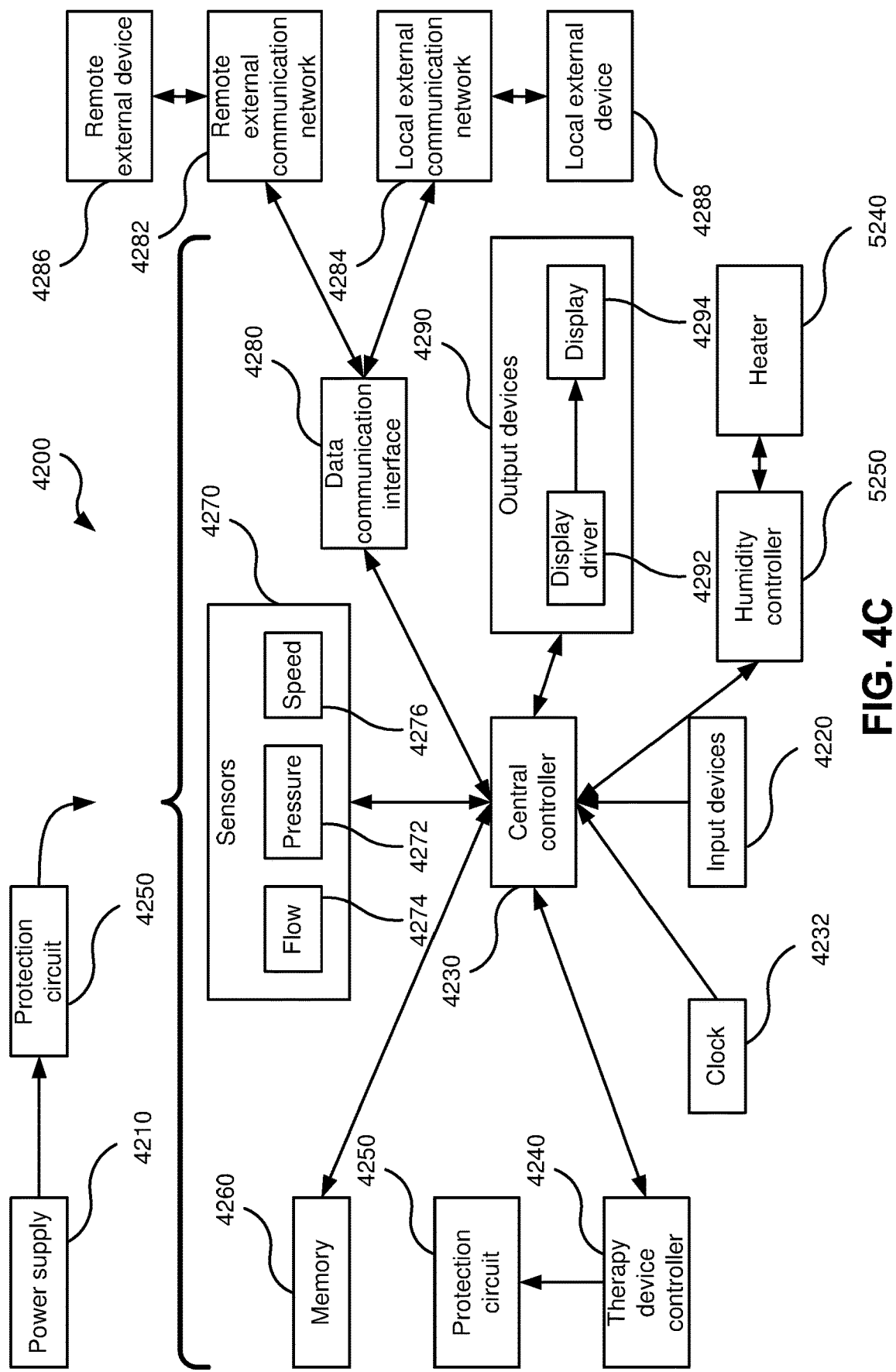

FIG. 4C is a schematic diagram of the electrical components of an RPT device in accordance with one form of the present technology.

Figure 4D:
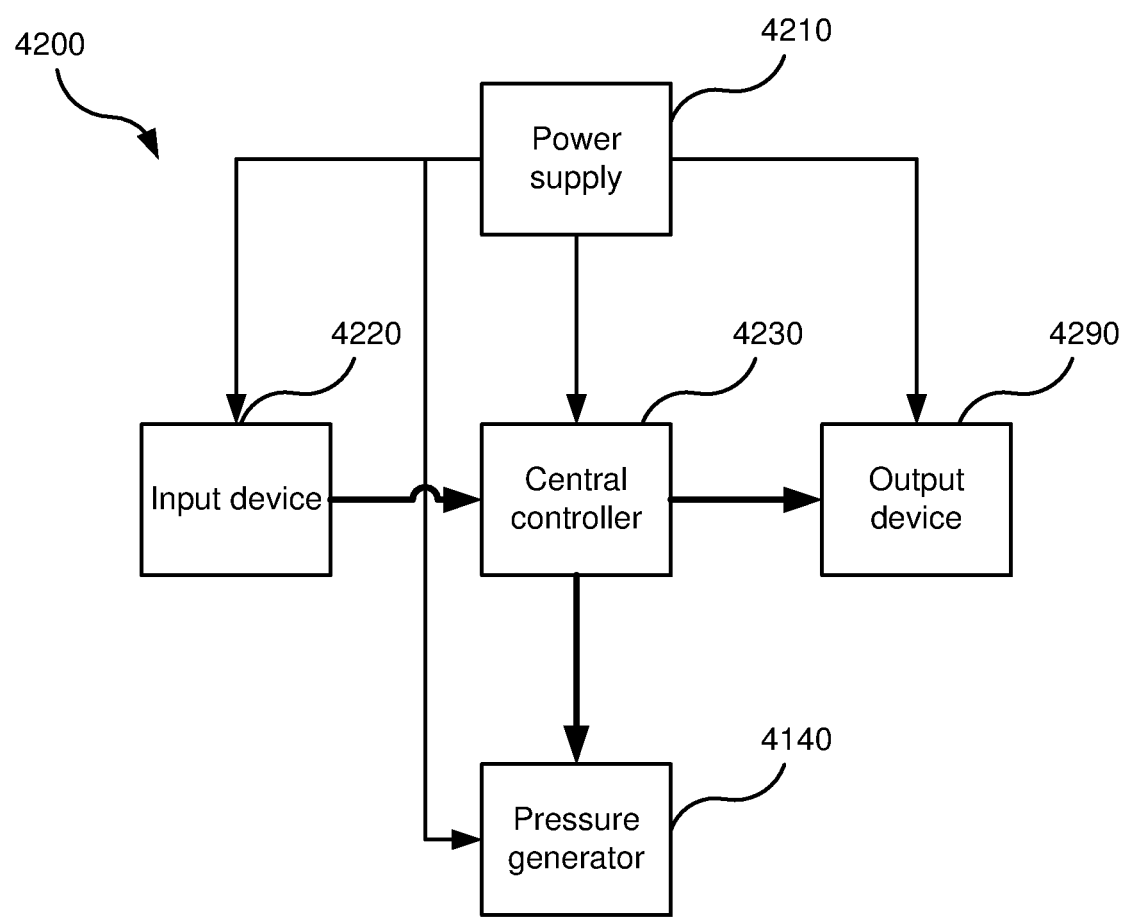

FIG. 4D is another schematic diagram of the electrical components of an RPT device in accordance with one form of the present technology.

4.5 Humidifier

Figure 5A:
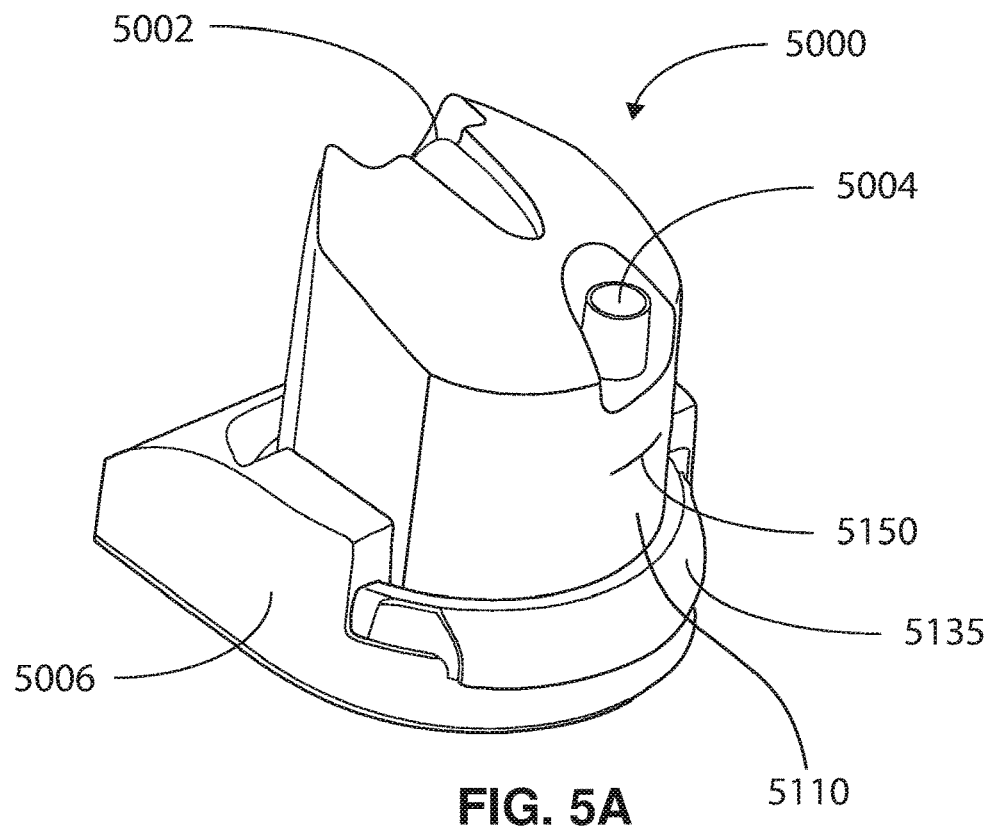

FIG. 5A shows an isometric view of a humidifier in accordance with one form of the present technology.

Figure 5B:
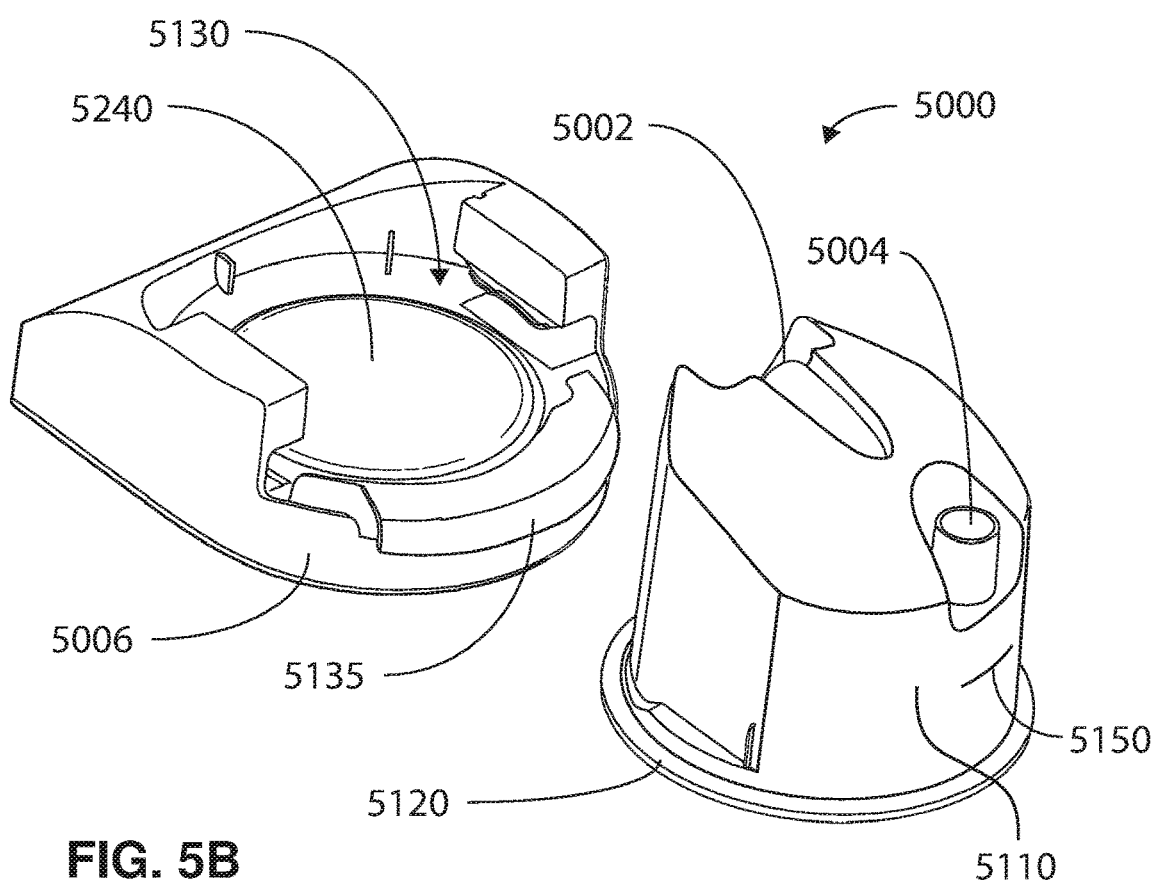

FIG. 5B shows an isometric view of a humidifier in accordance with one form of the present technology, showing a humidifier reservoir 5110 removed from the humidifier reservoir dock 5130.

Figure 5C:
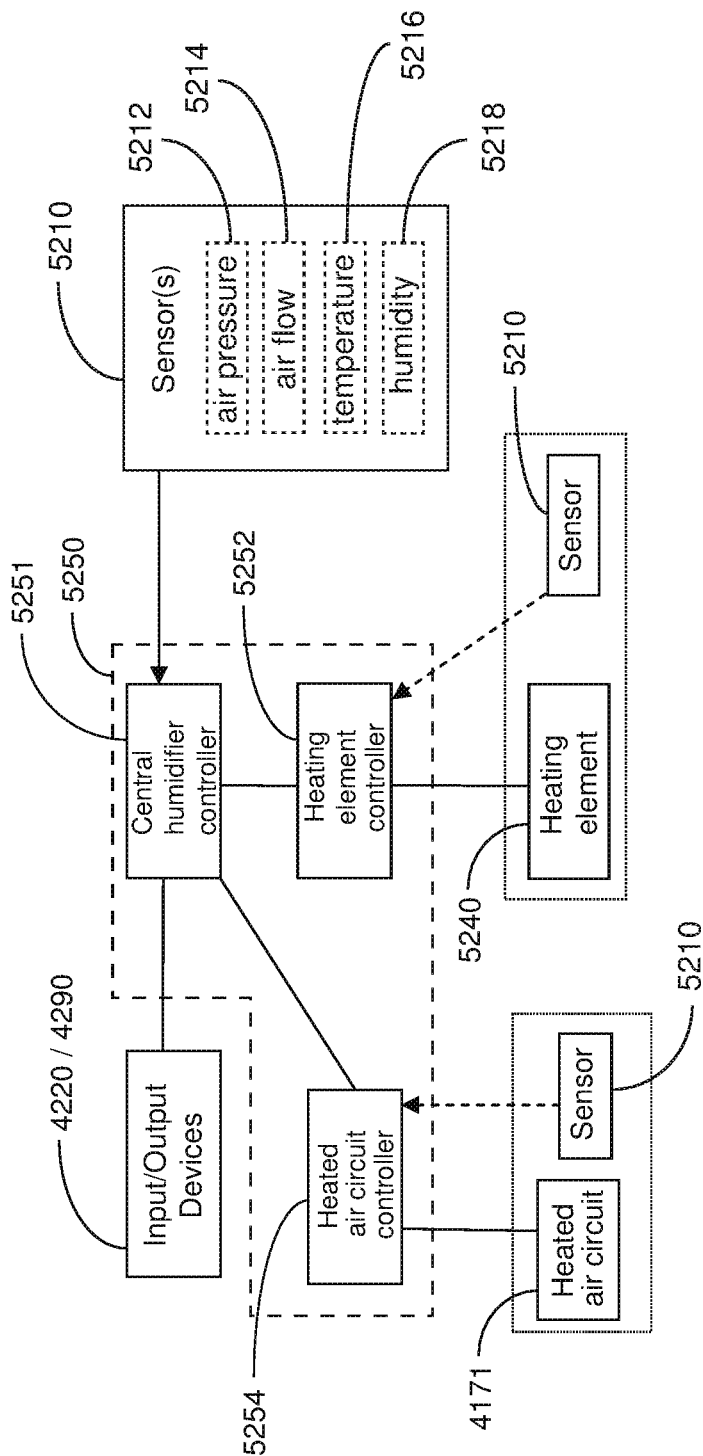

FIG. 5C shows a schematic of a humidifier in accordance with one form of the present technology.

4.6 Breathing Waveforms

Figure 6:
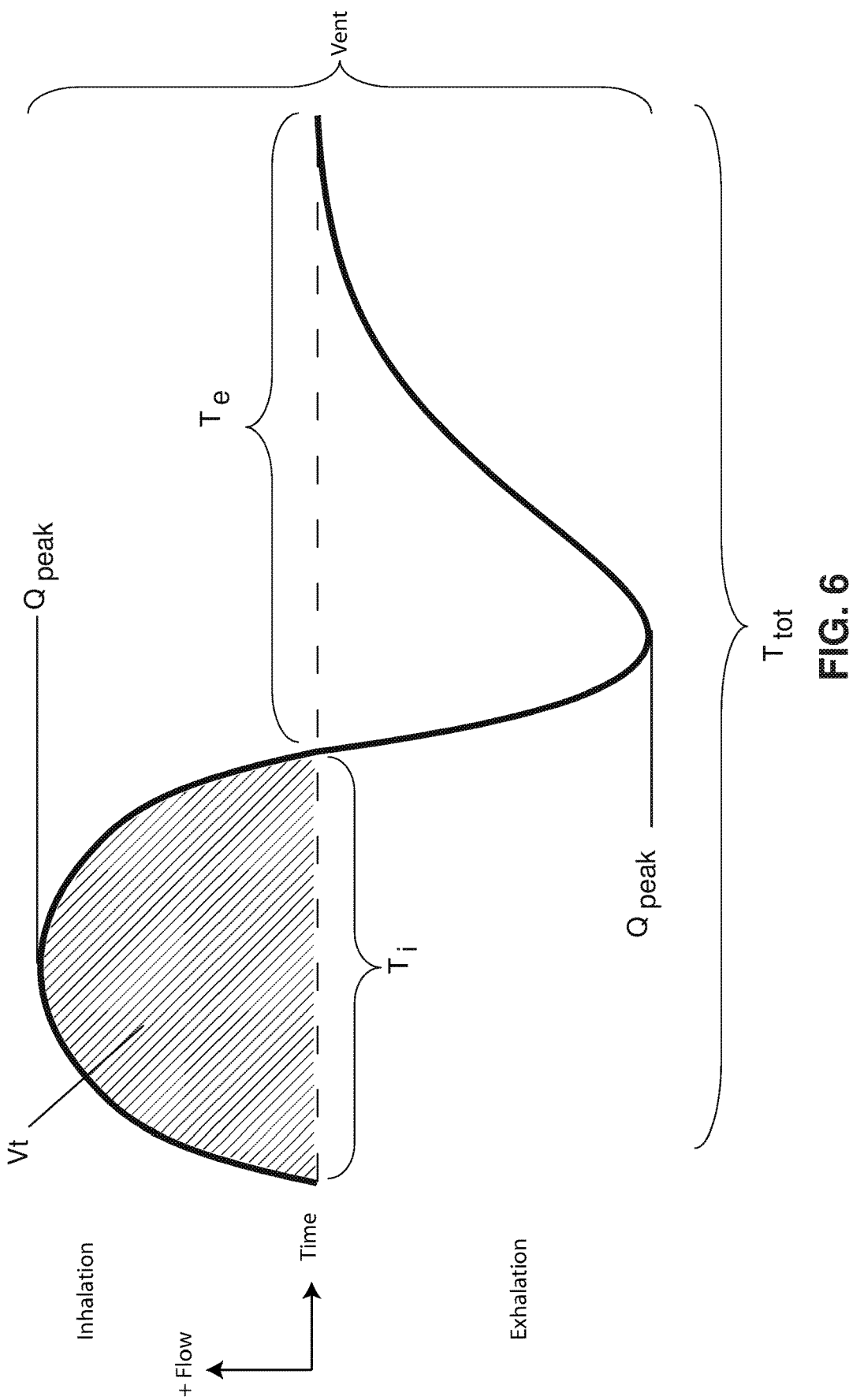

FIG. 6 shows a model typical breath waveform of a person while sleeping.

4.7 Examples of the Present Technology

Figure 7A:
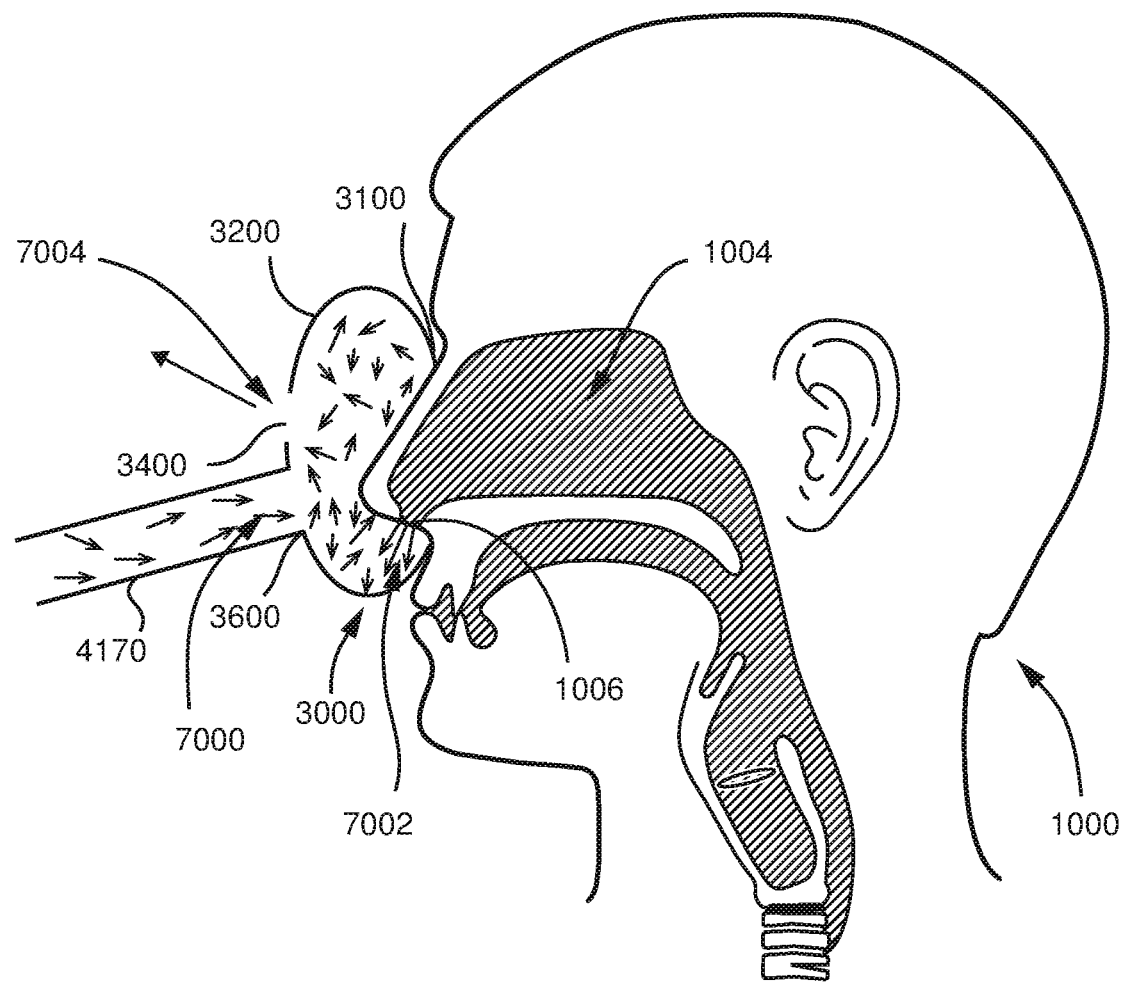

FIG. 7A shows a side view of a patient receiving a flow of pressurized, breathable from a patient interface in accordance with an example of the present technology.

Figure 7B:
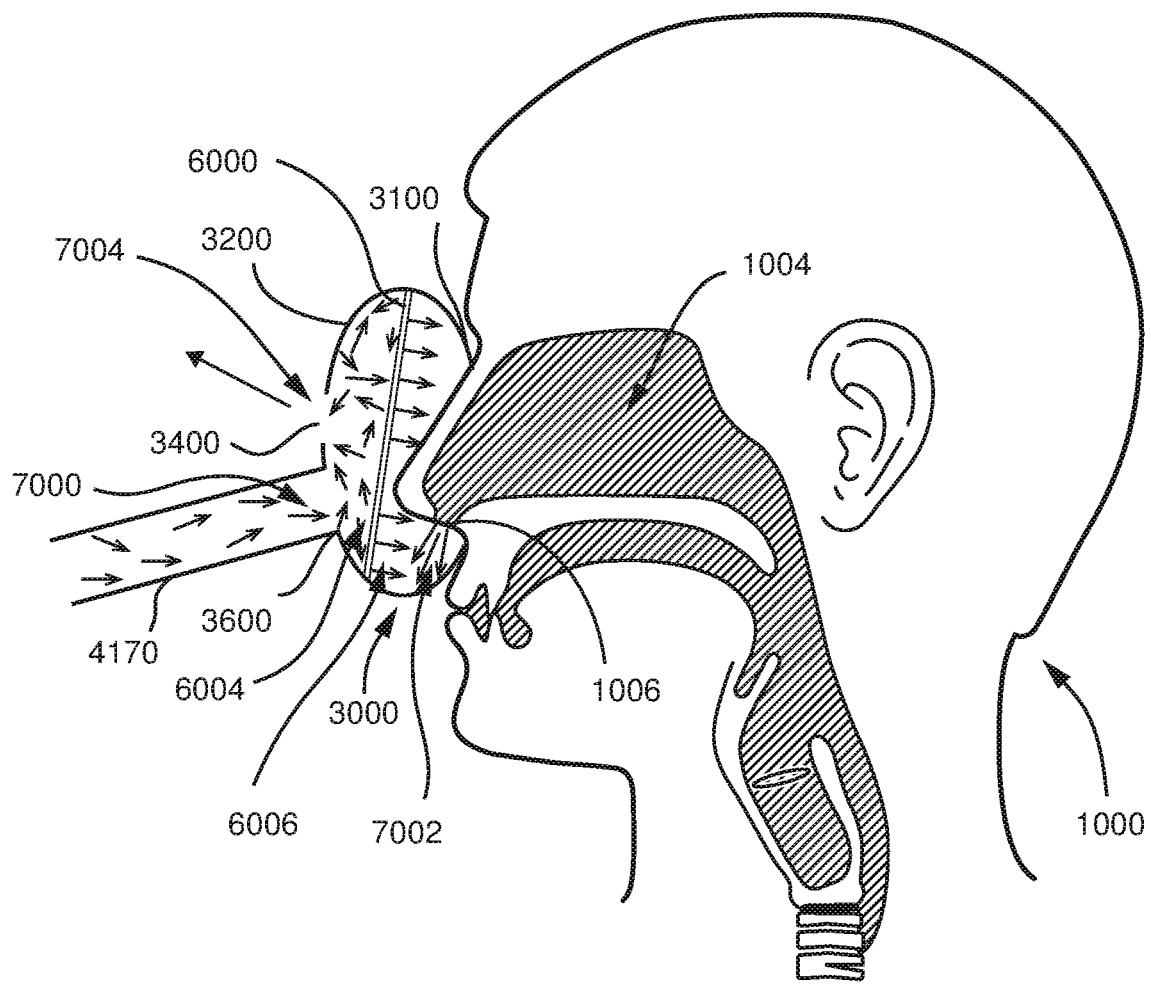

FIG. 7B shows a side view of a patient receiving a flow of pressurized, breathable from a patient interface with a device in accordance with an example of the present technology.

Figure 8A:
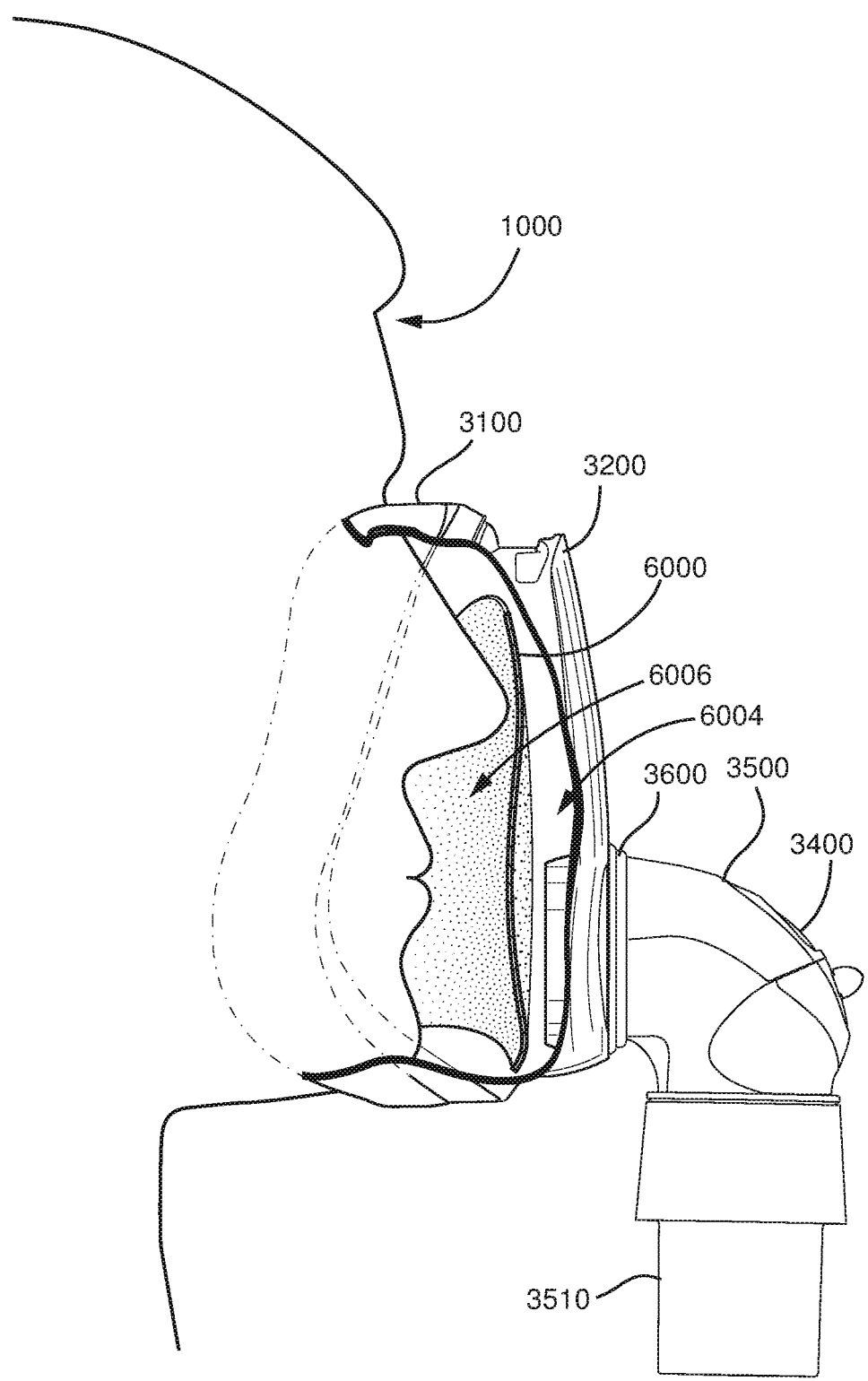

FIG. 8A shows a side view of a patient with a patient interface that includes a device in accordance with an example of the present technology.

Figure 8B:
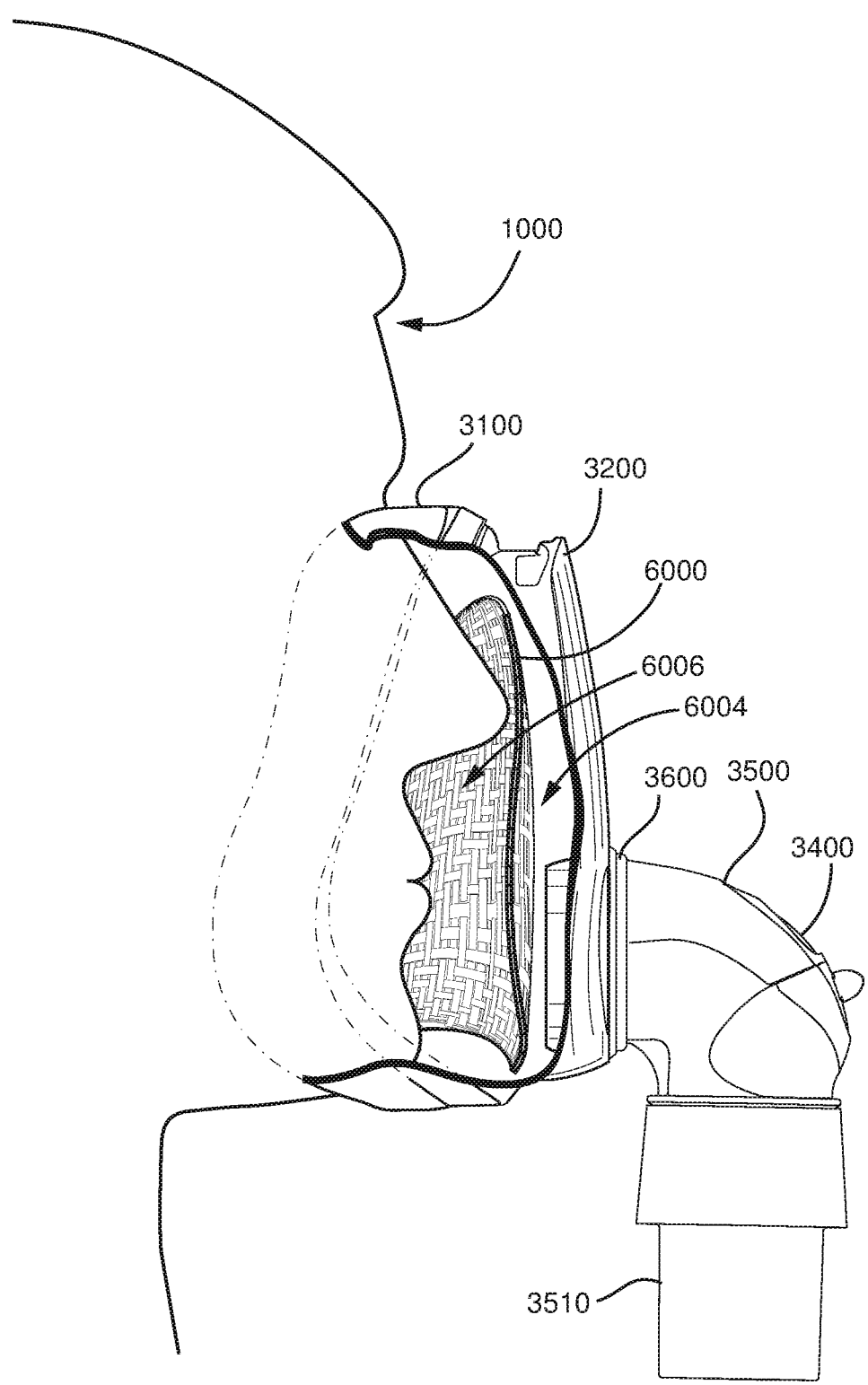

FIG. 8B shows a side view of a patient with a patient interface that includes a device in accordance with an example of the present technology.

Figure 8C:
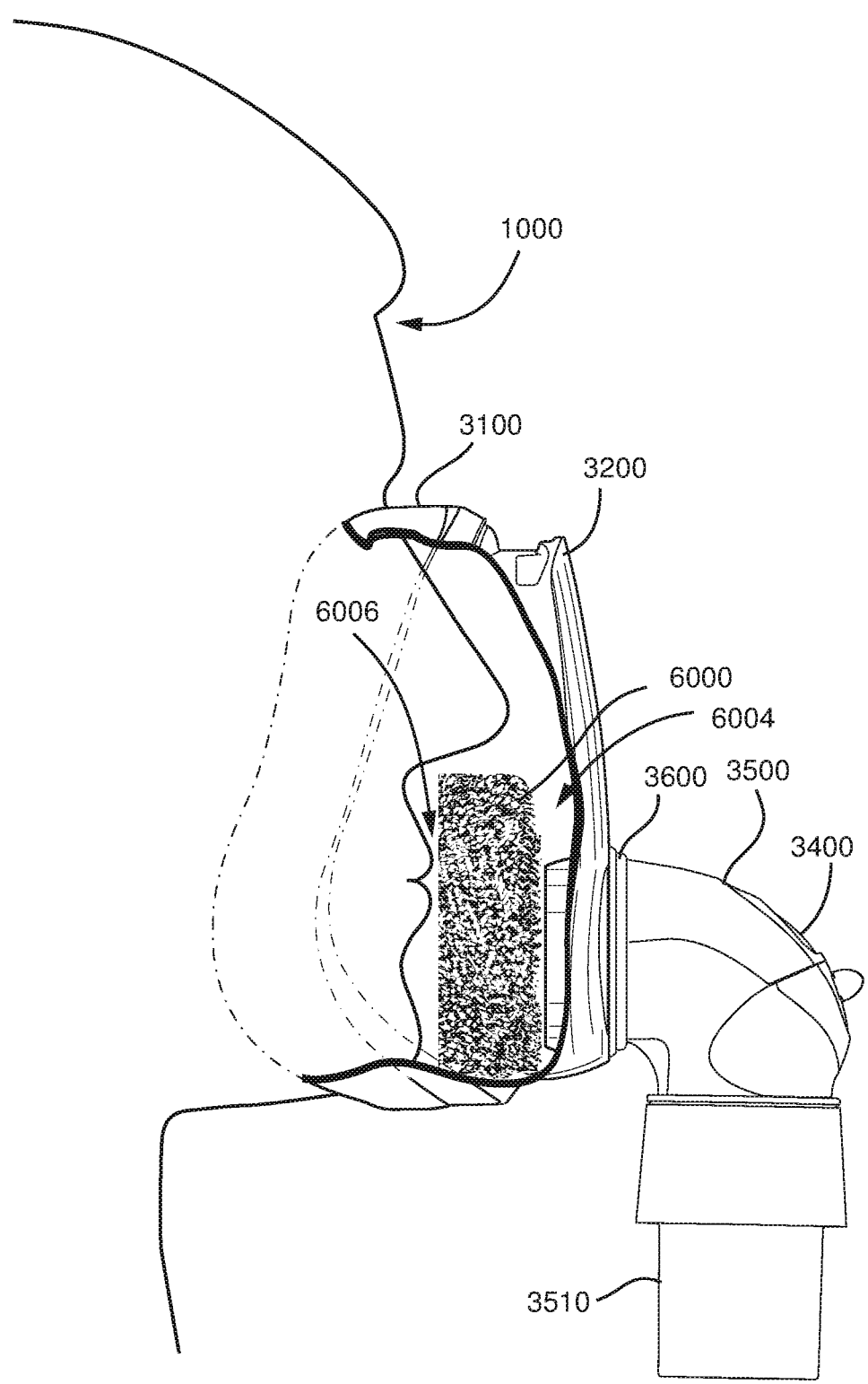

FIG. 8C shows a side view of a patient with a patient interface that includes a device in accordance with an example of the present technology.

Figure 9A:
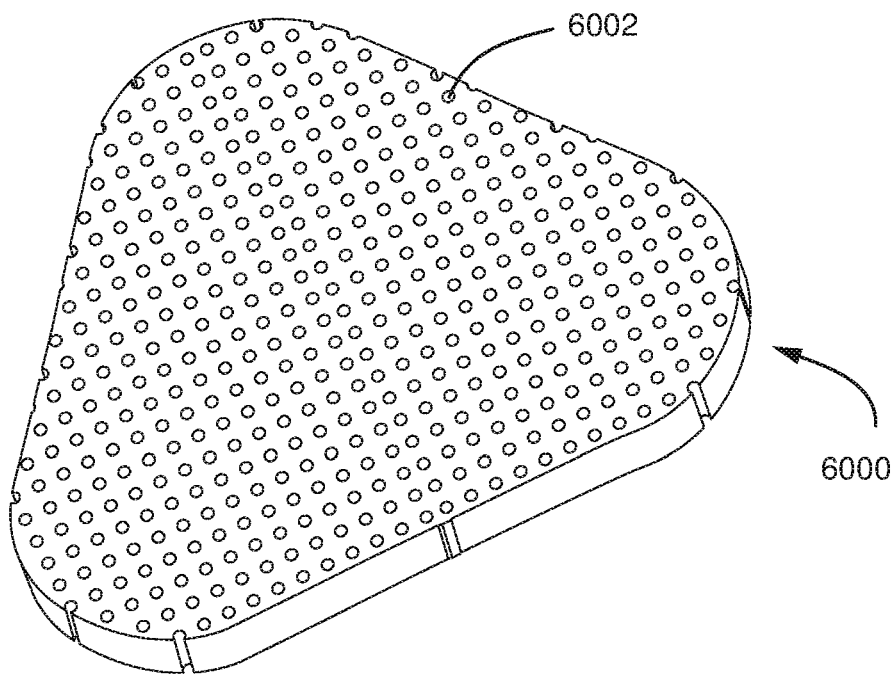

FIG. 9A shows a perspective view of an example of a device in accordance with an example of the present technology.

Figure 9B:
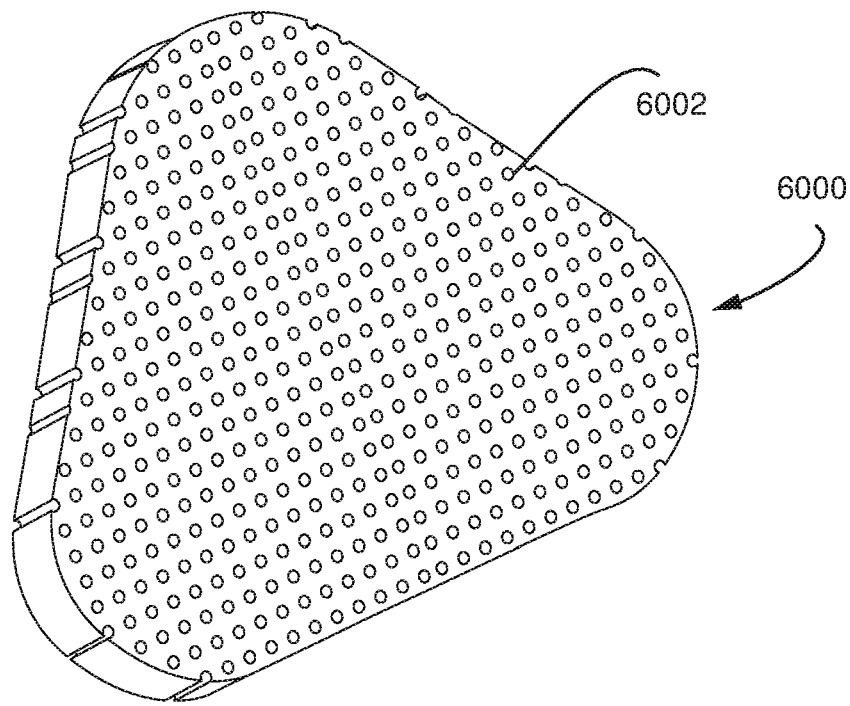

FIG. 9B shows a perspective view of an example of a device in accordance with an example of the present technology.

Figure 10A:
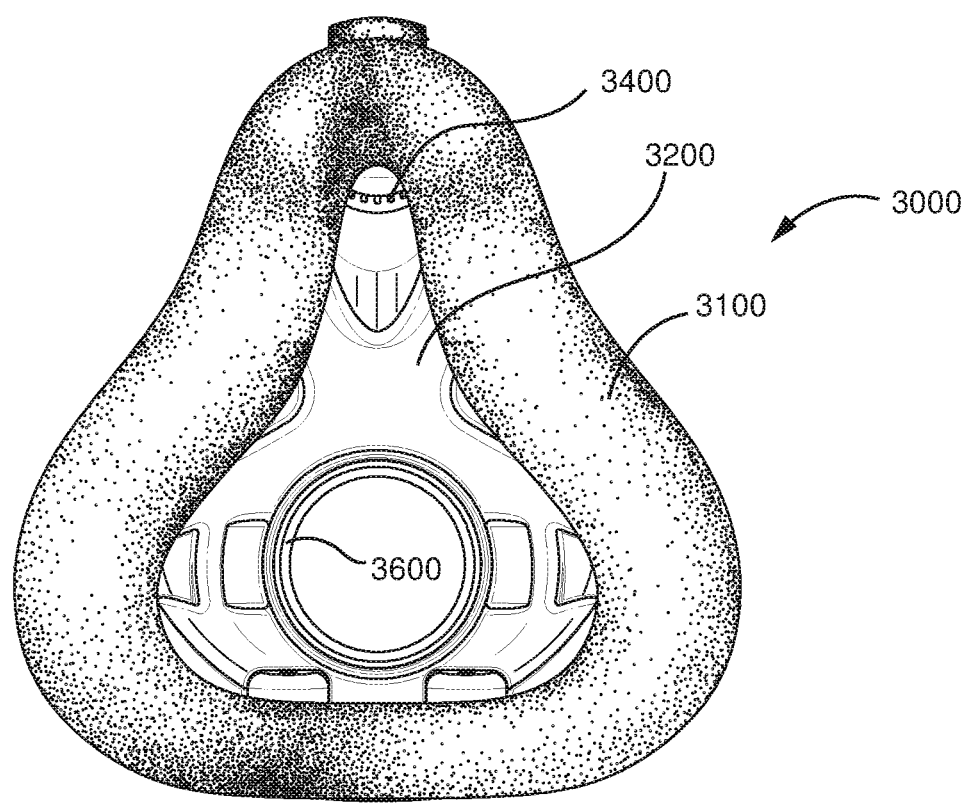

FIG. 10A shows a rear view of a patient with a patient interface in accordance with an example of the present technology.

Figure 10B:
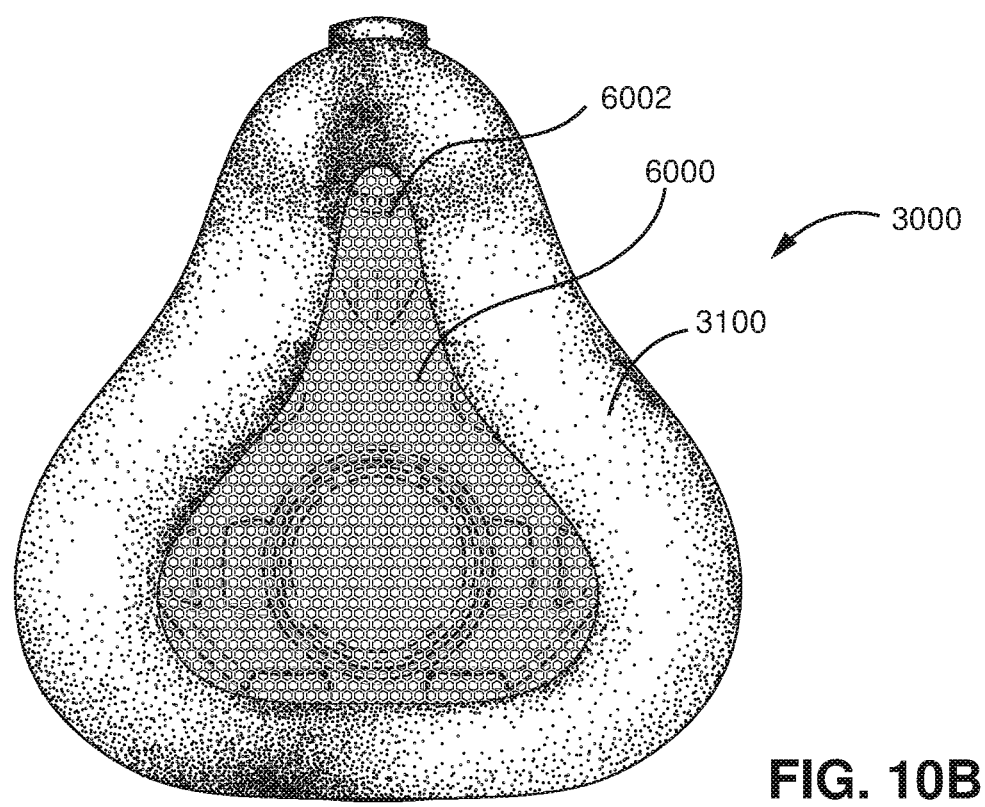

FIG. 10B shows a rear view of a patient with a patient interface that includes a device in accordance with an example of the present technology.

Figure 11:
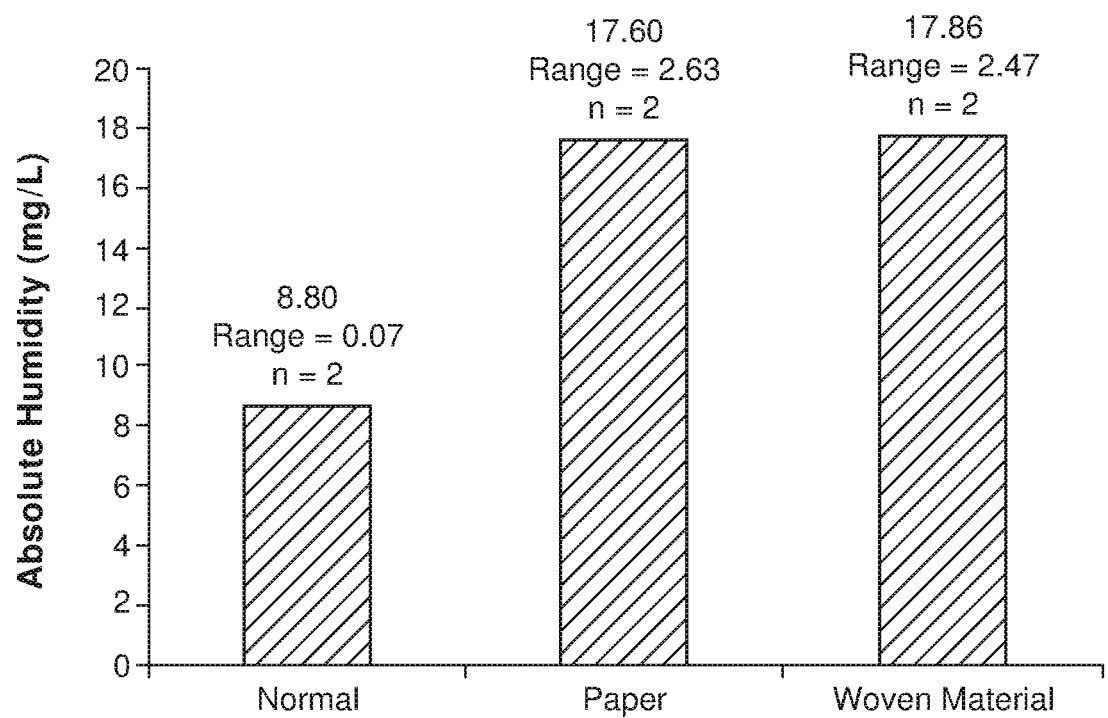

FIG. 11 shows a chart of the average absolute humidity in the posterior side of a device in a patient interface based on different device materials according to an example of the present technology.

Figure 12A:
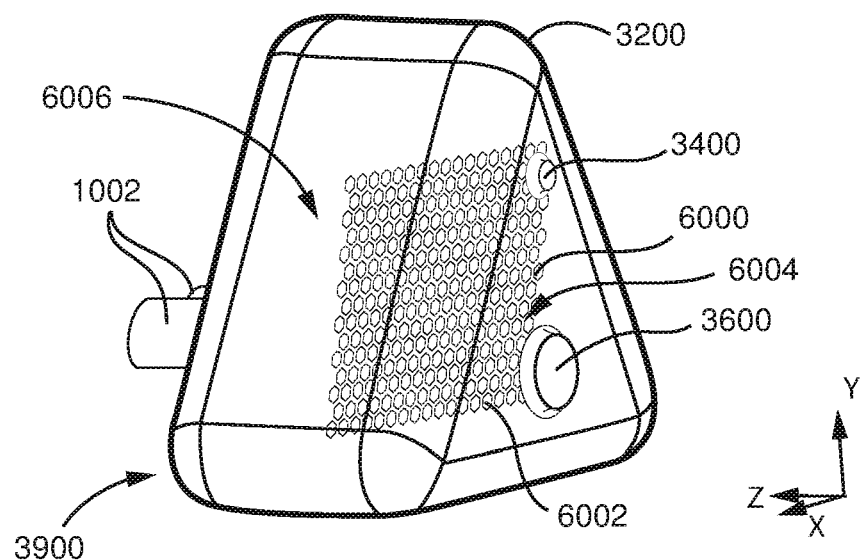

FIG. 12A shows a front perspective view of a model of a seal-forming structure and a plenum chamber of a patient interface with a vent, a connection port, and a device in accordance with an example of the present technology.

Figure 12B:
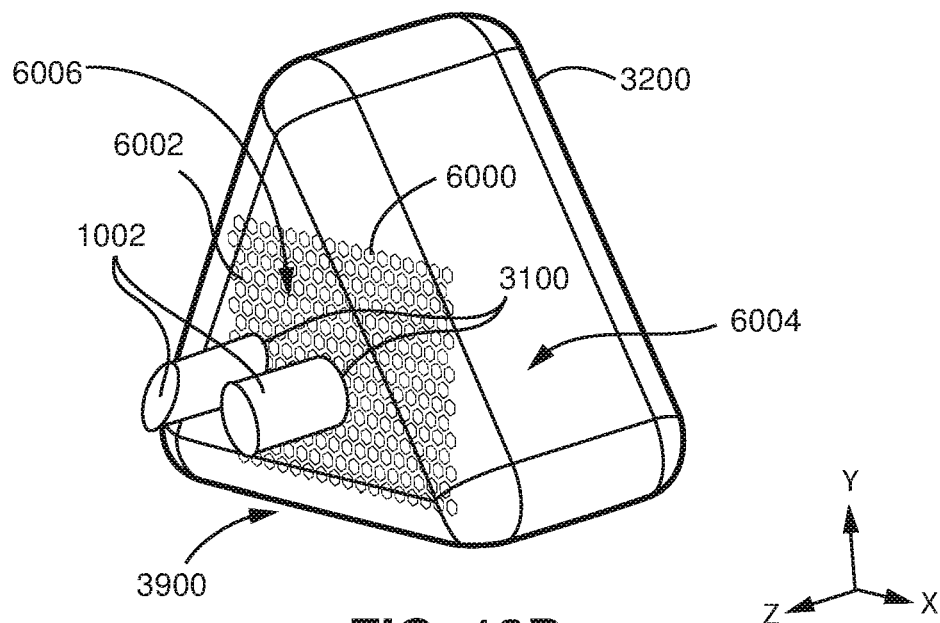

FIG. 12B shows a front perspective view of a model of a seal-forming structure and a plenum chamber of a patient interface with a vent, a connection port, and a device in accordance with an example of the present technology.

Figure 13A:
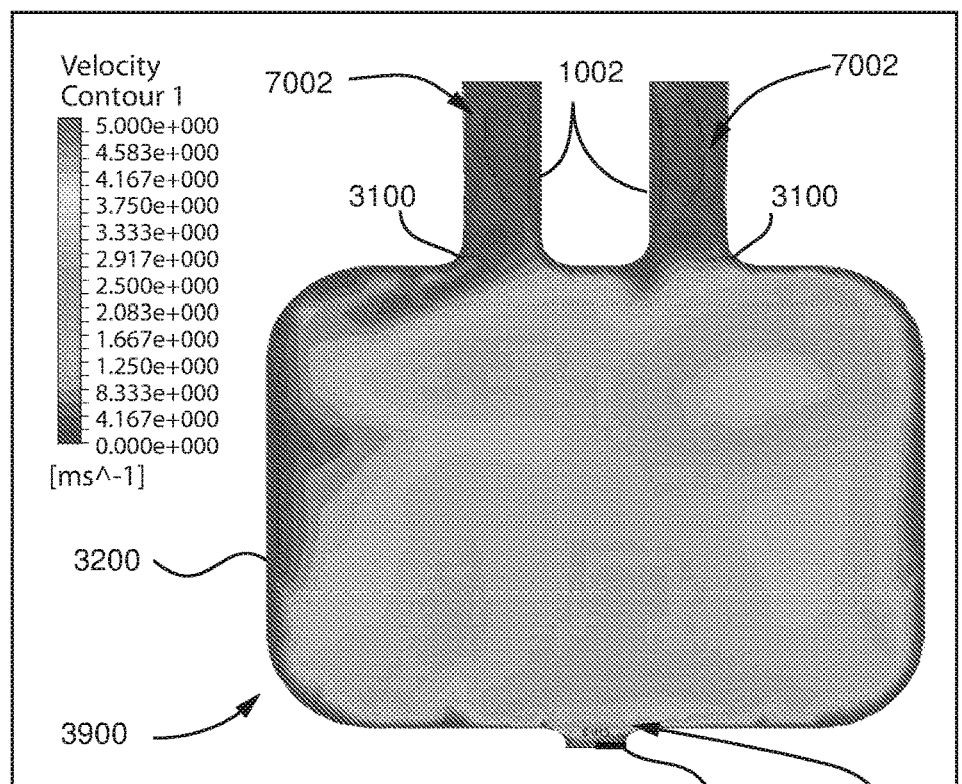

FIG. 13A shows flow velocity modelling within the model of FIGS. 12A and 12B (the device is absent) from a computational fluid dynamics program when flow produced by the patient is zero.

Figure 13B:
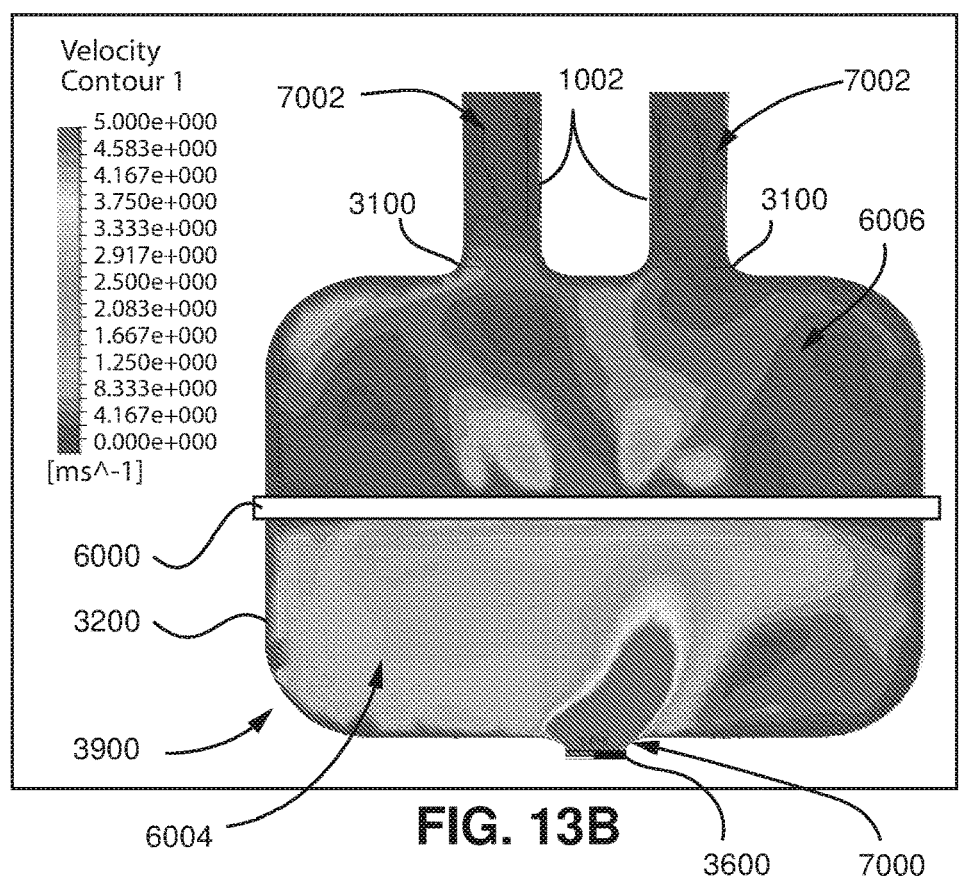

FIG. 13B shows flow velocity modelling within the model of FIGS. 12A and 12B (the device is present) from a computational fluid dynamics program when flow produced by the patient is zero.

Figure 14A:
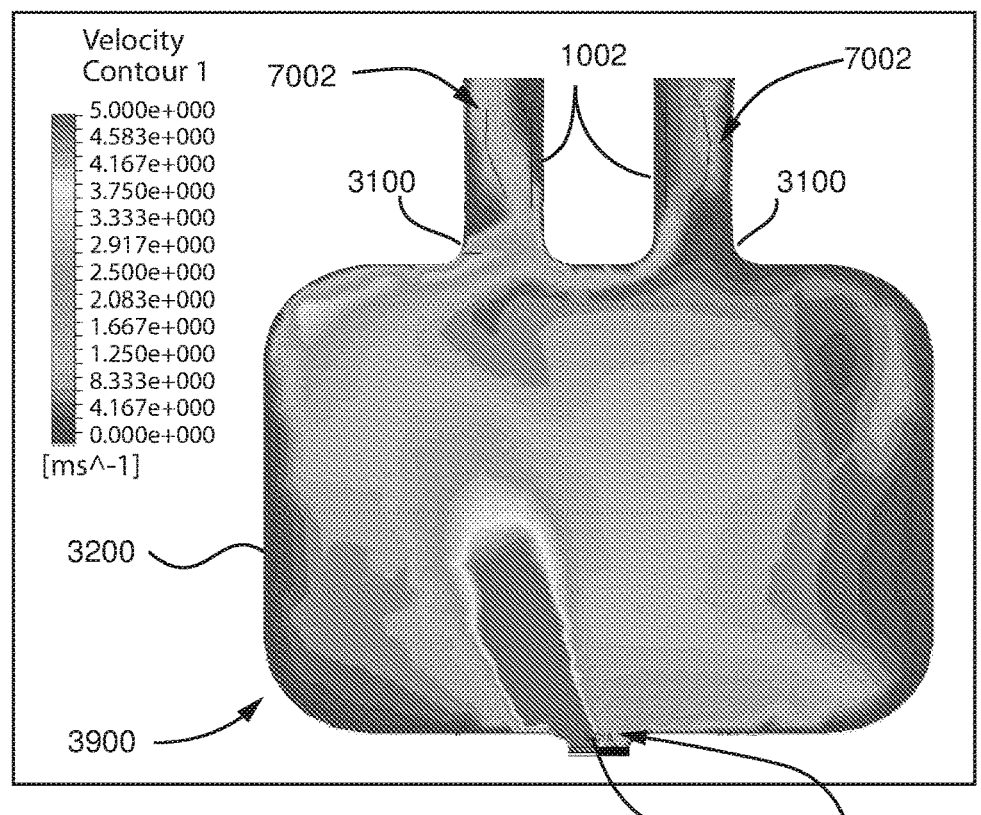

FIG. 14A shows flow velocity modelling within the model of FIGS. 12A and 12B (the device is absent) from a computational fluid dynamics program when flow produced by the patient is 10 L/min.

Figure 14B:
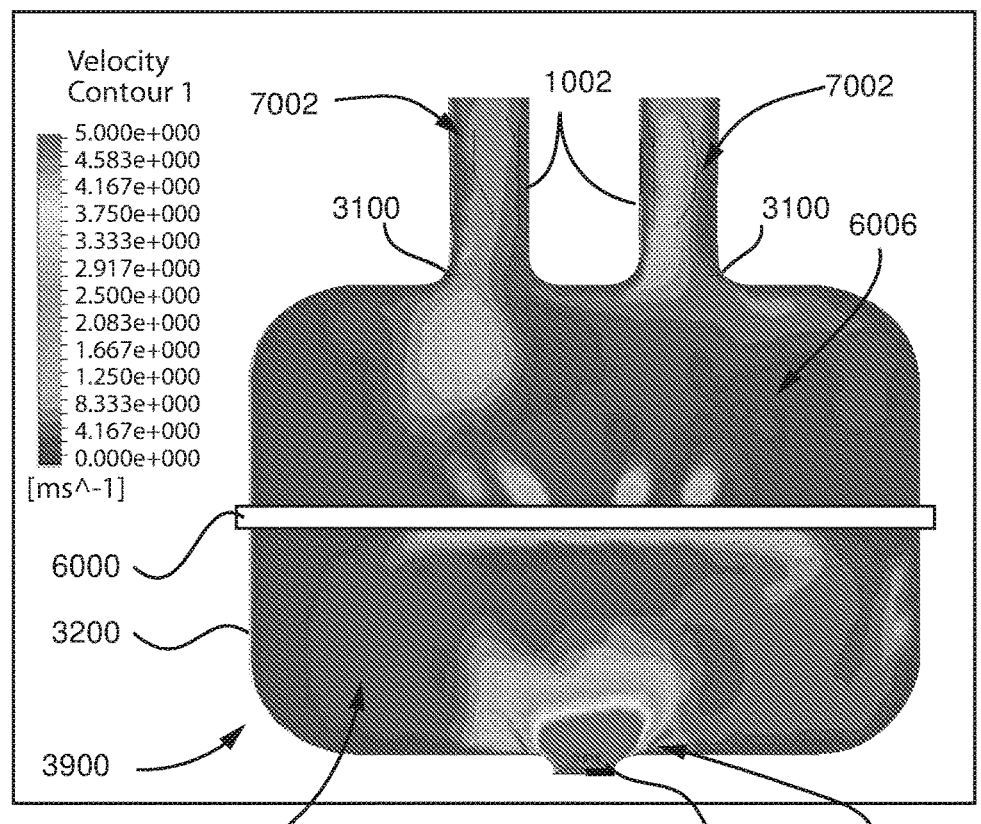

FIG. 14B shows flow velocity modelling within the model of FIGS. 12A and 12B (the device is present) from a computational fluid dynamics program when flow produced by the patient is 10 L/min.

Figure 15A:
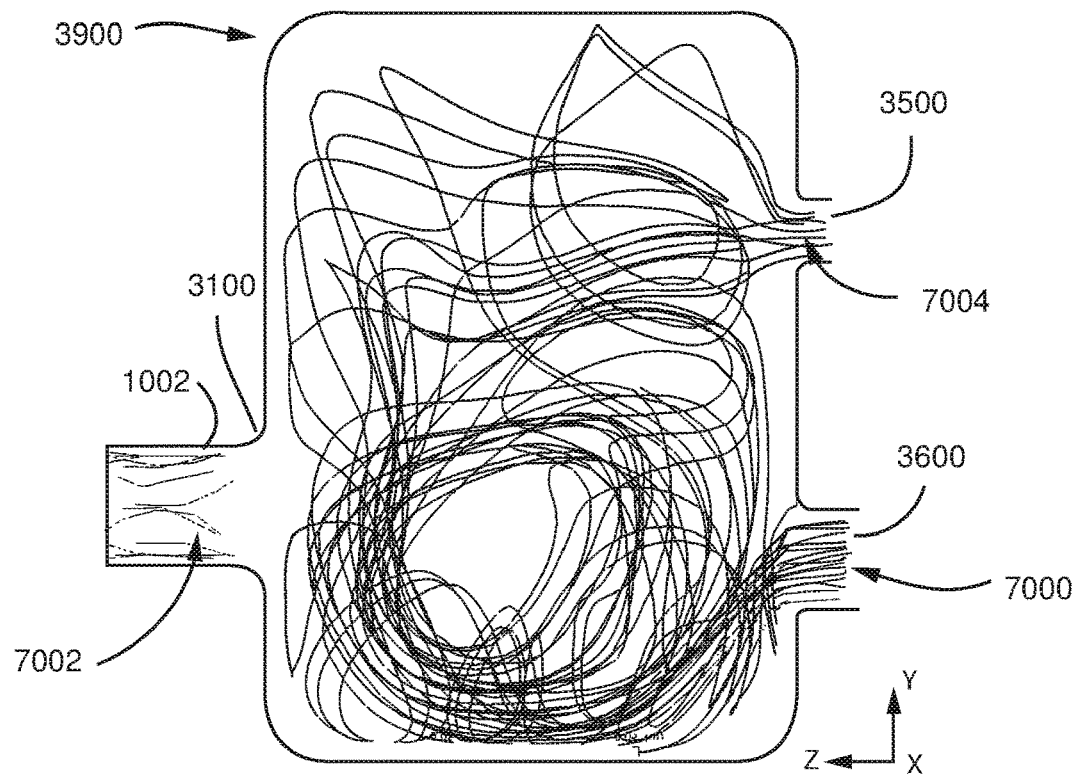

FIG. 15A shows flow velocity streamlines modelled within the model of FIGS. 12A and 12B (the device is absent) from a computational fluid dynamics program when flow produced by the patient is zero.

Figure 15B:
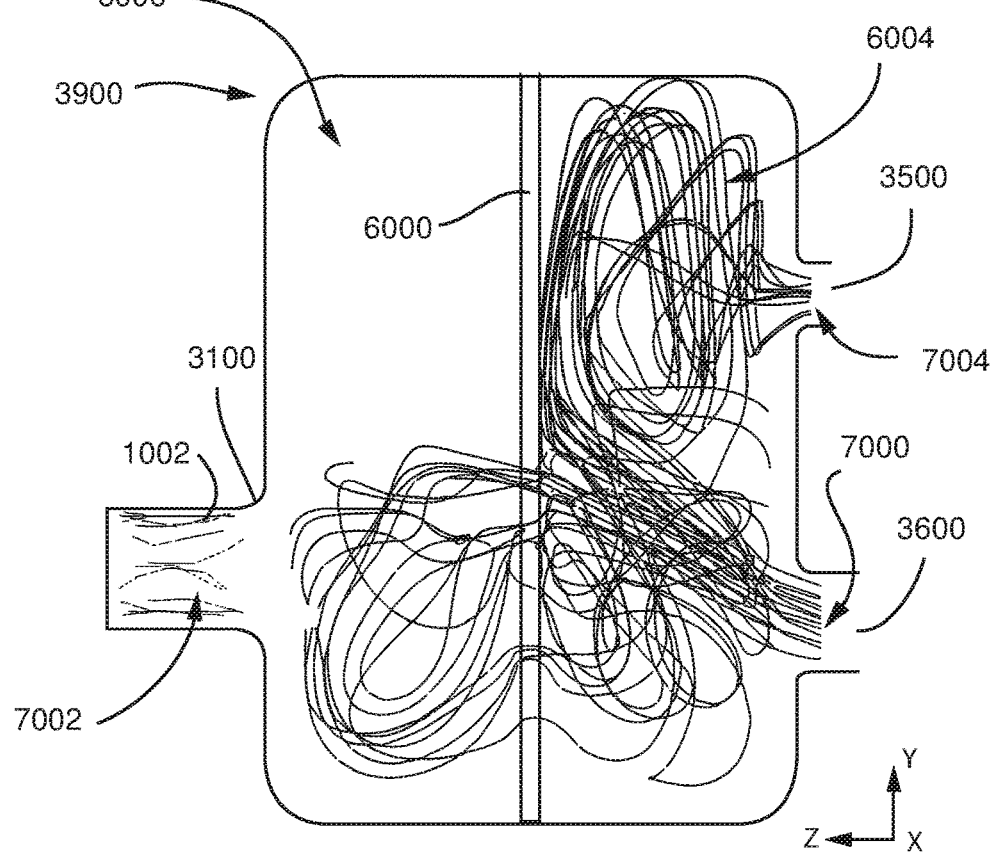

FIG. 15B shows flow velocity streamlines modelled within the model of FIGS. 12A and 12B (the device is present) from a computational fluid dynamics program when flow produced by the patient is zero.

Figure 16A:
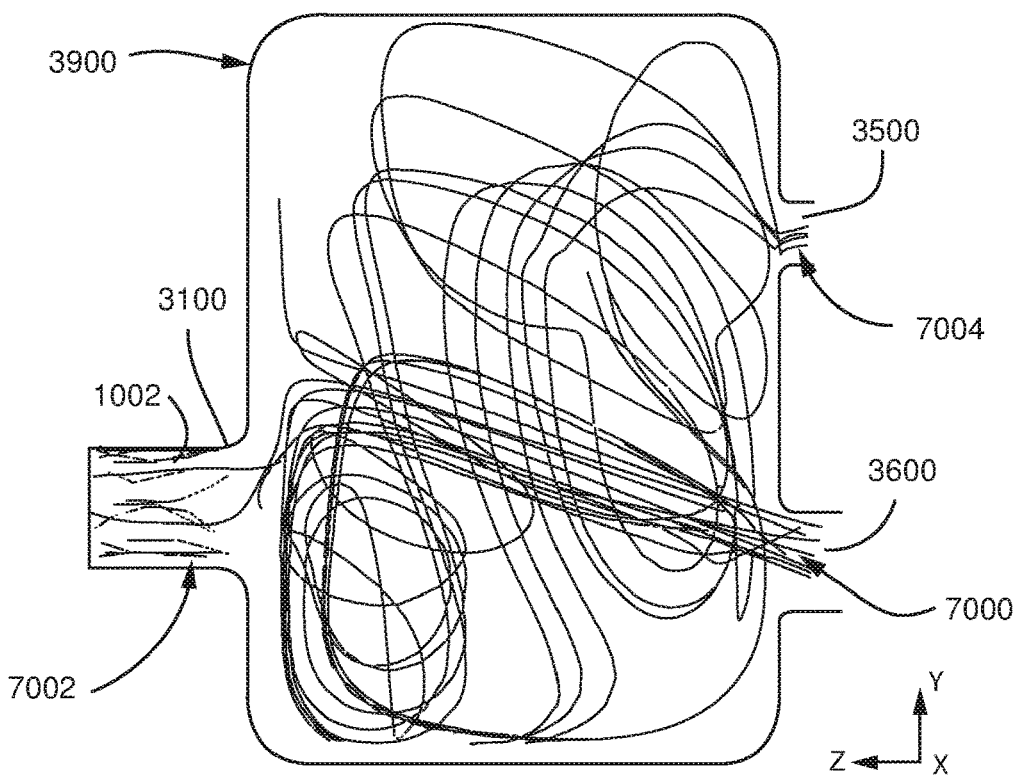

FIG. 16A shows flow velocity streamlines modelled within the model of FIGS. 12A and 12B (the device is absent) from a computational fluid dynamics program when flow produced by the patient is 10 L/min.

Figure 16B:
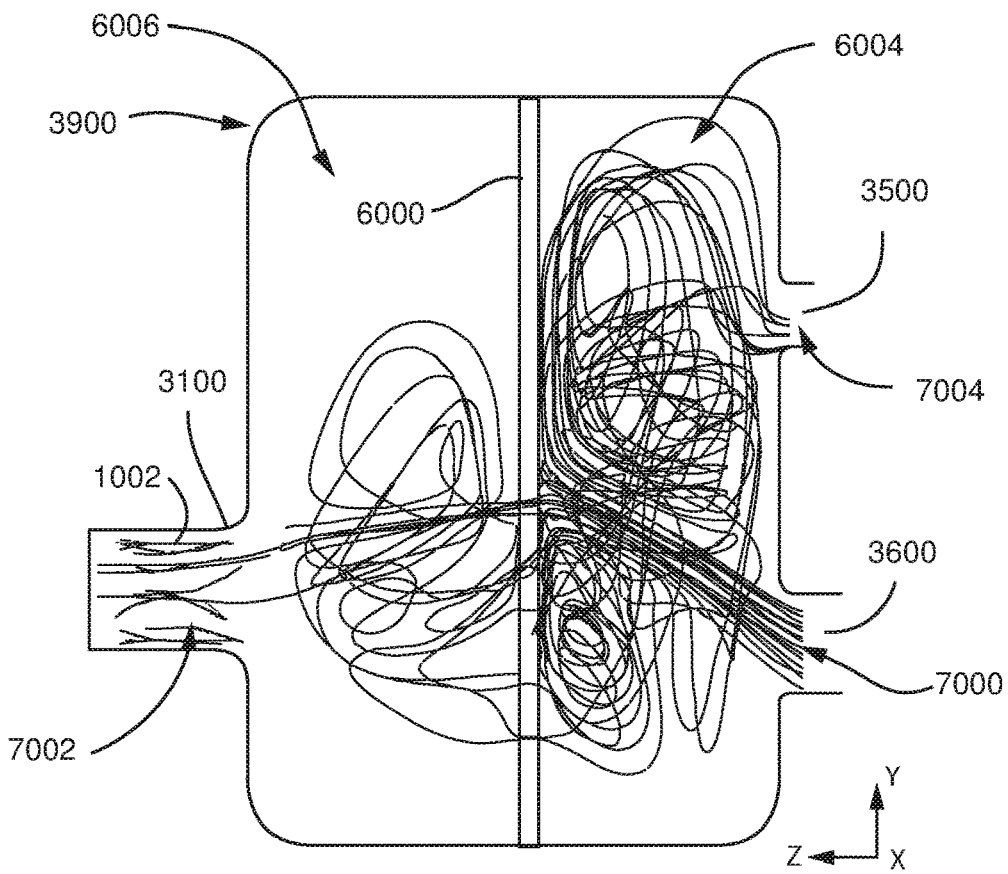

FIG. 16B shows flow velocity streamlines modelled within the model of FIGS. 12A and 12B (the device is present) from a computational fluid dynamics program when flow produced by the patient is 10 L/min.

DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5 DETAILED DESCRIPTION OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Treatment Systems

In one form, the present technology comprises an apparatus or device for treating a respiratory disorder. The apparatus or device may comprise an RPT device 4000 for supplying pressurised air to the patient 1000 via an air circuit 4170 to a patient interface 3000.

5.3 Patient Interface

A non-invasive patient interface 3000 in accordance with one aspect of the present technology comprises the following functional aspects: a seal-forming structure 3100, a plenum chamber 3200, a positioning and stabilising structure 3300 and one form of connection port 3600 for connection to air circuit 4170. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

5.3.1 Seal-Forming Structure

In one form of the present technology, a seal-forming structure 3100 provides a seal-forming surface, and may additionally provide a cushioning function.

A seal-forming structure 3100 in accordance with the present technology may be constructed from a soft, flexible, resilient material such as silicone.

In one form, the seal-forming structure comprises a sealing flange and a support flange. Support flange may be relatively thicker than the sealing flange. The support flange is disposed between the sealing flange and the marginal edge of the plenum chamber 3200, and extends at least part of the way around the perimeter. The support flange is or includes a spring-like element and functions to support the sealing flange 3110 from buckling in use. In use the sealing flange 3110 can readily respond to system pressure in the plenum chamber 3200 acting on its underside to urge it into tight sealing engagement with the face.

In one form the seal-forming portion of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

In one form, the non-invasive patient interface 3000 comprises a seal-forming portion that forms a seal in use on an upper lip region (that is, the lip superior) of the patient's face.

In one form the non-invasive patient interface 3000 comprises a seal-forming portion that forms a seal in use on a chin-region of the patient's face.

5.3.2 Plenum Chamber

The plenum chamber 3200 has a perimeter that is shaped to be complementary to the surface contour of the face of an average person in the region where a seal will form in use. In use, a marginal edge of the plenum chamber is positioned in close proximity to an adjacent surface of the face. Actual contact with the face is provided by the seal-forming structure 3100. The seal-forming structure 3100 may extend in use about the entire perimeter of the plenum chamber 3200.

5.3.3 Positioning and Stabilising Structure 3300

The seal-forming portion 3100 of the patient interface 3000 of the present technology may be held in sealing position in use by the positioning and stabilising structure 3300.

In one form of the present technology, a positioning and stabilising structure 3300 is provided that is configured in a manner consistent with being worn by a patient while sleeping. In one example the positioning and stabilising structure 3300 has a low profile, or cross-sectional thickness, to reduce the perceived or actual bulk of the apparatus. In one example, the positioning and stabilising structure 3300 comprises at least one strap having a rectangular cross-section. In one example the positioning and stabilising structure 3300 comprises at least one flat strap.

In one form of the present technology, a positioning and stabilising structure 3300 comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material to engage with a hook material portion.

In certain forms of the present technology, a positioning and stabilising structure 3300 comprises a strap that is extensible, e.g. resiliently extensible. For example the strap may be configured in use to be in tension, and to direct a force to draw a cushion into sealing contact with a portion of a patient's face. In an example the strap may be configured as a tie.

In certain forms of the present technology, a positioning and stabilising structure 3300 comprises a strap that is bendable and e.g. non-rigid. An advantage of this aspect is that the strap is more comfortable for a patient to lie upon while the patient is sleeping.

5.3.4 Vent

In one form, the patient interface 3000 includes a vent 3400 constructed and arranged to allow for the washout of exhaled carbon dioxide.

One form of vent 3400 in accordance with the present technology comprises a plurality of holes, for example, about 20 to about 80 holes, or about 40 to about 60 holes, or about 45 to about 55 holes.

The vent 3400 may be located in the plenum chamber 3200. Alternatively, the vent 3400 is located in a decoupling structure 3500, e.g., a swivel 3510.

5.3.5 Decoupling Structure(s)

In one form the patient interface 3000 includes at least one decoupling structure 3500, for example, a swivel 3510 or a ball and socket.

5.3.6 Connection Port

Connection port 3600 allows for connection to the air circuit 4170.

5.3.7 Forehead Support

In one form, the patient interface 3000 includes a forehead support 3700.

5.3.8 Anti-Asphyxia Valve

In one form, the patient interface 3000 includes an anti-asphyxia valve.

5.3.9 Ports

In one form of the present technology, a patient interface 3000 includes one or more ports that allow access to the volume within the plenum chamber 3200. In one form this allows a clinician to supply supplemental oxygen. In one form, this allows for the direct measurement of a property of gases within the plenum chamber 3200, such as the pressure.

5.3.10 Patient Interface 3000 Comprising a Device 6000

In related technologies, the patient 1000 may be provided a supply of gas generated by an RPT device 4000, as described elsewhere herein. The patient interface 3000 of these related technologies may include a vent 3400 to allow for the washout or discharge of expired gas from the patient 1000 to direct $CO_2$ away from the patient's airways 1004, thereby preventing the patient 1000 from inhaling gas with an undesirably high concentration of $CO_2$. When the patient 1000 inhales the supply of gas generated by the RPT device during breathing, the mucosal surfaces of the patient's airways 1004 provide moisture to the air as it is inhaled and the moisture is retained in the air once it is exhaled. However, the washout of the expired gas, with the higher concentration of $CO_2$, or vent flow 7004 discharges the moisture added to the air by the patient's mucosal surfaces along with the $CO_2$. Over the course of a treatment session, e.g., while the patient sleeps, this may result in drying of the mucosal surfaces which may become uncomfortable for the patient.

Related technologies have addressed this issue by providing a humidifier 5000, described in greater detail elsewhere herein, to add moisture, i.e., humidify, the flow of gas 7000 provided to the patient interface 3000 for therapy. In other words, the humidifier 5000 may be understood to resupply the moisture lost through the vent flow 7004 by providing moisture in the flow of gas 7000 supplied to the patient. While a humidifier 5000 may effectively reduce the drying of the patient's airways 1004 during therapy, the humidifier 5000 may require a source of moisture, a source of power, and control systems to coordinate operation of the humidifier 5000 with the RPT device 4000 to deliver the desired level of humidity and therapy to the patient. Therefore, it may be desirable to provide another solution to the problem of the loss of moisture during therapy without the requirements associated with the humidifier 5000.

A non-invasive patient interface 3000 in accordance with one aspect of the present technology comprises a device 6000. The device 6000 may be heat non-absorbent or resistant to the absorption of heat and/or the device 6000 may be moisture non-absorbent or resistant to the absorption of moisture.

The device 6000 may be positioned within the plenum chamber 3200 of the patient interface 3000 in accordance with an example of the present technology. The device 6000 may also be located in a breathing chamber that is defined, at least in part, by the seal-forming structure 3100 and the plenum chamber 3200. Alternatively, the device 6000 may be positioned within the decoupling structure 3500 or an elbow of the patient interface 3000. Alternatively, the device 6000 may be positioned within the air circuit 4170. The device 6000 may be configured to direct the flow of breathable gas 7000 through at least one aperture 6002 to reduce a turbulence of the flow 7000 towards a mucosal surface of the patient's airways 1004 to reduce drying of the mucosal surface.

The device may comprise a plurality of apertures 6002 of a predetermined size. The device 6000 may be positioned between the connection port 3600 and the entrance 1006 of a patient's airways 1004 such that it directs some or all of the flow of breathable gas 7000 through the apertures 6002. The device 6000 may comprise a predetermined surface area to physically interfere with and direct all of the flow 7000 through the apertures 6002. Also, the expiratory flow 7002 from the patient's airways 1004 may be directed out of the plenum chamber 3200 by passing in the opposite direction through the apertures 6002 and out the vent 3400 as the washout or vent flow 7004.

In one form, the device 6000 may separate the plenum chamber 3200 into a first, anterior chamber 6004 and a second, posterior chamber 6006. The second, posterior chamber 6006 is positioned such that it is adjacent to the entrance 1006 of the patient's airways 1004. The device 6000 may physically interfere with the flow of expiratory gas 7002 to increase the humidity in the second, posterior chamber 6006 to a predetermined absolute humidity for redelivering humidification to the mucosal surface of the patient's airways 1004. The humidified flow of expiratory gas 7002 of the patient may be decelerated from flowing into the first anterior chamber 6004, thereby increasing the humidity within the second posterior chamber 6006 for redelivery to the entrance of a patient's airways 1004. Thus, by reducing the velocity of the expiratory flow 7002 within the plenum chamber 3200, by forcing the expiratory flow 7002 to pass through the apertures 6002 from the second, posterior chamber 6006 to the first, anterior chamber 6004, the turbulence in the second, posterior chamber 6006 may be reduced. It should be understood that the device 6000 may reduce the velocity or kinetic energy of the flow 7000 by impeding its passage to the second, posterior chamber 6006, which in turn reduces turbulence in the flow. The reduction of the turbulence in the second, posterior chamber 6006 may in turn reduce mixing between the expiratory flow 7002 and the flow of breathable gas 7000 from the RPT device 4000, which may be less humid. Thus, there may be a reduction in the loss of moisture from the expiratory flow 7002, a substantial portion of which may ultimately be retained in the second, posterior chamber 6006 and can be used to humidify air inhaled by the patient 1000 such that the patient's airways 1004 do not dry out. Additionally, by retaining more moisture in the second, posterior chamber 6006, there is less moisture that is transferred to the first, anterior chamber 6004 that may ultimately be lost from the plenum chamber 3200 by, for example, the vent flow 7004. The absolute humidity within the second, posterior chamber 6006 may reach greater than 10 mg/L.

In one form, the seal-forming structure 3100 of the patient interface 3000 may be configured to seal on a portion of the patient's 1000 face to provide the flow of breathable gas 7000 at a therapeutic pressure level for RPT to treat conditions such as sleep disordered breathing. The flow of breathable gas 7000 flows from the connection port 3600, into the plenum chamber 3200 and through the apertures 6002 of the device 6000 before reaching the entrance of the patient's airways 1004. The permeability of the device 6000 to the flow of breathable gas 7000 may be increased to maintain a predetermined level of pressure when the flow of breathable gas 7000 flows through the apertures 6002 to avoid significant losses of therapeutic pressure prior to reaching the entrance of the patient's airways 1004. The predetermined pressure level may be between 2 cm $H_2O$ to 40 cm $H_2O$. The permeability may be increased by increasing an anterior flow area of the apertures 6002. The anterior flow area of the apertures 6002 is the area in which the apertures occupy on an anterior side of the device 6000 to allow the flow of breathable gas 7000 through the apertures 6002. The anterior flow area may be selected by selecting apertures 6002 having a predetermined size. Alternatively, the permeability of the device 6000 to the flow of breathable gas 7000 may be increased by increasing the number of apertures 6002. Thus, the area of the apertures 6002 on the anterior side of the device 6000 and the number of the apertures 6002 are two factors in determining the anterior flow area of the device 6000.

In one form, the device 6000 may be positioned between the vent 3400 and the patient 1000 such that the flow of expiratory gas 7002 flows through the apertures 6002 of the device 6000 prior to flowing out of the vent 3400 for $CO_2$ washout as the vent flow 7004. The permeability of the device 6000 to the flow of expiratory gas 7002 may be increased to allow the flow of expiratory gas 7002 through the apertures 6002 for a predetermined level of $CO_2$ washout. The permeability to the flow of expiratory gas 7002 may be increased by increasing a posterior flow area of the apertures 6002. The desired posterior flow area of the device 6000 may be selected by selecting apertures 6002 having a predetermined size. In addition, the permeability may be increased by increasing the number of the apertures 6002. Thus, the area of the apertures 6002 on the posterior side of the device 6000 and the number of the apertures 6002 are two factors in determining the posterior flow area of the device 6000.

In another form, the apertures 6002 may each comprise an inner surface profile configured to direct the flow of expiratory gas 7002 towards the vent 3400 for the predetermined level of $CO_2$ washout. The predetermined level of $CO_2$ washout or vent flow 7004 may be sufficient to prevent significant $CO_2$ rebreathing resulting in deleterious effects such as sudden awakening during RPT in the treatment of SDB.

In one form, the device 6000 may be a flexible membrane sheet, as shown in FIG. 8A. Alternatively, the device 6000 may be a textile formed of woven fibres and wherein the fibres form a plurality of apertures 6002 between adjacent fibres, as shown in FIG. 8B. In another form, the device 6000 may be a mesh structure, as shown in FIG. 8C.

FIGS. 9A and 9B show two perspective views of a device 6000 according to the present technology. The device 6000 can be seen with a number of apertures 6002. The apertures 6002 may be uniform in size and shape over the entirety of the device 6000. Alternatively, the size of the apertures 6002 may be varied in different regions of the device 6000, the shape of the apertures 6002 may be varied in different regions of the device 6000, and/or the density of the apertures 6002, i.e., the number of apertures 6002 per unit area of the surface of the device 6000, may be varied in different regions of the device 6000.

Furthermore, the device 6000 may be shaped such that its periphery substantially conforms to the interior surface of the plenum chamber 3200 to provide a secure fit within the patient interface 3000. The device 6000 may be secured to the interior of the plenum chamber 3200 with a friction fit, a press fit, a snap fit, adhesive, molding, and/or clips or other attachment structures. Alternatively, the device 6000 may be formed in one piece with the plenum chamber 3200 such that the device 6000 and the plenum chamber 3200 comprise a single piece of homogenous and continuous material.

According to further examples, the device 6000 may be formed of a material that is heat non-absorbent or resistant to the absorption of heat and/or the device 6000 may be moisture non-absorbent or resistant to the absorption of moisture. The material of the device 6000 may be any one of the group consisting of Nylon, polycarbonate, silicone, polyurethane, thermoplastic elastomers, hydrophobic polymers, and other synthetic materials. Alternatively, the device 6000 may comprise a material that forms a heat and moisture exchanger, such as paper. However, in this instance, the device 6000 may be too thin to effectively exchange heat and moisture to provide humidification at the predetermined level. Thus, the device 6000 may rely mostly on the ability to direct the flow of breathable gas 7000 to reduce the turbulence of the flow towards the mucosal surface of the patient's airways 1004 to reduce drying of the mucosal surface.

In one form, the device 6000 may be less than 1 cm thick, according to an example of the present technology. According to another example of the present technology, the device 6000 may be less than 0.5 cm thick. According to another example of the present technology, the device 6000 may be less than 1 mm thick. The device 6000 may occupy a smaller volume within the plenum chamber 3200 to reduce its impact on the flow of breathable gas 7000, the flow of expiratory gas 7002 from the patient, and/or the vent flow 7004. The device 6000 may reduce the drying of the mucosal surface of a patient's airways 1004 to avoid breathing discomfort to the same effect as powered humidification or the use of a HME. However, the device 6000 will not require any external power source and the device 6000 is capable of occupying a significantly smaller size and volume when compared to an HME that may provide a similar level of breathing comfort through heat and moisture exchange. Occupying a smaller volume may have the effect of reducing impedance on the flow of breathable gas 7000 that results in pressure losses during RPT for the treatment of SDB. The smaller device 6000 may also have a reduced impedance on the flow of expiratory gas 7002 to the vent 3400 and/or the vent flow 7004 that washes out $CO_2$. Moreover, a smaller device 6000 may allow for additional space to accommodate a portion of the patient's face within the patient interface 3000 when compared to the use of an in-mask HME.

FIG. 11 shows an increase in average absolute humidity when measured in the posterior chamber 6006 of the patient interface 3000 comprising a device 6000 in use. As shown, the absolute humidity was measured in the patient interface 3000 proximal to the entrance of a patient's airways 1004 in: 1) a patient interface 3000 without the device 6000, 2) a patient interface 3000 comprising the device 6000 comprising a HME material, and 3) a patient interface 3000 comprising the device 6000 in the form of a woven material that is heat non-absorbent or resistant to absorption of heat and moisture non-absorbent or resistant to absorption of moisture. The results show a significant increase in absolute humidity, with the best result shown for the patient interface comprising the device 6000 in the form of a woven material that is heat non-absorbent or resistant to absorption of heat and moisture non-absorbent or resistant to absorption of moisture.

FIGS. 12A and 12B show a test rig or a model 3900 that was utilised to measure the turbulence of the flow of breathable gas 7000 in a simulated patient interface system with a device 6000 and a simulated patient interface system without a device 6000. The test rig 3900 comprises a simulated entrance 1002 to the patient's airways, a simulated vent 3400 and a simulated connection port 3600. The volume of the test rig 3900 may also be understood to be defined, at least in part, by simulated forms of the seal-forming structure 3100 and the plenum chamber 3200. In other words, the test rig 3900 may be understood to model the breathing chamber defined, at least in part, by the seal-forming structure 3100 and the plenum chamber 3200 when placed against the patient's face.

FIGS. 13A to 16B show the results of measuring turbulence or flow in the test rig 3900 using a computational fluid dynamics program. The results show that in the test rig 3900 comprising the device 6000 that the turbulence of the gas may be reduced significantly by the device 6000, when compared to the test rig 3900 without the device 6000. Although FIGS. 12A and 12B show the test rig 3900 with the device 6000, it should be understood that the FIGS. 13A, 14A, 15A, and 16A depict modelling of flows in the test rig 3900 without the device 6000, while FIGS. 13B, 14B, 15B, and 16B show depict modelling of flows in the test rig 3900 with the device 6000.

FIGS. 13A and 13B show velocities of gas flow in the test rig 3900 without and with the device 6000, respectively. In this simulation, the patient's expiratory flow 7002 via the simulated entrance 1002 is zero and there is a flow of breathable gas 7000 entering into the test rig 3900 via the connection port 3600. As can be seen in FIG. 13B, where the test rig 3900 includes the device 6000, turbulence is reduced in the posterior chamber 6006 relative to the anterior chamber 6004.

FIGS. 14A and 14B show velocities of gas flow in the test rig 3900 without and with the device 6000, respectively. In this simulation, the patient's expiratory flow 7002 via the simulated entrance 1002 is positive, i.e., the patient is exhaling, and there is a flow of breathable gas 7000 entering into the test rig 3900 via the connection port 3600. As can be seen in FIG. 13B, where the test rig 3900 includes the device 6000, turbulence is reduced in the posterior chamber 6006 relative to the anterior chamber 6004.

FIGS. 15A and 15B show streamlines of gas flow in the test rig 3900 without and with the device 6000, respectively. In this simulation, the patient's expiratory flow 7002 via the simulated entrance 1002 is zero and there is a flow of breathable gas 7000 entering into the test rig 3900 via the connection port 3600. As can be seen in FIG. 15B, where the test rig 3900 includes the device 6000, turbulence is reduced in the posterior chamber 6006 relative to the anterior chamber 6004.

FIGS. 16A and 16B show streamlines of gas flow in the test rig 3900 without and with the device 6000, respectively. In this simulation, the patient's expiratory flow 7002 via the simulated entrance 1002 is positive, i.e., the patient is exhaling, and there is a flow of breathable gas 7000 entering into the test rig 3900 via the connection port 3600. As can be seen in FIG. 16B, where the test rig 3900 includes the device 6000, turbulence is reduced in the posterior chamber 6006 relative to the anterior chamber 6004.

5.4 RPT Device

An RPT device 4000 in accordance with one aspect of the present technology comprises mechanical and pneumatic components 4100, electrical components 4200 and is configured to execute one or more algorithms 4300. The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors 4272 and flow rate sensors 4274.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

5.4.1 RPT Device Mechanical & Pneumatic Components

An RPT device may comprise one or more of the following components in an integral unit. In an alternative form, one or more of the following components may be located as respective separate units.

5.4.1.1 Air Filter(s)

An RPT device in accordance with one form of the present technology may include an air filter 4110, or a plurality of air filters 4110.

In one form, an inlet air filter 4112 is located at the beginning of the pneumatic path upstream of a pressure generator 4140. See FIG. 4b.

In one form, an outlet air filter 4114, for example an antibacterial filter, is located between an outlet of the pneumatic block 4020 and a patient interface 3000. See FIG. 4b.

5.4.1.2 Muffler(s)

In one form of the present technology, an inlet muffler 4122 is located in the pneumatic path upstream of a pressure generator 4140. See FIG. 4b.

In one form of the present technology, an outlet muffler 4124 is located in the pneumatic path between the pressure generator 4140 and a patient interface 3000. See FIG. 4b.

5.4.1.3 Pressure Generator 4140

In one form of the present technology, a pressure generator 4140 for producing a flow, or a supply, of air at positive pressure is a controllable blower 4142. For example the blower 4142 may include a brushless DC motor 4144 with one or more impellers housed in a volute. The blower may be capable of delivering a supply of air, for example at a rate of up to about 120 litres/minute, at a positive pressure in a range from about 4 $cmH_2O$ to about 20 $cmH_2O$, or in other forms up to about 30 $cmH_2O$. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

The pressure generator 4140 is under the control of the therapy device controller 4240.

In other forms, a pressure generator 4140 may be a piston-driven pump, a pressure regulator connected to a high pressure source (e.g. compressed air reservoir), or a bellows.

5.4.1.4 Transducer(s)

Transducers may be internal of the RPT device, or external of the RPT device. External transducers may be located for example on or form part of the air circuit, e.g., the patient interface. External transducers may be in the form of non-contact sensors such as a Doppler radar movement sensor that transmit or transfer data to the RPT device.

In one form of the present technology, one or more transducers 4270 are located upstream and/or downstream of the pressure generator 4140. The one or more transducers 4270 may be constructed and arranged to measure properties such as a flow rate, a pressure or a temperature at that point in the pneumatic path.

In one form of the present technology, one or more transducers 4270 may be located proximate to the patient interface 3000.

In one form, a signal from a transducer 4270 may be filtered, such as by low-pass, high-pass or band-pass filtering.

5.4.1.4.1 Flow Rate Transducer

A flow rate transducer 4274 in accordance with the present technology may be based on a differential pressure transducer, for example, an SDP600 Series differential pressure transducer from SENSIRION.

In one form, a signal representing a flow rate such as a total flow rate Qt from the flow rate transducer 4274 is received by the central controller 4230.

5.4.1.4.2 Pressure Transducer 4272

A pressure transducer 4272 in accordance with the present technology is located in fluid communication with the pneumatic path. An example of a suitable pressure transducer is a sensor from the HONEYWELL ASDX series. An alternative suitable pressure transducer is a sensor from the NPA Series from GENERAL ELECTRIC.

In one form, a signal from the pressure transducer 4272 is received by the central controller 4230.

5.4.1.4.3 Motor Speed Transducer

In one form of the present technology a motor speed transducer 4276 is used to determine a rotational velocity of the motor 4144 and/or the blower 4142. A motor speed signal from the motor speed transducer 4276 may be provided to the therapy device controller 4240. The motor speed transducer 4276 may, for example, be a speed sensor, such as a Hall effect sensor.

5.4.1.5 Anti-Spill Back Valve

In one form of the present technology, an anti-spill back valve is located between the humidifier 5000 and the pneumatic block 4020. The anti-spill back valve is constructed and arranged to reduce the risk that water will flow upstream from the humidifier 5000, for example to the motor 4144.

5.4.1.6 Air Circuit

An air circuit 4170 in accordance with an aspect of the present technology is a conduit or a tube constructed and arranged in use to allow a flow of air to travel between two components such as the pneumatic block 4020 and the patient interface 3000.

In particular, the air circuit 4170 may be in fluid connection with the outlet of the pneumatic block and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller 4230 or a humidifier controller 5250. One example of an air circuit 4170 comprising a heated wire circuit is described in United States Patent Application No. US/2011/0023874, which is incorporated herewithin in its entirety by reference.

5.4.1.7 Oxygen Delivery

In one form of the present technology, supplemental oxygen 4180 is delivered to one or more points in the pneumatic path, such as upstream of the pneumatic block 4020, to the air circuit 4170 and/or to the patient interface 3000.

5.4.2 RPT Device Electrical Components

5.4.2.1 Power Supply

A power supply 4210 may be located internal or external of the external housing 4010 of the RPT device 4000.

In one form of the present technology power supply 4210 provides electrical power to the RPT device 4000 only. In another form of the present technology, power supply 4210 provides electrical power to both RPT device 4000 and humidifier 5000.

5.4.2.2 Input Devices

In one form of the present technology, an RPT device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form, the input device 4220 may be constructed and arranged to allow a person to select a value and/or a menu option.

5.4.2.3 Central Controller

In one form of the present technology, the central controller 4230 is one or a plurality of processors suitable to control an RPT device 4000.

Suitable processors may include an x86 INTEL processor, a processor based on ARM® Cortex®-M processor from ARM Holdings such as an STM32 series microcontroller from ST MICROELECTRONIC. In certain alternative forms of the present technology, a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS may also be suitable.

In one form of the present technology, the central controller 4230 is a dedicated electronic circuit.

In one form, the central controller 4230 is an application-specific integrated circuit. In another form, the central controller 4230 comprises discrete electronic components.

The central controller 4230 may be configured to receive input signal(s) from one or more transducers 4270, and one or more input devices 4220.

The central controller 4230 may be configured to provide output signal(s) to one or more of an output device 4290, a therapy device controller 4240, a data communication interface 4280 and humidifier controller 5250.

In some forms of the present technology, the central controller 4230 is configured to implement the one or more methodologies described herein, such as the one or more algorithms 4300 expressed as computer programs stored in a non-transitory computer readable storage medium, such as memory 4260. In some forms of the present technology, the central controller 4230 may be integrated with an RPT device 4000. However, in some forms of the present technology, some methodologies may be performed by a remotely located device. For example, the remotely located device may determine control settings for a ventilator or detect respiratory related events by analysis of stored data such as from any of the sensors described herein.

5.4.2.4 Clock

The RPT device 4000 may include a clock 4232 that is connected to the central controller 4230.

5.4.2.5 Therapy Device Controller

In one form of the present technology, therapy device controller 4240 is a control module 4330 that forms part of the algorithms 4300 executed by the central controller 4230.

In one form of the present technology, therapy device controller 4240 is a dedicated motor control integrated circuit. For example, in one form a MC33035 brushless DC motor controller, manufactured by ONSEMI is used.

5.4.2.6 Protection Circuits

The one or more protection circuits 4250 in accordance with the present technology may comprise an electrical protection circuit, a temperature and/or pressure safety circuit.

5.4.2.7 Memory

In accordance with one form of the present technology the RPT device 4000 includes memory 4260, e.g., non-volatile memory. In some forms, memory 4260 may include battery powered static RAM. In some forms, memory 4260 may include volatile RAM.

Memory 4260 may be located on the PCBA 4202. Memory 4260 may be in the form of EEPROM, or NAND flash.

Additionally or alternatively, RPT device 4000 includes a removable form of memory 4260, for example a memory card made in accordance with the Secure Digital (SD) standard.

In one form of the present technology, the memory 4260 acts as a non-transitory computer readable storage medium on which is stored computer program instructions expressing the one or more methodologies described herein, such as the one or more algorithms 4300.

5.4.2.8 Data Communication Systems

In one form of the present technology, a data communication interface 4280 is provided, and is connected to the central controller 4230. Data communication interface 4280 may be connectable to a remote external communication network 4282 and/or a local external communication network 4284. The remote external communication network 4282 may be connectable to a remote external device 4286. The local external communication network 4284 may be connectable to a local external device 4288.

In one form, data communication interface 4280 is part of the central controller 4230. In another form, data communication interface 4280 is separate from the central controller 4230, and may comprise an integrated circuit or a processor.

In one form, remote external communication network 4282 is the Internet. The data communication interface 4280 may use wired communication (e.g. via Ethernet, or optical fibre) or a wireless protocol (e.g. CDMA, GSM, LTE) to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such remote external device 4286 may be accessible to an appropriately authorised person such as a clinician.

The local external device 4288 may be a personal computer, mobile phone, tablet or remote control.

5.4.2.9 Output Devices Including Optional Display, Alarms

An output device 4290 in accordance with the present technology may take the form of one or more of a visual, audio and haptic unit. A visual display may be a Liquid Crystal Display (LCD) or Light Emitting Diode (LED) display.

5.4.2.9.1 Display Driver

A display driver 4292 receives as an input the characters, symbols, or images intended for display on the display 4294, and converts them to commands that cause the display 4294 to display those characters, symbols, or images.

5.4.2.9.2 Display

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

5.5 Humidifier 5.5.1 Humidifier Overview

In one form of the present technology there is provided a humidifier 5000 (e.g. as shown in FIG. 5a) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5a and FIG. 5b, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

5.5.2 Humidifier Mechanical Components

5.5.2.1 Water Reservoir

According to one arrangement, the humidifier 5000 may comprise a water reservoir 5110 configured to hold, or retain, a volume of liquid (e.g. water) to be evaporated for humidification of the flow of air. The water reservoir 5110 may be configured to hold a predetermined maximum volume of water in order to provide adequate humidification for at least the duration of a respiratory therapy session, such as one evening of sleep. Typically, the reservoir 5110 is configured to hold several hundred millilitres of water, e.g. 300 millilitres (ml), 325 ml, 350 ml or 400 ml. In other forms, the humidifier 5000 may be configured to receive a supply of water from an external water source such as a building's water supply system.

According to one aspect, the water reservoir 5110 is configured to add humidity to a flow of air from the RPT device 4000 as the flow of air travels therethrough. In one form, the water reservoir 5110 may be configured to encourage the flow of air to travel in a tortuous path through the reservoir 5110 while in contact with the volume of water therein.

According to one form, the reservoir 5110 may be removable from the humidifier 5000, for example in a lateral direction as shown in FIG. 5a and FIG. 5b.

The reservoir 5110 may also be configured to discourage egress of liquid therefrom, such as when the reservoir 5110 is displaced and/or rotated from its normal, working orientation, such as through any apertures and/or in between its sub-components. As the flow of air to be humidified by the humidifier 5000 is typically pressurised, the reservoir 5110 may also be configured to prevent losses in pneumatic pressure through leak and/or flow impedance.

5.5.2.2 Conductive Portion

According to one arrangement, the reservoir 5110 comprises a conductive portion 5120 configured to allow efficient transfer of heat from the heating element 5240 to the volume of liquid in the reservoir 5110. In one form, the conductive portion 5120 may be arranged as a plate, although other shapes may also be suitable. All or a part of the conductive portion 5120 may be made of a thermally conductive material such as aluminium (e.g. approximately 2 mm thick, such as 1 mm, 1.5 mm, 2.5 mm or 3 mm), another heat conducting metal or some plastics. In some cases, suitable heat conductivity may be achieved with less conductive materials of suitable geometry.

5.5.2.3 Humidifier Reservoir Dock

In one form, the humidifier 5000 may comprise a humidifier reservoir dock 5130 (as shown in FIG. 5b) configured to receive the humidifier reservoir 5110. In some arrangements, the humidifier reservoir dock 5130 may comprise a locking feature such as a locking lever 5135 configured to retain the reservoir 5110 in the reservoir dock 5130.

5.5.2.4 Water Level Indicator

The humidifier reservoir 5110 may comprise a water level indicator 5150 as shown in FIG. 5a-5b. In some forms, the water level indicator 5150 may provide one or more indications to a user such as the patient 1000 or a care giver regarding a quantity of the volume of water in the humidifier reservoir 5110. The one or more indications provided by the water level indicator 5150 may include an indication of a maximum, predetermined volume of water, any portions thereof, such as 25%, 50% or 75% or volumes such as 200 ml, 300 ml or 400 ml.

5.5.3 Humidifier Electrical & Thermal Components

The humidifier 5000 may comprise a number of electrical and/or thermal components such as those listed below.

5.5.3.1 Humidifier Transducer(s)

The humidifier 5000 may comprise one or more humidifier transducers (sensors) 5210 instead of, or in addition to, transducers 4270 described above. Humidifier transducers 5210 may include one or more of an air pressure sensor 5212, an air flow rate transducer 5214, a temperature sensor 5216, or a humidity sensor 5218 as shown in FIG. 5c. A humidifier transducer 5210 may produce one or more output signals which may be communicated to a controller such as the central controller 4230 and/or the humidifier controller 5250. In some forms, a humidifier transducer may be located externally to the humidifier 5000 (such as in the air circuit 4170) while communicating the output signal to the controller.

5.5.3.1.1 Pressure Transducer

One or more pressure transducers 5212 may be provided to the humidifier 5000 in addition to, or instead of, a pressure transducer 4272 provided in the RPT device 4000.

5.5.3.1.2 Flow Rate Transducer

One or more flow rate transducers 5214 may be provided to the humidifier 5000 in addition to, or instead of, a flow rate transducer 4274 provided in the RPT device 4000.

5.5.3.1.3 Temperature Transducer

The humidifier 5000 may comprise one or more temperature transducers 5216. The one or more temperature transducers 5216 may be configured to measure one or more temperatures such as of the heating element 5240 and/or of the flow of air downstream of the humidifier outlet 5004. In some forms, the humidifier 5000 may further comprise a temperature sensor 5216 to detect the temperature of the ambient air.

5.5.3.1.4 Humidity Transducer

In one form, the humidifier 5000 may comprise one or more humidity sensors 5218 to detect a humidity of a gas, such as the ambient air. The humidity sensor 5218 may be placed towards the humidifier outlet 5004 in some forms to measure a humidity of the gas delivered from the humidifier 5000. The humidity sensor may be an absolute humidity sensor or a relative humidity sensor.

5.5.3.2 Heating Element

A heating element 5240 may be provided to the humidifier 5000 in some cases to provide a heat input to one or more of the volume of water in the humidifier reservoir 5110 and/or to the flow of air. The heating element 5240 may comprise a heat generating component such as an electrically resistive heating track. One suitable example of a heating element 5240 is a layered heating element such as one described in the PCT Patent Application Publication No. WO 2012/171072, which is incorporated herewith by reference in its entirety.

In some forms, the heating element 5240 may be provided in the humidifier base 5006 where heat may be provided to the humidifier reservoir 5110 primarily by conduction as shown in FIG. 5b.

5.5.3.3 Humidifier Controller

According to one arrangement of the present technology, a humidifier 5000 may comprise a humidifier controller 5250 as shown in FIG. 5c. In one form, the humidifier controller 5250 may be a part of the central controller 4230. In another form, the humidifier controller 5250 may be a separate controller, which may be in communication with the central controller 4230.

In one form, the humidifier controller 5250 may receive as inputs measures of characteristics (such as temperature, humidity, pressure and/or flow rate), for example of the flow of air, the water in the reservoir 5110 and/or the humidifier 5000. The humidifier controller 5250 may also be configured to execute or implement humidifier algorithms and/or deliver one or more output signals.

As shown in FIG. 5c, the humidifier controller may comprise one or more controllers, such as a central humidifier controller 5251, a heated air circuit controller 5254 configured to control the temperature of a heated air circuit 4171 and/or a heating element controller 5252 configured to control the temperature of a heating element 5240.

5.6 Breathing Waveforms

FIG. 6 shows a model typical breath waveform of a person while sleeping. The horizontal axis is time, and the vertical axis is respiratory flow rate. While the parameter values may vary, a typical breath may have the following approximate values: tidal volume, Vt, 0.5 L, inhalation time, Ti, 1.6 s, peak inspiratory flow rate, Qpeak, 0.4 L/s, exhalation time, Te, 2.4 s, peak expiratory flow rate, Qpeak, −0.5 L/s. The total duration of the breath, Ttot, is about 4 s. The person typically breathes at a rate of about 15 breaths per minute (BPM), with Ventilation, Vent, about 7.5 L/minute. A typical duty cycle, the ratio of Ti to Ttot is about 40%.

5.7 Glossary

For the purposes of the present technology disclosure, in certain forms of the present technology, one or more of the following definitions may apply. In other forms of the present technology, alternative definitions may apply.

5.7.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Continuous Positive Airway Pressure (CPAP) therapy: CPAP therapy will be taken to mean the application of a supply of air to an entrance to the airways at a pressure that is continuously positive with respect to atmosphere. The pressure may be approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Patient: A person, whether or not they are suffering from a respiratory disease.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

5.7.2 Aspects of the Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): Breathing effort will be said to be the work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:

(i) Flattened: Having a rise followed by a relatively flat portion, followed by a fall.

(ii) M-shaped: Having two local peaks, one at the leading edge, and one at the trailing edge, and a relatively flat portion between the two peaks.

(iii) Chair-shaped: Having a single local peak, the peak being at the leading edge, followed by a relatively flat portion.

(iv) Reverse-chair shaped: Having a relatively flat portion followed by single local peak, the peak being at the trailing edge.

Hypopnea: Preferably, a hypopnea will be taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:

(i) a 30% reduction in patient breathing for at least 10 seconds plus an associated 4% desaturation; or (ii) a reduction in patient breathing (but less than 50%) for at least 10 seconds, with an associated desaturation of at least 3% or an arousal.

Hyperpnea: An increase in flow to a level higher than normal flow rate.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, airflow rate, patient airflow rate, respiratory airflow rate (Qr): These synonymous terms may be understood to refer to the RPT device's estimate of respiratory airflow rate, as opposed to "true respiratory flow" or "true respiratory airflow", which is the actual respiratory flow rate experienced by the patient, usually expressed in litres per minute.

Tidal volume (Vt): The volume of air inhaled or exhaled during normal breathing, when extra effort is not applied.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of the inspiratory portion of one respiratory flow rate waveform and the start of the inspiratory portion of the following respiratory flow rate waveform.

Typical recent ventilation: The value of ventilation around which recent values over some predetermined timescale tend to cluster, that is, a measure of the central tendency of the recent values of ventilation.

Upper airway obstruction (UAO): includes both partial and total upper airway obstruction. This may be associated with a state of flow limitation, in which the level of flow increases only slightly or may even decrease as the pressure difference across the upper airway increases (Starling resistor behaviour).

Ventilation (Vent): A measure of the total amount of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

5.7.3 RPT Device Parameters

Flow rate: The instantaneous volume (or mass) of air delivered per unit time. While flow rate and ventilation have the same dimensions of volume or mass per unit time, flow rate is measured over a much shorter period of time. In some cases, a reference to flow rate will be a reference to a scalar quantity, namely a quantity having magnitude only. In other cases, a reference to flow rate will be a reference to a vector quantity, namely a quantity having both magnitude and direction. Where it is referred to as a signed quantity, a flow rate may be nominally positive for the inspiratory portion of a breathing cycle of a patient, and hence negative for the expiratory portion of the breathing cycle of a patient. Flow rate will be given the symbol Q. 'Flow rate' is sometimes shortened to simply 'flow'. Total flow rate, Qt, is the flow rate of air leaving the RPT device. Vent flow rate, Qv, is the flow rate of air leaving a vent to allow washout of exhaled gases. Leak flow rate, Ql, is the flow rate of leak from a patient interface system. Respiratory flow rate, Qr, is the flow rate of air that is received into the patient's respiratory system.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes in the patient interface.

Pressure: Force per unit area. Pressure may be measured in a range of units, including $cmH_2O$, $g\text{-}f/cm^2$, hectopascal. 1 $cmH_2O$ is equal to 1 $g\text{-}f/cm^2$ and is approximately 0.98 hectopascal. In this specification, unless otherwise stated, pressure is given in units of $cmH_2O$. The pressure in the patient interface is given the symbol Pm, while the treatment pressure, which represents a target value to be achieved by the mask pressure Pm at the current instant of time, is given the symbol Pt.

Sound Power: The energy per unit time carried by a sound wave. The sound power is proportional to the square of sound pressure multiplied by the area of the wavefront. Sound power is usually given in decibels SWL, that is, decibels relative to a reference power, normally taken as $10^{-12}$ watt.

Sound Pressure: The local deviation from ambient pressure at a given time instant as a result of a sound wave travelling through a medium. Sound pressure is usually given in decibels SPL, that is, decibels relative to a reference pressure, normally taken as $20 \times 10^{-6}$ Pascal (Pa), considered the threshold of human hearing.

5.7.4 Terms for Ventilators

Adaptive Servo-Ventilator (ASV): A servo-ventilator that has a changeable, rather than fixed target ventilation. The changeable target ventilation may be learned from some characteristic of the patient, for example, a respiratory characteristic of the patient.

Backup rate: A parameter of a ventilator that establishes the minimum breathing rate (typically in number of breaths per minute) that the ventilator will deliver to the patient, if not triggered by spontaneous respiratory effort.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

EPAP: a base pressure, to which a pressure varying within the breath is added to produce the desired mask pressure which the ventilator will attempt to achieve at a given time.

IPAP: desired mask pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the minimum value during expiration (e.g., PS=IPAP−EPAP). In some contexts pressure support means the difference which the ventilator aims to achieve, rather than what it actually achieves.

Servo-ventilator: A ventilator that measures patient ventilation, has a target ventilation, and which adjusts the level of pressure support to bring the patient ventilation towards the target ventilation.

Spontaneous/Timed (S/T): A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator delivers a breath of air to a spontaneously breathing patient, it is said to be triggered to do so at the initiation of the respiratory portion of the breathing cycle by the patient's efforts.

Typical recent ventilation: The typical recent ventilation Vtyp is the value around which recent measures of ventilation over some predetermined timescale tend to cluster. For example, a measure of the central tendency of the measures of ventilation over recent history may be a suitable value of a typical recent ventilation.

Ventilator: A mechanical device that provides pressure support to a patient to perform some or all of the work of breathing.

5.7.5 Anatomy of the Face

Ala: the external outer wall or "wing" of each nostril (plural: alar)

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfurt horizontal while intersecting subnasale.

Frankfort horizontal plane: A line extending from the most inferior point of the orbital margin to the left tragion. The tragion is the deepest point in the notch superior to the tragus of the auricle.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear) dividing the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramentale: The point of greatest concavity in the midline of the lower lip between labrale inferius and soft tissue pogonion 5.7.6 Anatomy of the Skull Frontal bone: The frontal bone includes a large vertical portion, the squama frontalis, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

5.7.7 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

5.7.8 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a typically transparent thermoplastic polymer of Bisphenol-A Carbonate.

5.7.9 Aspects of a Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: A conduit that directs an axis of flow of air to change direction through an angle. In one form, the angle may be approximately 90 degrees. In another form, the angle may be less than 90 degrees. The conduit may have an approximately circular cross-section. In another form the conduit may have an oval or a rectangular cross-section.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. Preferably the headgear comprises a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls enclosing a volume of space, the volume having air therein pressurised above atmospheric pressure in use. A shell may form part of the walls of a mask plenum chamber.

Seal: The noun form ("a seal") will be taken to mean a structure or barrier that intentionally resists the flow of air through the interface of two surfaces. The verb form ("to seal") will be taken to mean to resist a flow of air.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel: (noun) A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie: A tie will be taken to be a structural component designed to resist tension.

Vent: (noun) the structure that allows an intentional flow of air from an interior of the mask, or conduit to ambient air, e.g. to allow washout of exhaled gases.

5.7.10 Terms Used in Relation to Patient Interface

Curvature (of a surface): A region of a surface having a saddle shape, which curves up in one direction and curves down in a different direction, will be said to have a negative curvature. A region of a surface having a dome shape, which curves the same way in two principal directions, will be said to have a positive curvature. A flat surface will be taken to have zero curvature.

Floppy: A quality of a material, structure or composite that is one or more of:

Readily conforming to finger pressure.

Unable to retain its shape when caused to support its own weight.

Not rigid.

Able to be stretched or bent elastically with little effort.

The quality of being floppy may have an associated direction, hence a particular material, structure or composite may be floppy in a first direction, but stiff or rigid in a second direction, for example a second direction that is orthogonal to the first direction.

Resilient: Able to deform substantially elastically, and to release substantially all of the energy upon unloading, within a relatively short period of time such as 1 second.

Rigid: Not readily deforming to finger pressure, and/or the tensions or loads typically encountered when setting up and maintaining a patient interface in sealing relationship with an entrance to a patient's airways.

Semi-rigid: means being sufficiently rigid to not substantially distort under the effects of mechanical forces typically applied during respiratory pressure therapy.

5.8 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

5.9 Reference Signs List

| | |
|---|---|
| patient | 1000 |
| simulated entrance to patient's airways | 1002 |
| patient's airways | 1004 |
| entrance to patient's airways | 1006 |
| bed partner | 1100 |
| patient interface | 3000 |
| seal - forming structure | 3100 |
| sealing flange | 3110 |
| plenum chamber | 3200 |
| positioning and stabilising structure | 3300 |
| vent | 3400 |
| decoupling structure | 3500 |
| swivel | 3510 |
| connection port | 3600 |
| forehead support | 3700 |
| test rig | 3900 |
| RPT device | 4000 |
| external housing | 4010 |
| upper portion | 4012 |
| lower portion | 4014 |
| panel | 4015 |
| chassis | 4016 |
| handle | 4018 |
| pneumatic block | 4020 |
| pneumatic component | 4100 |
| air filter | 4110 |
| inlet air filter | 4112 |
| outlet air filter | 4114 |
| inlet muffler | 4122 |
| outlet muffler | 4124 |
| pressure generator | 4140 |
| blower | 4142 |
| motor | 4144 |
| air circuit | 4170 |
| heated air circuit | 4171 |
| supplemental oxygen | 4180 |
| electrical component | 4200 |
| printed circuit board ssembly PCBA | 4202 |
| power supply | 4210 |
| input device | 4220 |
| central controller | 4230 |

-continued

| | |
|---|---|
| clock | 4232 |
| therapy device controller | 4240 |
| protection circuit | 4250 |
| memory | 4260 |
| transducer | 4270 |
| pressure sensor | 4272 |
| flow rate sensor | 4274 |
| motor speed transducer | 4276 |
| data communication interface | 4280 |
| remote external communication network | 4282 |
| local external communication network | 4284 |
| remote external device | 4286 |
| local external device | 4288 |
| output device | 4290 |
| display driver | 4292 |
| display | 4294 |
| algorithm | 4300 |
| control module | 4330 |
| humidifier | 5000 |
| humidifier inlet | 5002 |
| humidifier outlet | 5004 |
| humidifier base | 5006 |
| humidifier reservoir | 5110 |
| conductive portion | 5120 |
| humidifier reservoir dock | 5130 |
| locking lever | 5135 |
| water level indicator | 5150 |
| humidifier transducer | 5210 |
| pressure transducer | 5212 |
| flow rate transducer | 5214 |
| temperature sensor | 5216 |
| humidity sensor | 5218 |
| heating element | 5240 |
| humidifier controller | 5250 |
| central humidifier controller | 5251 |
| heating element controller | 5252 |
| air circuit controller | 5254 |
| device | 6000 |
| aperture | 6002 |
| anterior chamber | 6004 |
| posterior chamber | 6006 |
| flow of breathable gas | 7000 |
| expiratory flow | 7002 |
| vent flow | 7004 |

The invention claimed is:

1. A patient interface for sealed delivery of a flow of air at a continuously positive pressure with respect to ambient air pressure to an entrance to the patient's airways including at least an entrance of a patient's nares, wherein the patient interface is configured to maintain a therapy pressure in a range of about 4 cmH2O to about 30 cmH2O above ambient air pressure in use, throughout the patient's respiratory cycle, while the patient is sleeping, to ameliorate sleep disordered breathing, said patient interface comprising:

a seal-forming structure configured to contact and pneumatically seal against the patient's face at an area surrounding the entrance to the patient's airways;

a positioning and stabilising structure configured to maintain the seal-forming structure in sealing contact with the area surrounding the entrance to the patient's airways while maintaining a therapeutic pressure at the entrance to the patient's airways;

a plenum chamber configured to be pressurised at a pressure above ambient pressure in use, the seal-forming structure and the plenum chamber forming, at least in part, a breathing chamber when the seal-forming structure is in sealing contact with the area surrounding the entrance to the patient's airways;

a connection port positioned on the plenum chamber and configured to deliver the flow of air to the breathing chamber;

an elbow configured to fluidly communicate with the connection port; and a vent configured to wash out gas from the breathing chamber; and a device positioned within the breathing chamber, wherein the device divides the breathing chamber into a posterior chamber proximal to the patient and an anterior chamber distal to the patient in use, wherein the device is shaped and dimensioned such that at least a portion of an outer peripheral edge region of the device substantially conforms to an internal surface of at least one of the seal-forming structure and the plenum chamber, wherein at least one gap is formed between the outer peripheral edge region of the device and the internal surface of at least one of the seal-forming structure and the plenum chamber, and wherein the device comprises a plurality of apertures having a predetermined size, the plurality of apertures configured to:

reduce the velocity of the flow of air that is directed from the anterior chamber, through the plurality of apertures, and into the posterior chamber such that turbulence of the air in the posterior chamber is less than turbulence of the air in the anterior chamber, and reduce the velocity of an expiratory flow of gas from the patient's airways that is directed from the posterior chamber, through the plurality of apertures, and into the anterior chamber such that turbulence of the air in the posterior chamber is less than turbulence of the air in the anterior chamber.

2. The patient interface of claim 1, wherein the outer peripheral edge region pneumatically seals against the internal surface of at least one of the seal-forming structure and the plenum chamber.

3. The patient interface of claim 1, wherein at least a portion of the outer peripheral edge region of the device is fixedly attached to the internal surface of at least one of the seal-forming structure and the plenum chamber with an adhesive.

4. The patient interface of claim 1, wherein at least a portion of the outer peripheral edge region of the device is removably attached to the internal surface of at least one of the seal-forming structure and the plenum chamber with clips.

5. The patient interface of claim 1, wherein the plurality of apertures are uniform in size across the entire device.

6. The patient interface of claim 5, wherein the plurality of apertures are uniform in shape across the entire device.

7. The patient interface of claim 1, wherein the plurality of apertures are not uniform in density across the entire device.

8. The patient interface of claim 1, wherein each of the plurality of apertures has a posterior area adjacent to the posterior chamber and an anterior area adjacent to the anterior chamber.

9. The patient interface of claim 8, wherein the posterior area of each of the plurality of apertures is equal to the anterior area of each of the plurality of apertures.

10. The patient interface of claim 1, wherein a flow path through each of the plurality of apertures is linear.

11. The patient interface of claim 1, wherein the device is constructed from a material that is resistant to absorption of moisture and heat.

12. The patient interface of claim 11, wherein the material is any one of the group consisting of nylon, polycarbonate, silicone, polyurethane, a thermoplastic elastomer, and a hydrophobic polymer.

13. The patient interface of claim 11, wherein the device is constructed from a single, continuous, and homogeneous piece of the material.

14. The patient interface of claim 1, wherein the device has a mesh, foam, or woven structure.

15. The patient interface of claim 1, wherein the device is positioned within the breathing chamber such that the volume of the posterior chamber is greater than the volume of the anterior chamber.

16. The patient interface of claim 1, wherein the vent is positioned on the elbow.

17. The patient interface of claim 1, wherein each of the apertures is circular in shape at an anterior side and at a posterior side of the device.

18. The patient interface of claim 1, wherein the device further comprises a heat and moisture exchanger constructed from paper.

19. The patient interface of claim 1,
wherein at least a portion of the outer peripheral edge region of the device is removably attached to the internal surface of at least one of the seal-forming structure and the plenum chamber with clips,
wherein the plurality of apertures are uniform in size across the entire device, and
wherein a flow path through each of the plurality of apertures is linear.

20. The patient interface of claim 1, further comprising an anti-asphyxia valve.

21. The patient interface of claim 1, wherein the vent is positioned on the plenum chamber.

22. The patient interface of claim 1, wherein a posterior surface of the device that faces the patient in use is concave.

* * * * *